US011414486B2

(12) United States Patent
Jensen et al.

(10) Patent No.: US 11,414,486 B2
(45) Date of Patent: Aug. 16, 2022

(54) TRANSGENE GENETIC TAGS AND METHODS OF USE

(71) Applicant: Seattle Children's Hospital, Seattle, WA (US)

(72) Inventors: Michael C. Jensen, Bainbridge Island, WA (US); Adam Johnson, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 243 days.

(21) Appl. No.: 16/794,673

(22) Filed: Feb. 19, 2020

(65) Prior Publication Data
US 2021/0002364 A1  Jan. 7, 2021

Related U.S. Application Data

(62) Division of application No. 15/302,420, filed as application No. PCT/US2015/024895 on Apr. 8, 2015, now Pat. No. 10,611,837.
(Continued)

(51) Int. Cl.
| | |
|---|---|
| C07K 14/705 | (2006.01) |
| C07K 14/71 | (2006.01) |
| C07K 14/725 | (2006.01) |
| A61K 35/17 | (2015.01) |
| A61K 35/28 | (2015.01) |
| A61K 38/17 | (2006.01) |
| C12N 15/85 | (2006.01) |
| C12N 15/86 | (2006.01) |
| C12N 5/0783 | (2010.01) |
| C12N 15/62 | (2006.01) |
| C07K 16/28 | (2006.01) |
| C07K 14/715 | (2006.01) |

(Continued)

(52) U.S. Cl.
CPC .......... *C07K 16/2803* (2013.01); *A61K 35/17* (2013.01); *A61K 35/28* (2013.01); *A61K 38/179* (2013.01); *A61K 38/1774* (2013.01); *A61K 38/1793* (2013.01); *A61K 39/3955* (2013.01); *C07K 14/7051* (2013.01); *C07K 14/70517* (2013.01); *C07K 14/70521* (2013.01); *C07K 14/70578* (2013.01); *C07K 14/71* (2013.01); *C07K 14/7151* (2013.01); *C07K 16/2818* (2013.01); *C07K 16/32* (2013.01); *C12N 5/0636* (2013.01); *C12N 9/12* (2013.01); *C12N 15/85* (2013.01); *C12Y 207/10001* (2013.01); *A61K 2035/124* (2013.01); *A61K 2039/505* (2013.01); *A61K 2039/5156* (2013.01); *A61K 2039/5158* (2013.01); *A61K 2039/572* (2013.01); *C07K 2317/14* (2013.01); *C07K 2317/524* (2013.01); *C07K 2317/526* (2013.01); *C07K 2317/53* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2510/00* (2013.01); *C12N 2800/90* (2013.01)

(58) Field of Classification Search
CPC .......... C07K 14/70521; C07K 2319/00; C07K 2319/03; C07K 2317/53; A61K 2039/5156; A61K 2039/5158; C12N 2510/00; C12N 2800/90; C12N 15/62; C12N 15/86; C12N 15/87; C12N 2740/15041
See application file for complete search history.

(56) References Cited

U.S. PATENT DOCUMENTS

| | | | |
|---|---|---|---|
| 5,783,186 A | 7/1998 | Arakawa et al. | |
| 6,040,177 A | 3/2000 | Riddell et al. | |

(Continued)

FOREIGN PATENT DOCUMENTS

| | | |
|---|---|---|
| CN | 102227503 A | 10/2011 |
| DE | 102011118018 | 4/2013 |

(Continued)

OTHER PUBLICATIONS

Aalberse et al., "IgG4 breaking the rules," Immunology (2002) 105:9-19.
(Continued)

*Primary Examiner* — Hong Sang
(74) *Attorney, Agent, or Firm* — Knobbe, Martens, Olson & Bear LLP

(57) ABSTRACT

The present invention provides genetic tags operably linked to transgenes. The expression of the genetic tag allows identification, detection, selection, and ablation of cells expressing the transgene and the genetic tag. In some alternatives the genetically modified host cell comprises a transgene comprising a polynucleotide coding for a chimeric antigen receptor comprising a ligand binding domain, a polynucleotide comprising a spacer region, a polynucleotide comprising a transmembrane domain, and a polynucleotide comprising an intracellular signaling domain and a polynucleotide coding for a genetic tag. In some alternatives the genetically modified host cell comprises a transgene comprising a polynucleotide coding for a chimeric antigen receptor comprising a ligand binding domain, a polynucleotide comprising a spacer region, a polynucleotide comprising a transmembrane domain, and a polynucleotide comprising an intracellular signaling domain and a polynucleotide coding for a genetic tag, and wherein the polypeptide further comprises a flexible linker comprising amino acids GGGSGGGS (SEQ ID NO:45). Pharmaceutical formulations produced by the method, and methods of using the same, are also described.

20 Claims, 25 Drawing Sheets

Specification includes a Sequence Listing.

Related U.S. Application Data

(60) Provisional application No. 61/977,751, filed on Apr. 10, 2014, provisional application No. 61/986,479, filed on Apr. 30, 2014, provisional application No. 62/058,973, filed on Oct. 2, 2014, provisional application No. 62/088,363, filed on Dec. 5, 2014, provisional application No. 62/089,730, filed on Dec. 9, 2014, provisional application No. 62/090,845, filed on Dec. 11, 2014.

(51) Int. Cl.
    C07K 16/32      (2006.01)
    A61K 39/395     (2006.01)
    C12N 9/12       (2006.01)
    A61K 39/00      (2006.01)
    A61K 35/12      (2015.01)

(56) References Cited

U.S. PATENT DOCUMENTS

| | | |
|---|---|---|
| 7,070,995 B2 | 7/2006 | Jensen |
| 7,709,253 B2 | 5/2010 | Gambhir et al. |
| 7,910,101 B2 | 3/2011 | Cunningham et al. |
| 8,822,647 B2 | 9/2014 | Jensen |
| 10,266,592 B2 | 4/2019 | Jensen |
| 10,611,837 B2 | 4/2020 | Jensen et al. |
| 2002/0111474 A1 | 8/2002 | Capon et al. |
| 2003/0148982 A1 | 8/2003 | Brenner et al. |
| 2005/0060762 A1 | 3/2005 | Bleck |
| 2005/0129671 A1 | 6/2005 | Cooper et al. |
| 2006/0160090 A1 | 7/2006 | Anzures et al. |
| 2007/0087346 A1 | 4/2007 | Ciliberto et al. |
| 2007/0166318 A1 | 7/2007 | Macina et al. |
| 2009/0098142 A1 | 4/2009 | Kasaian et al. |
| 2009/0098604 A1 | 4/2009 | Gallo et al. |
| 2010/0226901 A1 | 9/2010 | Smolke |
| 2011/0287020 A1 | 11/2011 | Gruber et al. |
| 2012/0297493 A1 | 11/2012 | Cooper et al. |
| 2012/0301447 A1 | 11/2012 | Jensen |
| 2013/0011394 A1 | 1/2013 | Knoetgen |
| 2013/0143559 A1 | 6/2013 | Nishida et al. |
| 2013/0280220 A1 | 10/2013 | Ahmed et al. |
| 2013/0287748 A1 | 10/2013 | June et al. |
| 2014/0056868 A1 | 2/2014 | Zechiedrich et al. |
| 2014/0112956 A1 | 4/2014 | Karlsson-Parra et al. |
| 2014/0271635 A1 | 9/2014 | Brogdon et al. |
| 2014/0314795 A1 | 10/2014 | Riddell et al. |
| 2015/0038694 A1 | 2/2015 | Nicotra |
| 2015/0120622 A1 | 4/2015 | Kobatake |
| 2015/0299656 A1 | 10/2015 | Gattinoni et al. |
| 2015/0329640 A1 | 11/2015 | Finer |
| 2016/0017048 A1 | 1/2016 | Dotti et al. |
| 2017/0015746 A1 | 1/2017 | Jensen |
| 2017/0029774 A1 | 2/2017 | Jensen et al. |
| 2017/0209543 A9 | 7/2017 | Jensen |
| 2017/0224733 A1 | 8/2017 | Badie et al. |
| 2018/0009891 A1 | 1/2018 | Jensen |
| 2018/0028567 A1 | 2/2018 | Li et al. |
| 2019/0248891 A1 | 8/2019 | Jensen et al. |
| 2020/0181624 A1 | 6/2020 | Jensen et al. |
| 2020/0215108 A1 | 7/2020 | Jensen |

FOREIGN PATENT DOCUMENTS

| | | |
|---|---|---|
| JP | 2006-518753 | 8/2006 |
| RU | 2003 129 528 A | 4/2005 |
| WO | WO 92/08796 | 5/1992 |
| WO | WO 94/00143 | 1/1994 |
| WO | WO 98/18923 | 5/1998 |
| WO | WO 00/23573 | 4/2000 |
| WO | WO 01/098506 | 12/2001 |
| WO | WO 02/072605 | 9/2002 |
| WO | WO 02/097099 | 12/2002 |
| WO | WO 03/025228 | 3/2003 |
| WO | WO 03/087338 | 10/2003 |
| WO | WO 04/029284 | 4/2004 |
| WO | WO 05/017102 | 2/2005 |
| WO | WO 05/040212 | 5/2005 |
| WO | WO 07/137267 | 11/2007 |
| WO | WO 08/012237 | 1/2008 |
| WO | WO 09/013359 | 1/2009 |
| WO | WO 10/036986 | 4/2010 |
| WO | WO 10/141543 | 12/2010 |
| WO | WO 11/056894 | 5/2011 |
| WO | WO 12/031744 | 3/2012 |
| WO | WO 12/079000 | 6/2012 |
| WO | WO 12/099973 | 7/2012 |
| WO | WO 12/129514 | 9/2012 |
| WO | WO 12/140130 | 10/2012 |
| WO | WO 12/167192 | 12/2012 |
| WO | WO 13/074916 | 5/2013 |
| WO | WO 13/123061 | 8/2013 |
| WO | WO 13/126733 | 8/2013 |
| WO | WO 13/154760 | 10/2013 |
| WO | WO 13/177533 | 11/2013 |
| WO | WO 13/178635 | 12/2013 |
| WO | WO 14/031687 | 2/2014 |
| WO | WO 14/039044 | 3/2014 |
| WO | WO 14/055657 | 4/2014 |
| WO | WO 14/139672 | 9/2014 |
| WO | WO 15/066551 | 5/2015 |
| WO | WO 15/075468 | 5/2015 |
| WO | WO 15/105522 | 7/2015 |
| WO | WO 15/142675 | 9/2015 |
| WO | WO 15/157399 | 10/2015 |
| WO | WO 15/157432 | 10/2015 |

OTHER PUBLICATIONS

Aertgeerts et al., "Structural analysis of the mechanism of inhibition and allosteric activation of the kinase domain of HER2 protein," Journal of Biological Chemistry (2011) vol. 286, No. 21, p. 18756-18765, Bech Tet CT, c. 18759-18765.

Ahmed et al., "Regression of experimental medulloblastoma following transfer of HER2-specific T cells," Cancer Res. (Jun. 15, 2007) 67(12):5957-64.

Ahmed, Nabil, "CMV-specific Cytotoxic T Lymphocytes Expressing CAR Targeting HER2 in Patients With GBM (HERT-GBM)," ClinicalTrials.gov Identifier: NCT01109095 (Apr. 22, 2010) pp. 1-8.

Ahmed, Nabil, "Her2 Chimeric Antigen Receptor Expressing T Cells in Advanced Sarcoma," ClinicalTrials.gov Identifier: NCT00902044 (May 14, 2009) pp. 1-11.

Altschul et al., "Local Alignment Statistics, [27] Multiple Alignment and Phylogenetic Trees," Methods in Enzymology (1996) 266:460-480.

Bejcek et al. "Development and Characterization of Three Recombinant Single Chain Antibody Fragments (scFvs) Directed against the CD19 Antigen," Cancer Res (1995) 55:2346-2351.

Berglund et al., "The epitope space of the human proteome," Protein Science (2008) 17:606-613.

Brentjens et al: "CD19-targeted T cells rapidly induce molecular remissions in adults with chemotherapy-refractory acute lymphoblastic leukemia", Science Translational Medicine, 5(177), Mar. 20, 2013.

Budde, et al., "Combining a CD20 Chimeric Antigen Receptor and an Inducible Caspase 9 Suicide Switch to Improve the Efficacy and Safety of T Cell Adoptive Immunotherapy for Lymphoma", PLOS ONE (2013) 8(12): e82742. https://doi.org/10.1371/iournal.pone.0082742.

Cartellieri et al., "A Novel Ex Vivo Isolation and Expansion Procedure for Chimeric Antigen Receptor Engrafted Human T Cells," PLOS ONE (Apr. 3, 2014) vol. 9, No. 4, e93745, pp. 1-12.

Cha et al., "IL-7 + IL-15 are superior to IL-2 for the ex vivo expansion of 4T1 mammary carcinomaspecific T cells with greater efficacy against tumors in vivo," Breast Cancer Research and Treatment, Springer, NY, US (Oct. 14, 2009) vol. 122, No. 2, pp. 359-369.

Chen et al., "Ex vivo expansion of dendritic-cell-activated antigen-specific CD4+ T cells with anti-CD3/CD28, interleukin 7, and

(56) References Cited

OTHER PUBLICATIONS interleukin-15: Potential for adoptive T-cell immunotherapy," Clinical Immunology (2006) vol. 119, pp. 21-31.
Chen et al., "Minicircle DNA vectors devoid of bacterial DNA result in persistent and high-level transgene expression in vivo", Mol Ther. (2003) 8(3), 495-500.
Chen et al: "Fusion Protein Linkers: Property, Design and Functionality", Adv Drug Deliv Rev., Oct. 15, 2013; 65(10), pp. 1357-1369.
Cho et al., "Structure of the extracellular region of HER2 alone and in complex with the Herceptin Fab", Nature (Feb. 13, 2003) 421(6924):756-760.
Circosta et al., "T Cell Receptor (TCR) Gene Transfer with Lentiviral Vectors Allows Efficient Redirection of Tumor Specificity ikn Naive and Memory T Cells Without Prior Stimulation of Endogenous TCR," Human Gene Therapy (Nov. 18, 2009) vol. 20, No. 12, pp. 1576-1588.
Converse et al: "Counterselection and Co-Delivery of Transposon and Transposase Functions for Sleeping Beauty-Mediated Transposition in Cultured Mammalian Cells", Bioscience Reports, Kluwer Academic Publishers-Plenum Publishers, NE (Dec. 1, 2004) vol. 24, No. 6, pp. 577-594.
Crewe et al., "Metabolism of Tamoxifen by recombinant human cytochrome P-450 enzymes: Formation of the 4-hydroxy, 4'-hydroxy and N-desmethyl metabolites and isomerization of trans-4-hydroxytamoxifen,"Drug Metab Dispos (2002) 30(8): 869-874.
Database Geneseq [Online] May 5, 2005 (May 5, 2005), "Human splice variant protein expressed in ovary cells DEX0487 002.orf. 4.", XP002771301, retrieved from EBI accession No. GSP:ADY30515. Database accession No. ADY30515 ; & WO 2005/017102 A2 (Diadexus Inc [US]; Macina Roberto A [US]; Turner Leah R [US]; Sun Yong) Feb. 24, 2005 (Feb. 24, 2005).
Database UniProt [Online] Oct. 3, 2012 (Oct. 3, 2012), "SubName: Full=Receptor tyrosine-protein kinase erbB-2{ECO: 00003131 Ensembl:ENSP00000464252}; Flags: Fragment;", XP002771300, retrieved from EBI accession No. UNIPROT:J3QRJ7 Database accession No. J3QRJ7.
Dotti, Gianpietro, et al. "Design and development of therapies using chimeric antigen receptor-expressing T cells." Immunological reviews 257.1 (2014): 107-126.
Ercikan-Abali et al., "Active Site-Directed Double Mutants of Dihydrofolate Reductase," Cancer Res., (1996) vol. 56, No. 18, pp. 4142-4145.
Frankel et al., "Characterization of diphtheria fusion proteins targeted to the human interleukin-3 receptor," Protein engineering (2000) vol. 13, No. 8, p. 575-581.
Gagnon et al., "IL-6, in Synergy with IL-7 or IL-15, Stimulates TCR-lndependent Proliferation and Functional Differentiation of CD8+ T Lymphocytes," The Journal of Immunology (2008) 180:7958-7968.
Gallinari et al., "A Functionally Orthogonal Estrogen Receptor-Based Transcription Switch Specifically Induced by a Nonsteroid Synthetic Ligand," Chemistry and Biology (Aug. 1, 2005) vol. 12, No. 8, pp. 883-893.
Gargett et al., "Different cytokine and stimulation conditions influence the expansion and immune phenotype of third-generation chimeric antigen receptor T cells specific for tumor antigen GD2," Cytotherapy (2015) 17.4: 487-495.
Garrett et al., "Novel engineered trastuzumab conformational epitopes demonstrate in vitro and in vivo antitumor properties against HER-2/neu," The Journal of Immunology (Jun. 1, 2007) 178:7120-7131.
Ghatar et al., "Epitope Mapping of Human HER2 Specific Mouse Monoclonal Antibodies Using Recombinant Extracellular Subdomains," Asian Pacific Journal of Cancer Prevention (2017) 18(11):3103-3110.
Gianpietro Dotti et al.: "Design and development of therapies using chimeric antigen receptor-expressing T cells", Immunological Reviews, vol. 257, No. 1, Dec. 13, 2013 (Dec. 13, 2013), pp. 107-126.

Giry-Laterriere et al. "Polyswitch lentivectors: 'all-in-one' lentiviral vectors for drug-inducible gene expression, live selection, and recombination cloning", *Human Gene Therapy*, Oct. 2011, 22:1255-1267.
Godiska et al., "Linear plasmid vector for cloning of repetitive or unstable sequences in *Excherichia coli*," (Dec. 29, 2009) Nuc Acids Res, vol. 38, No. 6, e88, pp. 1-9.
Gottschalk, Stephen, "Her2 and TGFBeta CTLs in Treatment of Her2 Positive Malignancy (HERCREEM)", ClinicalTrials.gov Identifier: NCT00889954 (Apr. 29, 2009) pp. 1-9.
Grada et al., "TanCAR: A Novel Bispecific Chimeric Antigen Receptor for Cancer Immunotherapy", Mol Ther Nucleic Acids, (Jul. 9, 2013) 2:e105. doi: 10.1038/mtna.2013.32.
Han Weidong, "Treatment of Chemotherapy Refractory Human Epidermalgrowth Factor Receptor-2(HER-2) Positive Advanced Solid Tumors (CART-HER-2)", (Sep. 5, 2013) ClinicalTrials.gov Identifier: NCT01935843, pp. 1-7.
Holtkamp et al., "Modification of antigen-encoding RNA increases stability, translational efficacy, and T-cell stimulatory capacity of dendritic cells," Blood (Oct. 28, 2014), 2006/108:509-4017.
Hudecek et al. Receptor affinity and extracellular domain modifications affect tumor recognition by ROR1-specific chimeric antigen receptor T-cells. Clin Cancer Res. Jun. 15, 2013; 19(12): 3153-3164.
Hudecek et al., "The Non-Signaling Extracellular Spacer Domain of CD19-Specific Chimeric Antigen Receptors Is Decisive for in Vivo Anti-Tumor Activity," Blood (2012) vol. 120, No. 21, Abstract 951, 3 pages.
Huls et al., "First Clinical Trials Employing Sleeping Beauty Gene Transfer System and Artificial Antigen Presenting Cells to Generate and Infuse T Cells Expressing CD19-Specific Chimeric Antigen Receptor," Blood (2013) 122:166-166.
Jensen et al., "Designing chimeric antigen receptors to effectively and safely target tumors," Cum Opin Immunol. (Apr. 2015) 33:9-15.
Jensen et al.: "Design and implementation of adoptive therapy with chimeric antigen receptor-modified T cells", Immunological Reviews., Special Issue, Dec. 13, 2013 vol. 257, No. 1; 127-144.
Johansen et al., "Evaluation of Tet-on system to avoid transgene down-regulation in ex vivo gene transfer to the CNS," Gene Therapy (2002) 9:1291-1301.
Johnston et al. "Regulated expression of erythropoietin from an AAV vector safely improves the anemia of beta-thalassemia in a mouse model," Mol Ther. Apr. 1, 2003, 7(4):493-497.
Jonnalagadda et al., "Efficient selection of genetically modified human T cells using methotrexateresistant human dihydrofolate reductase," Gene Therapy, vol. 20, No. 8, Jan. 10, 2013, pp. 853-860.
Kacherovsky et al., "Combination of Sleeping Beauty transposition and chemically induced dimerization selection for robust production of engineered cells," Nucleic Acids Research (2012) 49(11):e85.
Kacherovsky et al., "Multiplexed 1-16 gene transfer to a human T-cell line by combining Sleeping Beauty transposon system with methotrexate selection". Biotechnology and Bioengineering (Jul. 23, 2015) vol. 112, No. 7, pp. 1429-1436.
Kay et al., "A robust system for production of minicircle DNA vectors", Nature Biotechnology, vol. 28, No. 12, Nov. 21, 2010, pp. 1287-1289.
Klebanoff et al., "IL-15 enhances the in vivo antitumor activity of tumor-reactive CD8+ T Cells," PNAS (Feb. 17, 2004) vol. 101, No. 7, pp. 1969-1974.
Kowolik et al., "CD28 costimulation provided through a CD19-specific chimeric antigen receptor enhances in vivo persistence and antitumor efficacy of adoptively transferred T cells," Cancer Res. (2006) 66(22):10995-11004.
Künkele et al., "Functional Tuning of CARs Reveals Signaling Threshold above which CD8+ CTL Antitumor Potency is Attenuated Due to Cell Fas-FasL-Dependent AICD," Cancer Immunol Res. (Jan. 9, 2015) vol. 3, No. 4, pp. 368-379.
Lemaigre et al., "Transcriptional control of genes that regulate glycolysis and gluconeogenesis in adult liver," Biochem. J. (1994) 303:1-14.
Leung et al., "Luminescent detection of DNA-binding proteins," Nuc Acids Res (2012) 40(3): 941-955.

(56) References Cited

OTHER PUBLICATIONS

Likar et al., "Using a mutated variant human deoxycytidine-kinase as a reporter gene for assessing adoptive T-cell therapy," Questions hematology, oncology and immunopathology in pediatrics (2012) vol. 11, No. 2, pp. 23-31. (Russian Language).
Littlewood et al., "A modified oestrogen receptor ligand-binding domain as an improved switch for the regulation of heterologous proteins," Nucleic Acids Res (May 25, 1995) 23(10):686-1690.
Litvinova et al., "The influence of immunoregulatory cytokines IL-2, IL-7, and IL-15 upon activation, proliferation, and apoptosis of immune memory T-cells in vitro." Cell and Tissue Biology (Dec. 11, 2013) vol. 7, No. 6, pp. 539-544.
Liu et al., "IL-21 synergizes with IL-7 to augment expansion and anti-tumor function of cytotoxic T cells," International Immunology (2007) vol. 19, No. 10, pp. 1213-1221.
Loeken, Mary R., "Effects of mutation of the CREB binding site of the somatostatin promoter on cyclic AMP responsiveness in CV-1 cells", *Gene Expr.* (1993) 3(3):253-264.
Lupton et al., "Dominant positive and negative selection using a hygromycin phosphotransferase-thymidine kinase fusion gene," Mol Cell Biol. (Jun. 1991) 11(6):3374-3378.
Maher, "Immunotherapy of Malignant Disease Using Chimeric Antigen Receptor Engrafted T Cells", *ISRN Oncology*, vol. 2012, pp. 1-23, Nov. 14, 2012.
Mátés et al., "Molecular evolution of a novel hyperactive Sleeping Beauty transposase enables robust stable gene transfer in vertebrates," Nature Genetics (Jun. 2009) vol. 41, No. 6, pp. 753-761.
McGehee et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol. (Apr. 1993) 7(4):551-560.
McKinlay et al., "Blood monocytes, myeloid dendritic cells and the cytokines interleukin (IL)-7 and IL-15 maintain human CD4+ T memory cells with mixed helper/regulatory function," Immunology (2006) vol. 120, pp. 392-403.
Morgan et al., "Case report of a serious adverse event following the administration of T cells transduced with a chimeric antigen receptor recognizing ERBB2," Mol Ther. (Apr. 2010) 18(4):843-51. doi: 10.1038/mt.2010.24. Epub Feb. 23, 2010.
Muftuoglu et al., "CD161 Expression Identifies a Distinct Subset of Drug-Effluxing Viral-Specific Memory CD4+ T Cells That Preferentially Survive Cytotoxic Chemotherapy," Blood (2012) 122(21):2024.
O'Reilly et al., "Identification of an activating transcription factor (ATF) binding site in the human transforming growth factor-beta 2 promoter," J. Biol. Chem. (Oct. 5, 1992) 267:19938-19943.
Pakula et al., "Genetic analysis of protein stability and function," Annual review of genetics (1989) vol. 23, No. 1, p. 289-310, c.305-306.
Papapetrou et al. "Harnessing endogenous miR-181a to segregate transgenic antigen receptor expression in developing versus post-thymic T cells in murine hematopoietic chimeras", The Journal of clinical investigation. Jan. 5, 2009; 119(1):157-68.
Park et al., "Adoptive Transfer of Chimeric Antigen Receptor Re-Directed Cytolytic T Lymphocyte Clones in Patients with Neuroblastoma," Mol. Ther. (Apr. 2007) vol. 15, No. 4; pp. 825-833.
Pezutto et al., May 1, 1987, CD19 monoclonal antibody HD37 inhibits anti-immunoglobulin-induced B cell activation and proliferation, The Journal of Immunology, 138(9):2793-2799.
Pollock et al. "Delivery of a stringent dimerizer-regulated gene expression system in a single retroviral vector," Proc Natl Acad Sci. USA Nov. 21, 2000, 97(24):13221-1326.
Promega, "pSP64 Poly(A) Vector Sequence and Map," Technical Bulletin No. 052, Revised May 2000, pp. 1-8.
Riddell et al. "Adoptive therapy with chimeric antigen receptor modified T cells of defined subset composition." Cancer journal (Sudbury, Mass. ) 20.2 (2014): 141-144.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3(3):319-338.
Roscilli et al., "Long-term and tight control of gene expression in mouse skeletal muscle by a new hybrid human transcription factor," Molecular Therapy (Nov. 2002) 1;6(5):653-63.
Sadelain et al., "The basic principles of chimeric antigen receptor (CAR) design," Cancer discovery (2013) 3 (4): 388-98.
Schmittgen et al. "Analyzing real-time PCR data by the comparative C(T) method", *Nat Protoc.* 2008;3(6):1101-8.
Sengupta et al., "Interleukin-13 Receptor Alpha 2-Targeted Glioblastoma Immunotherapy," BioMed Research International, (Aug. 27, 2014) vol. 2014, Article ID: 952128, pp. 1-8.
Sharma et al., "Efficient Sleeping Beauty DNA Transposition from DNA Minicircles," Mol Ther Nuc Acids (2013) 2:e74, 1-10.
Surh et al., "Homeostasis of memory T cells," Immunological Reviews (2006) vol. 211, pp. 154-163.
Terakura et al., "Generation of CD19-chimeric antigen receptor modified CD8+ T cells derived from virus-specific central memory T cells," Gene Therapy (Oct. 26, 2011) 119(1), pp. 72-82.
Treisman, R. "The SRE: a growth factor responsive transcriptional regulator. (PMID:2133110)", *Seminars in Cancer Biology*, Feb. 1, 1990, 1(1):47-58.
Vigna et al., "Robust and Efficient Regulation of Transgene Expression in Vivo by Improved Tetracycline-Dependent Lentiviral Vectors," Mol. Therapy (2002) 5(3):252-261.
Vogt et al., "Doxycycline-regulated gene expression in the opportunistic fungal pathogen Aspergillus fumigatus," BMC Microbiol. (2005) 5(1):11 pages.
Wang et al., "Phenotypic and Functional Attributes of Lentivirus Modified CD19-specific Human CD8+ Central Memory Tcells Manufactured at Clinical Scale," J Immunotherapy (2012) vol. 35, pp. 689-701.
Wang et al., "A transgene-encoded cell surface polypeptide for selection, in vivo tracking, and ablation of engineered cells", BLOOD, vol. 118, No. 5, Aug. 4, 2011 (Aug. 4, 2011), pp. 1255-1263.
Weill et al., "Translational control by changes in poly(A) tail length: recycling mRNAs," Nature Structural & Molecular Biology (Jun. 2012) vol. 19, No. 6, pp. 577-585.
Xu et al., "Closely related T-memory stem cells correlate with in vivo expansion of CAR.CD19-T cells and are preserved by IL-7 and IL-15," Blood (Jun. 12, 2014) vol. 123, No. 24, pp. 3750-3759.
Yant et al. "Mutational Analysis of the N-Terminal DNA-Binding Domain of Sleeping Beauty Transposase: Critical Residues for DNA Binding and Hyperactivity in Mammalian Cells," Mol. Cell. Biol. (2004) 24(20):9239-9247.
Ye et al., "Characterization of a silencer regulatory element in the human interferon-gamma promoter," J. Biol. Chem., (Oct. 14, 1994) 269:25728-25734.
Zambon et al., "Increased Expression of the Pro-Apoptotic Protein BIM: A Mechanism for cAMP/PKA-Induced Apoptosis of Immature T Cells," J. Biol. Chem. (2011) 286(38):33260-33267.
Zeng et al., "Synergy of IL-21 and IL-15 in regulating CD8+ T cell expansion and function," JEM (Jan. 3, 2005) vol. 201, No. 1, pp. 139-148.
EP Examination dated Mar. 6, 2018 for EP 15 776 745.0.
First Examination Report dated Feb. 28, 2017, received in New Zealand Patent Application N. 725079 filed Oct. 12, 2016.
Further Examination Report dated Oct. 24, 2017, received in New Zealand Patent Application No. 725079 filed Oct. 12, 2016.
First Examination Report dated Sep. 26, 2018 for New Zealand Application No. 739448.
International Search Report and Written Opinion dated Jul. 16, 2015, received in PCT/US2015/24895 filed Apr. 8, 2015.
Extended European Search Report dated Jul. 17, 2017 in the European Patent Application No. 15776501.7, filed on Oct. 20, 2016.
Burns et al., 2010, A high molecular weight melanoma-associated antigen-specific chimeric antigen receptor redirects lymphocytes to target human melanomas, Cancer Research, 70(8):3027-3033.

(56) References Cited

OTHER PUBLICATIONS

Chen et al., 2013, Fusion protein linkers: property, design and functionality, Advanced Drug Delivery Reviews, 65(10):1357-1369.

Chen et al., Jan. 2007, Generation of a transgenic mouse model with chondrocyte-specific and tamoxifen-inducible expression of cre recombinase, Genesis, 45:44-50.

Courtney et al., 2018, TCR signaling: mechanisms of initiation and propagation, Trends in Biochemical Sciences, 43(2):108-123.

Dolezal et al., 2000, ScFv multimers of the anti-neuraminidase antibody NC10: shortening of the linker in single-chain Fv fragment assembled in VL to VH orientation drives the formation of dimers, trimers, tetramers and higher molecular mass multimers, Protein Engineering, 13(8):565-574.

Guedan et al., 2018, Enhancing Car T cell persistence through ICOS and 4-1BB costimulation. JCI Insight, 3(1):11-13.

Guha et al., 2017, Frontline science: functionally impaired geriatric CAR-T cells rescued by increased α5β1 integrin expression, Journal of Leukocyte Biologys, 102(2):201-208.

Hege et al., 2017, Safety, tumor trafficking and immunogenicity of chimeric antigen receptor (CAR)-T cells specific for TAG-72 in colorectal cancer, Journal for Immunotherapy of Cancer, 5(1):1-14.

Hong et al., "Diverse solid tumors expressing a restricted eptitope of L1-CAM can be targeted by chimeric antigen receptor redirected T lymphocytes," J Immunotherapy (2014) vol. 37, No. 2, pp. 93-104.

Hudecek et al., Sep. 11, 2014, "The Nonsignaling Extracellular Spacer Domain of Chimeric Antigen Receptors Is Decisive for In Vivo Antitumor Activity", Cancer Immunology Research, 3(2):125-135.

Long et al., 2015, 4-1BB costimulation ameliorates T cell exhaustion induced by tonic signaling of chimeric antigen receptors, Nature Medicine, 21(6):581-590.

Maeda et al., 1997, Engineering of functional chimeric protein G—Vargula Luciferase, Analytical Biochemistry, 249(2):147-152.

Maus et al., 2013, T cells expressing chimeric antigen receptors can cause anaphylaxis in humans, Cancer Immunology Research, 1(1):26-31.

Pelloquin et al., Dec. 1986, Human B lymphocytes immortalization by Epstein-Barr virus in the presence of cyclosprin A, In Vitro Cell Dev Biol, 22(12):689-694.

Richman et al., 2018, High-affinity GD2-specific Car T cells induce fatal encephalitis in a preclinical neuroblastoma model, Cancer Immunology Research, 6(1):36-46.

Robinsons et al., Jan. 1991, Metabolites, pharmacodynamics, and pharmacokinetics of tamoxifen in rats and mice compared to the breast cancer patient, Drug Metab Dispos, 19(1):36-43.

Schamel et al., 2019, The TCR is an allosterically regulated macromolecular machinery changing its conformation while working, Immunological Reviews, 291(1):8-25.

Teplyakov et al., 2014, Antibody modeling assessment II. Structures and models, Proteins: Structure, Function, and Bioinformatics, 82(8):1563-1582.

Turtle et al., 2016, CD19 CAR-T cells of defined CD4+: CD8+ composition in adult B cell ALL patients, The Journal of Clinical Investigation, 126(6):2123-2138.

Wilke et al., Apr. 27, 2012, Dual targeting of ErbB2 and MUC1 in breast cancer using chimeric antigen receptors engineered to provide complementary signaling, Journal of Clinical Immunology, 32(5):1059-1070.

Zheng, Changyu et al., "All Human EF1" Promoters Are Not Equal: Markedly Affect Gene Expression in Constructs from Different Sources, International Journal of Medical Sciences (2014) 11(5):404-408.

FIG. IA
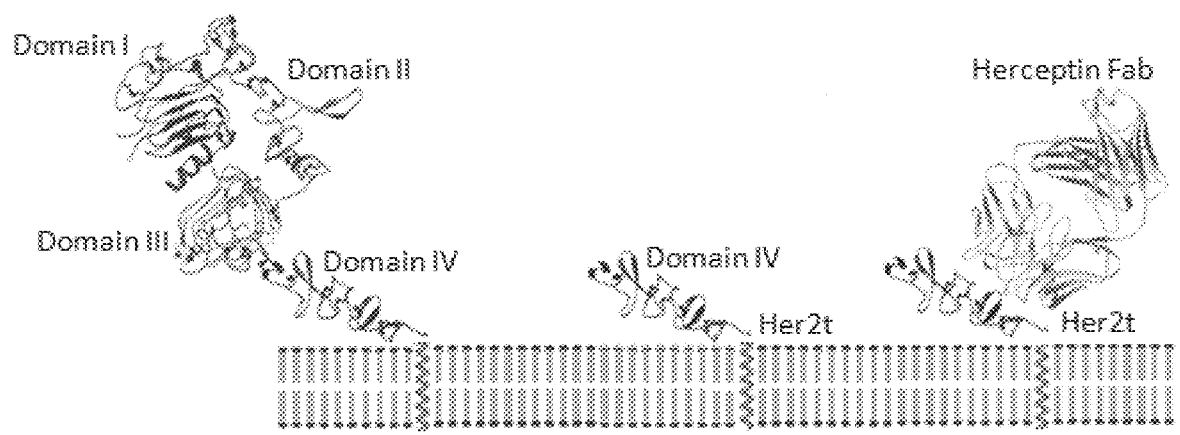
FIG. IB
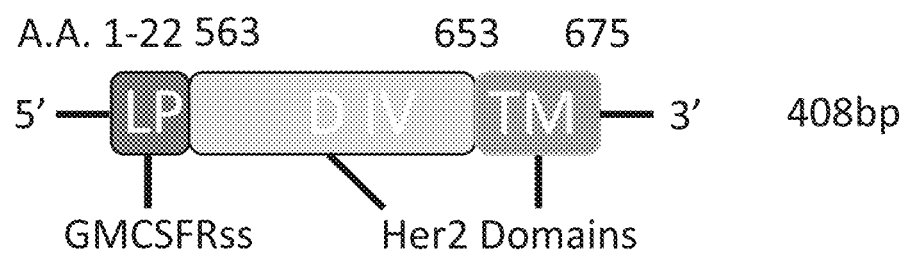

FIG. IC
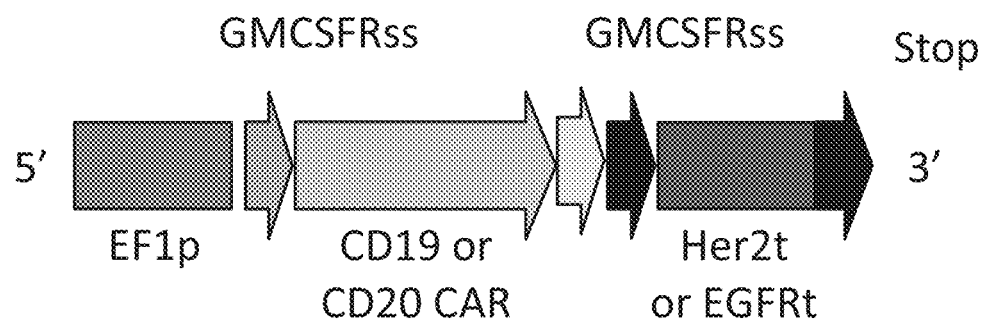

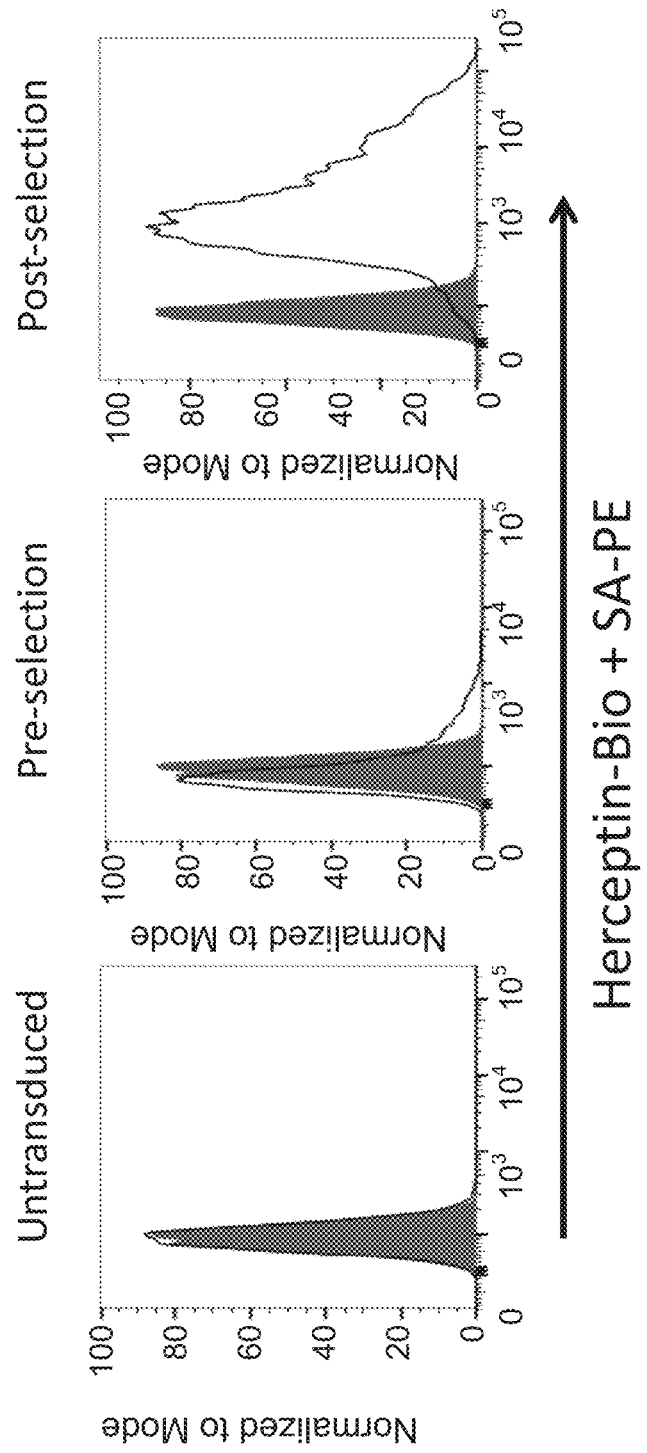

FIG. 3A
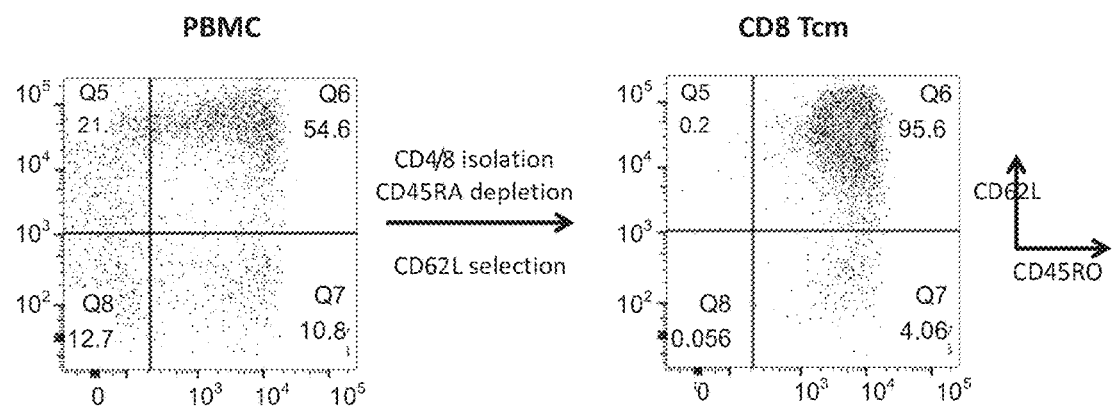
FIG. 3B
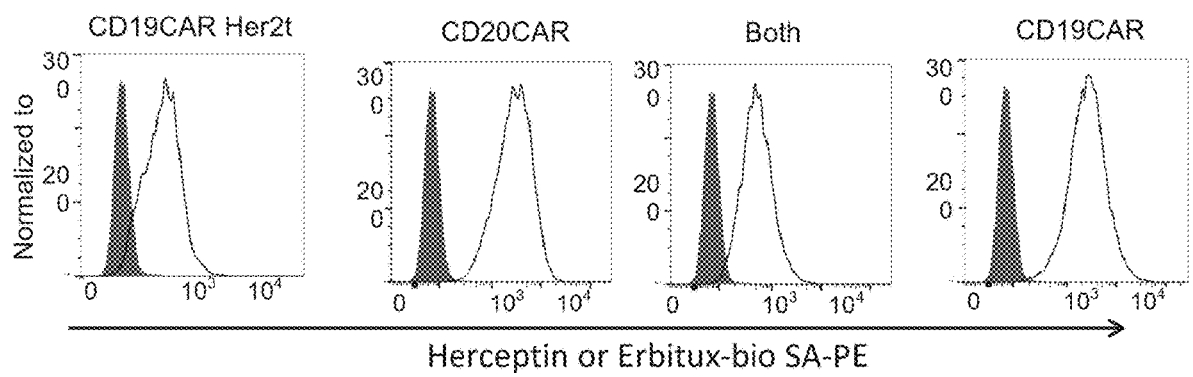
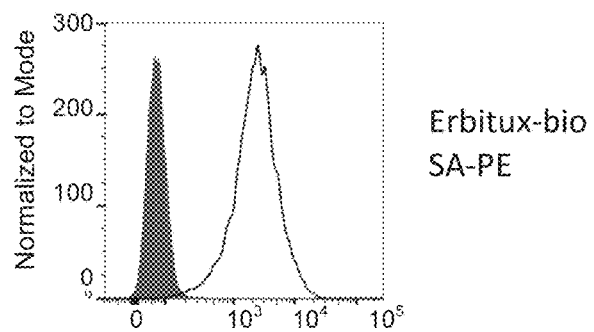

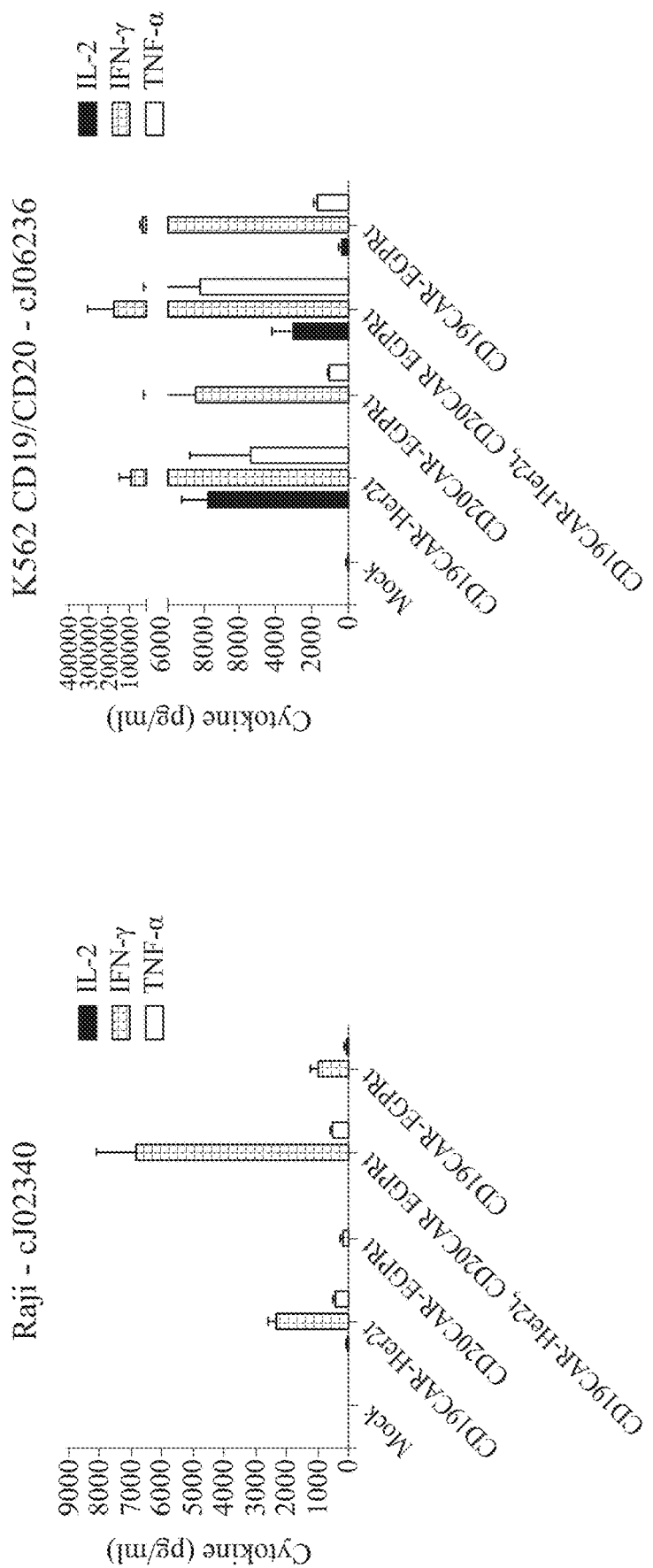

FIG. 4D
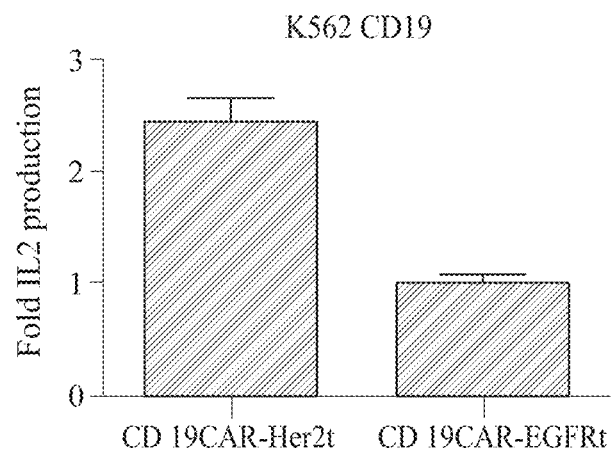
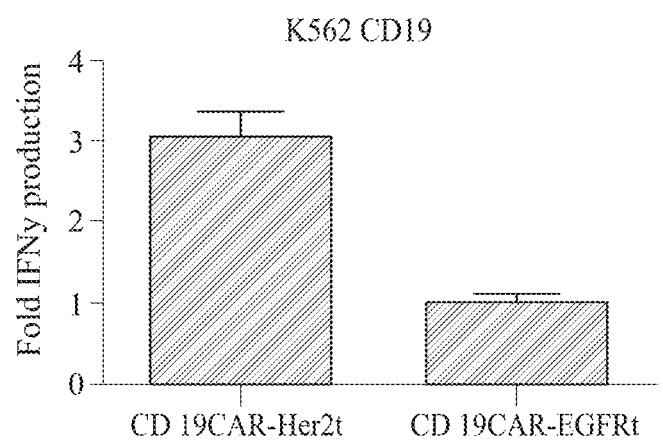
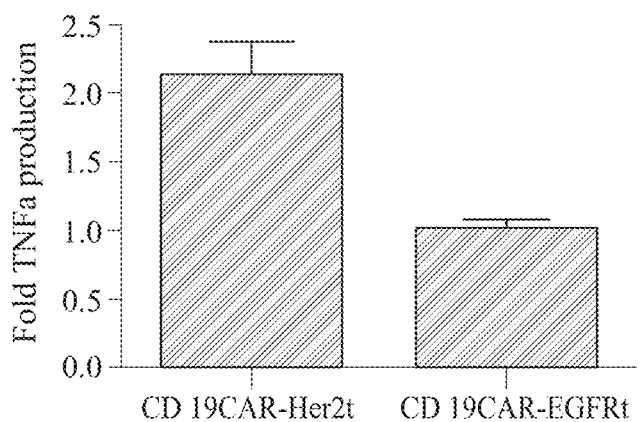

FIG. 5D
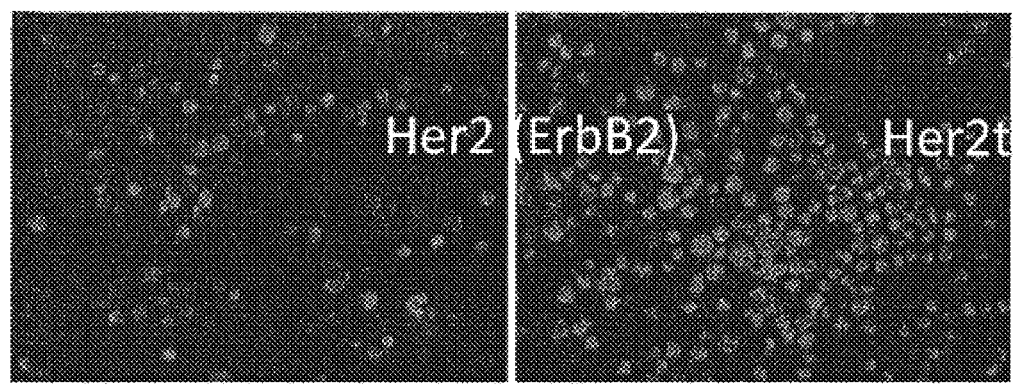
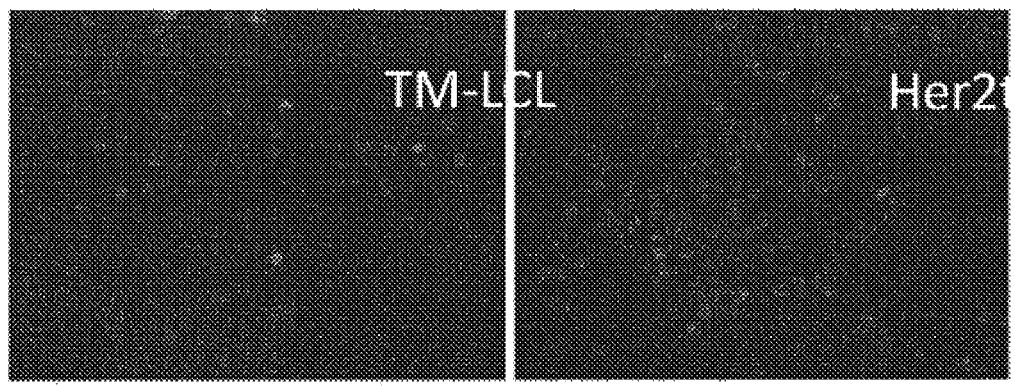
Herceptin-bio SA-AF647
Hoechst

FIG. 9 (CONT.)
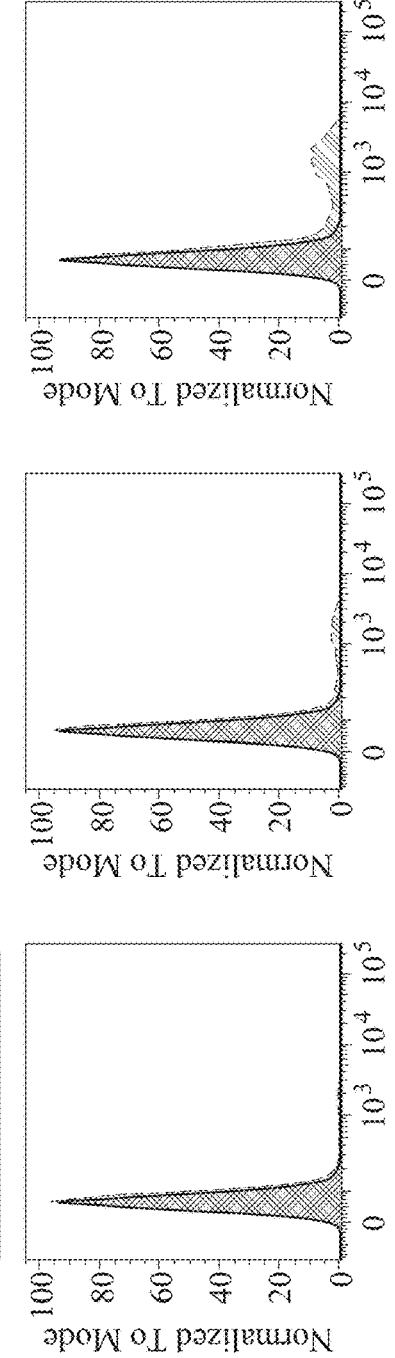
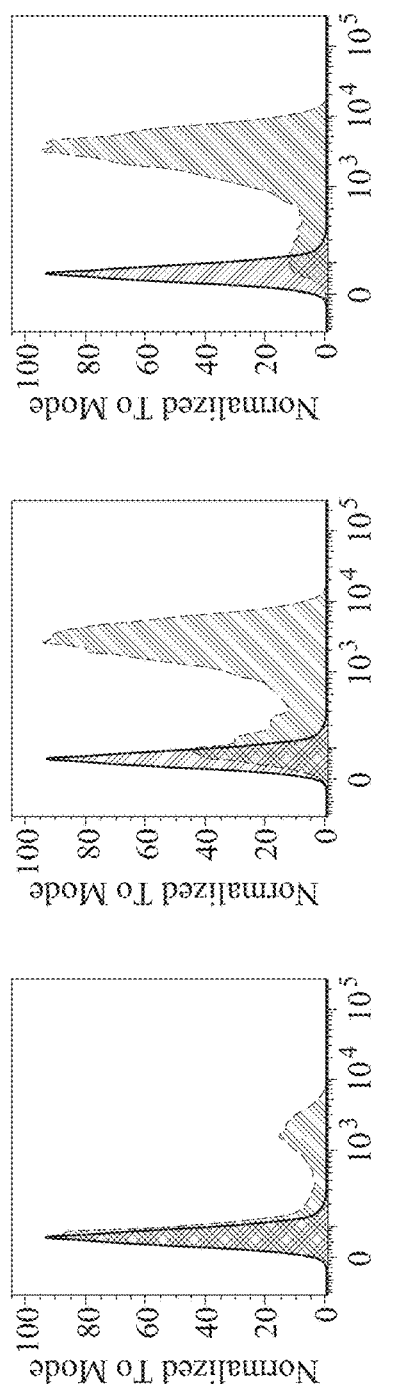

TRANSGENE GENETIC TAGS AND METHODS OF USE

CROSS REFERENCE TO RELATED APPLICATIONS

This application is a division of U.S. Ser. No. 15/302,420 filed Oct. 6, 2016 which is the U.S. National Phase of Int. App. No. PCT/US2015/024895 filed on Apr. 8, 2015, which claims priority to: U.S. Prov. App. No. 62/058,973, filed Oct. 2, 2014, U.S. Prov. App. No. 61/977,751 filed Apr. 10, 2014, U.S. Prov. App. No. 61/986,479 filed Apr. 30, 2014, U.S. Prov. App. No. 62/089,730 filed Dec. 9, 2014, U.S. Prov. App. No. 62/090,845 filed Dec. 11, 2014, and U.S. Prov. App. No. 62/088,363 filed Dec. 5, 2014 which are each expressly incorporated by reference in its entirety.

REFERENCE TO SEQUENCE LISTING

The present application is being filed along with a Sequence Listing in electronic format. The Sequence Listing is provided as a file entitled SCRI066D1SEQLISTING, created Feb. 11, 2020, which is approximately 44 Kb in size. The information in the electronic format of the Sequence Listing is incorporated herein by reference in its entirety.

FIELD OF THE INVENTION

The present invention relates to the compositions and methods useful for detecting transgene expression in cells.

BACKGROUND OF THE INVENTION

Expression of transgenes in cells is becoming an important therapeutic approach for a variety of conditions. For example, in adoptive immunotherapy, human T lymphocytes are engineered by gene transfer to express chimeric antigen receptors (CARs) specific for surface molecules expressed on tumor cells. Chimeric receptors are synthetic receptors that include an extracellular ligand binding domain, most commonly a single chain variable fragment of a monoclonal antibody (scFv) linked to intracellular signaling components, most commonly CD3ζ alone or combined with one or more costimulatory domains. Other examples of conditions treated with transgene modified cells include thalassemia, hemophilia, myocardial infarction, and severe combined immunodeficiency. However, a major issue remains with obtaining stable expression of transgene expression at levels comparable to endogenous genes. There is a need to identify compositions and methods for selecting and/or detecting cells that express transgenes at high levels.

SUMMARY OF THE INVENTION

The use and selection of homogenous products has been a limiting factor to the clinical success and reproducibility of gene therapy strategies. As provided herein, a candidate genetic tag and tool for cellular engineering was designed. In some alternatives, a genetic tag comprises an epitope based on human Her2, designated Her2t. In a specific alternative, Her2t is devoid of all Her2 intracellular components, yet contains the Her2 transmembrane region, a conformationally intact epitope recognized by the monoclonal antibody trastuzumab (Herceptin) and a peptide to facilitate surface expression. Three variants of the Her2t construct, one containing the full Her2 Domain IV and two conformational epitopes that were designed based on the three-dimensional structure of Her2 in complex with Herceptin (Garrett et al J. Immunology 178:7120 (2007); Cho et al 2003), were incorporated into the lentiviral packaging plasmid epHIV7 and characterized in CHO cells.

In some aspects, utilization of Her2t as a genetic tag allows for the ex vivo selection and purification of homogenous populations of cellular therapeutics that express a transgene of interest. In addition, Her2t can be used to track cellular therapeutics in vivo; for instance, Her2t can be used as a target for Herceptin staining of blood, bone marrow and cerebrospinal fluid aspirates to check for the persistence of transgene-expressing cellular therapeutics to follow cancer remission to therapeutic persistence in a patient. Her2t extends the therapeutic reach of CAR therapy by allowing for the concerted purification of cells expressing multiple transgenes when used with another genetic tag such as EGFRt.

In some alternatives, the disclosure provides an isolated polypeptide comprising at least 95%, 96%, 97%, 98%, or 99% sequence identity to a polypeptide of an extracellular domain of HER2 polypeptide having a sequence of amino acids of 511 to 652 or 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. Nucleic acids coding for the isolated polypeptide are included herein.

In other alternatives, host cells are provided comprising the nucleic acid coding for an isolated polypeptide comprising at least 95%, 96%, 97%, 98%, or 99% sequence identity to a polypeptide of an extracellular domain of HER2 polypeptide having a sequence of amino acids 511 to 562 or 563 to 652 of SEQ ID NO: 23 linked to a transmembrane domain, and wherein the isolated polypeptide specifically binds to an antibody that binds to an epitope in Domain IV of Her2. Host cells can be selected from the group consisting of CD8 T cells, CD4 T cells, CD4 naïve T cells, CD8 naïve T cells, CD8 central memory cells, CD4 central memory cells, and combinations thereof. Host cells can further comprise a second nucleic acid coding for a second chimeric antigen receptor linked to a second genetic tag. In some alternatives, the second nucleic acid can be introduced into the same host cells as a nucleic acid coding for an isolated polypeptide comprising at least 95% sequence identity to a polypeptide of an extracellular domain of HER2 polypeptide having a sequence of amino acids 511 to 562 or 563 to 652 of SEQ ID NO: 23 linked to a transmembrane domain, wherein the isolated polypeptide specifically binds to an antibody that binds to an epitope in Domain IV of Her2. In other alternatives, the second nucleic acid is introduced into a second host cell population and at least the two host cell populations are combined into a single composition. In some alternatives, the T cells comprise precursor T cells. In some alternatives, the precursor T cells are hematopoietic stem cells.

Another aspect of the disclosure provides methods of manufacturing compositions comprising host cells as described herein. In some alternatives, a method comprises introducing an isolated nucleic acid, such as a nucleic acid coding for an isolated polypeptide comprising at least 95%, 96%, 97%, 98%, or 99% sequence identity to a polypeptide of an extracellular domain (ECD) of HER2 polypeptide having a sequence of amino acids 511 to 652 or 563 to 652 of SEQ ID NO: 23 linked to a transmembrane domain, wherein the isolated polypeptide specifically binds to an antibody that binds to an epitope in Domain IV of Her2, into a host cell; and culturing the host cells in a medium comprising at least one growth factor. In some alternatives, a method further comprises selecting the host cells for expression of ECD before or after or both before and after the culturing step. In other alternatives, a method of manufacturing further comprises introducing a second nucleic acid coding for a second chimeric antigen receptor and a second genetic tag into the host cell. In some alternatives, the method further comprises selecting the host cells for expression of the second genetic tag before or after or both before and after the culturing step.

In other alternatives, a method is provided wherein the method comprises introducing a first isolated nucleic acid, such as a nucleic acid coding for an isolated polypeptide comprising at least 95%, 96%, 97%, 98%, or 99% sequence identity to a polypeptide of an extracellular domain of HER2 polypeptide having a sequence of amino acids 511 to 652 or 563 to 652 of SEQ ID NO: 23 linked to a transmembrane domain, wherein the isolated polypeptide specifically binds to an antibody that binds to an epitope in Domain IV of Her2, into a first host cell; selecting first host cells that express ECD, introducing a second nucleic acid coding for a second chimeric antigen receptor and a second genetic tag into a second host cell, selecting second host cells for expression of the second genetic tag, and optionally, culturing the first and second host cells in a medium comprising at least one growth factor. In some alternatives, a composition comprises a first and second host cell population.

Another aspect of the disclosure relates to methods and uses of the compositions for treating cancer, tracking the cells of the composition in vivo, and killing the cells of the composition in vivo. In some alternatives, a method is provided wherein the method comprises treating a patient having cancer and expressing a tumor antigen, wherein the method further comprises administering an effective amount of a composition of host cells comprising one or more nucleic acids coding for a chimeric antigen receptor linked to a genetic tag. In some alternatives, the host cells of the composition comprise a first nucleic acid coding for a first chimeric antigen receptor linked to a first genetic tag and a second nucleic acid coding for a second chimeric antigen receptor linked to a second genetic tag. In some alternatives, the method further comprises administering an antibody or antigen binding fragment thereof that specifically binds to the genetic tag. In some alternatives, an antibody is administered that binds to the first genetic tag, an antibody is administered that specifically binds to the second genetic tag, or both administered. In some alternatives, the antibody is labelled with a detectable label, a cytotoxic agent, or both.

In some alternatives, an isolated polypeptide is provided, wherein the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab.

In some alternatives, an isolated polypeptide is provided, wherein the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab.

In some alternatives, an isolated nucleic acid is provided wherein the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of LEGGGEGRGSLLTCG (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR).

In some alternatives, a host cell is provided wherein the host cell comprises an isolated nucleic acid, wherein the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of L E G G G E G R G S L L T C G (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR). In some alternatives, the host cell is selected from the group consisting of CD8 T cells, CD4 T cells, CD4 naïve T cells, CD8 naïve T cells, CD8 central memory cells, CD4 central memory cells, and combinations thereof. In some alternatives, the host cell is autologous. In some alternatives, the host cell is antigen specific. In some alternatives, the host cells are precursor T cells. In some alternatives, the host cells are hematopoietic stem cells.

In some alternatives, a composition comprising host cells is provided wherein the host cells comprise an isolated nucleic acid, wherein the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of L E G G G E G R G S L L T C G (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR). In some alternatives, the host cell is selected from the group consisting of CD8 T cells, CD4 T cells, CD4 naïve T cells, CD8 naïve T cells, CD8 central memory cells, CD4 central memory cells, and combinations thereof. In some alternatives, the host cell is autologous. In some alternatives, the host cell is antigen specific. In some alternatives, the host cells are precursor T cells. In some alternatives, the host cells are hematopoietic stem cells.

In some alternatives, a method of manufacturing a composition is provided, wherein the method comprises introducing an isolated nucleic acid into a host cell and culturing the host cells in a medium comprising at least one growth factor. In some alternatives, the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of L E G G G E G R G S L L T C G (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR). In some alternatives, the host cell is selected from the group consisting of CD8 T cells, CD4 T cells, CD4 naïve T cells, CD8 naïve T cells, CD8 central memory cells, CD4 central memory cells, and combinations thereof. In some alternatives, the host cell is autologous. In some alternatives, the host cell is antigen specific. In some alternatives, the growth factor is selected from the group consisting of IL-15, IL-7, IL-21, IL-2, and combinations thereof. In some alternatives, the method further comprises selecting cells that express the Her2t polypeptide. In some alternatives, the cells are selected before culturing the cells in the medium. In some alternatives, the cells are selected using an antibody that binds to Domain IV of Her2. In some alternatives, the antibody is trastuzumab. In some alternatives, the method further comprises introducing a second isolated nucleic acid coding for a chimeric antigen receptor linked to a second genetic tag. In some alternatives, the method further comprises selecting cells expressing the second genetic tag. In some alternatives, the second genetic tag comprises EGFRt. In some alternatives, the host cells are precursor T cells. In some alternatives, the host cells are hematopoietic stem cells.

BRIEF DESCRIPTION OF THE DRAWINGS

FIG. 1A depicts a schematic molecular model of the extracellular and transmembrane regions of Her2t (middle) versus Her2 (ErbB2; left). Her2t in complex with Herceptin Fab (right). FIG. 1B depicts a schematic of Her2t containing leader peptide composed of the GMCSF receptor-α chain signal sequence (GMCSFRss) to allow for surface expression. The remaining Her2t sequence is composed of an epitope of Her2 (ErbB2) Domain IV (89 aa) and a 23-aa transmembrane region. FIG. 1C depicts a schematic of Her2t cloned in frame downstream to the CAR and T2A to allow for co-expression.

FIGS. 2A-2D relate to Her2t partners with trastuzumab (Herceptin) to immunomagnetically enrich Her2t-expressing cells. FIG. 2A depicts titration of biotinylated Herceptin against a Her2-expressing cell line. FIG. 2B depicts Her2t-transduced K562 cells pre- and post-selection using biotinylated Herceptin and anti-biotin microbeads (Miltenyi). Cells purified up to 95% Her2t positive. FIG. 2C depicts the epitope of Her2t is specifically recognized by Herceptin and goes unrecognized by commercial Her2t antibodies. FIG. 2D depicts a Western blot analysis using a commercial antibody (top) or biotinylated Herceptin (bottom) exemplifying the difference in kDa size between Her2t (25 kDa) and ErbB2 (250 kDa). Lanes from left to right (1-4): MW ladder, K562 parental, K562 Her2t, K562 ErbB2 (Her2).

FIGS. 3A-3C relate to Her2t is an effective selection marker in concert with EGFRt in central memory T cells (Tcm). FIG. 3A depicts purification of CD8 Tcm from PBMC using a two-step column purification scheme. CD8+ CD45RA− cells are initially selected using a CD8 isolation kit (to enrich for CD8 positive cells) and CD45RA microbeads (to remove CD45RA positive cells). Cells are then positively selected using CD62L microbeads. FIG. 3B depicts CD8 Tcm transduced with CD19CAR-T2A-Her2, CD20CAR-T2A-EGFRt, or both selected using biotinylated Herceptin or Erbitux and anti-biotin microbeads. CD8 Tcm transduced with CD19CAR-T2A-Her2t and CD20CAR-T2A-EGFRt (Both) can be sequentially purified allowing for a dual-specific T cell for CAR therapy. The fifth panel goes with the dual purified Tcm histogram (Both). The top histogram shows Herceptin SA-PE staining (Her2t+) and the bottom histogram shows Erbitux SA-PE staining (EGFRt+) for the dual purified Tcm. FIG. 3C depicts a Western blot analysis using a CD3ζ specific antibody on cell lysates of Her2t or EGFRt purified CD8 Tcm. Lanes from left to right (1-4): MW ladder, Mock transduced, CD19CAR-T2A-Her2t transduced, CD19CAR-T2A-EGFRt transduced. Band intensities demonstrate that while the MFI in (FIG. 3B) is lower for Her2t stained cells, Her2t purified cells have higher transgene expression levels than EGFRt purified cells. Upper bands=CD19CAR; Lower bands=endogenous CD3ζ. A comparison of band intensities between the CAR zeta chain (Upper panel-50 kDa) and the internal zeta chain of the host T Cells (lower panel −15 kDa) shows that the cells expressing CARher2t construct had about 2 fold higher expression of the CAR as compared to the CAREGFRt construct.

FIGS. 4A-4D relate to Her2t and Her2t/EGFRt transduced cells maintain effector phenotype and target specificity. FIG. 4A depicts characterization of K562 target panel left to right: K562 parental, K562 CD19, K562 CD20, and K562 CD19/CD20 (X-axis: CD19+; Y-axis: CD20+). FIG. 4B depicts a 4-hour chromium release assay showing CD19- and CD20-CAR T cell specificity against K562 target panel cells. CD8 Tcm were co-cultured with K562 target cells at a 50:1, 25:1, 12.5:1 or 6.25:1 ratio. Only the dual transduced T cells were able to target all antigen expressing K562 cells. The CD19CAR-T2A-Her2t and CD19CAR-T2A-EGFRt CD8 Tcm demonstrate similar lytic capacity. FIG. 4C depicts a 24-hour cytokine release assay. CD8 Tcm were co-cultured with K562 target cells at a 2:1 T cell-to-target ratio for 24 hours and then supernatant was analyzed for the presence of effector cytokines. CD19CAR-T2A-Her2t transduced CD8 Tcm produced a more diverse repertoire and higher levels of effector cytokines relative to CD19CAR-T2A-EGFRt transduced CD8 Tcm. The panels are the same as A and B (Left to right: K562 parental, K562 CD19, K562 CD20 and K562 CD19/CD20). Similar results were seen for CD4 Tcm (data not shown). FIG. 4D depicts representative fold cytokine production from 24 hr cytokine release assay. CD8 Tcm purified by Her2t (CD19CAR-Her2t) produce significantly higher IL2, IFNγ and TNFα effector cytokine levels when co-cultured with CD19 expressing K562 (above) as compared to CD19CAR-EGFRt. Student's t test p>0.05.

FIGS. 5A-5D relate to use of Her2t as a marker for in vivo detection and fluorescent staining of engineered cells. FIG. 5A depicts CD19CAR-T2A-Her2t or CD19CAR-T2A-EGFRt-expressing CD4 and CD8 Tcm ($10^7$) were injected intravenously into NOD/scid IL-2RγC null mice alongside a subcutaneous injection of $5 \times 10^6$ NSØ-IL15 cells to provide systemic supply of human IL-15. Bone marrow was harvested 14 days post injection and cell suspensions were analyzed by flow cytometry. FIG. 5B depicts three panels showing cells gated for viable (93.6% lymphocytes), single (98.8%), and alive cells (99.9%). (B) CD8 and CD45 staining of left to right (Mock, CD19CAR-T2A-Her2t, CD19CAR-T2A-EGFRt Tcm). At least $1 \times 10^7$ cells were recorded inside of the viable, single cell and alive gates. So although the CD45+ cells represent around 1% of the population, it is equivalent to $1 \times 10^5$ cells. The remaining cells are mouse bone marrow cells. FIG. 5C depicts human CD45+ cells were co-stained with biotinylated Herceptin or Erbitux and SA-APC. Her2t- or EGFRt-expressing Tcm from bone marrow were identified. FIG. 5D depicts TM-LCL parental, Her2(ErbB2) or Her2t expressing cells were adhered to slides using poly-L-lysine and then stained using biotinylated Herceptin and SA-AF647. Staining was only present for cells expressing Her2 or Her2t when stained with biotinylated Herceptin and SA-AF647.

Figure 2A:
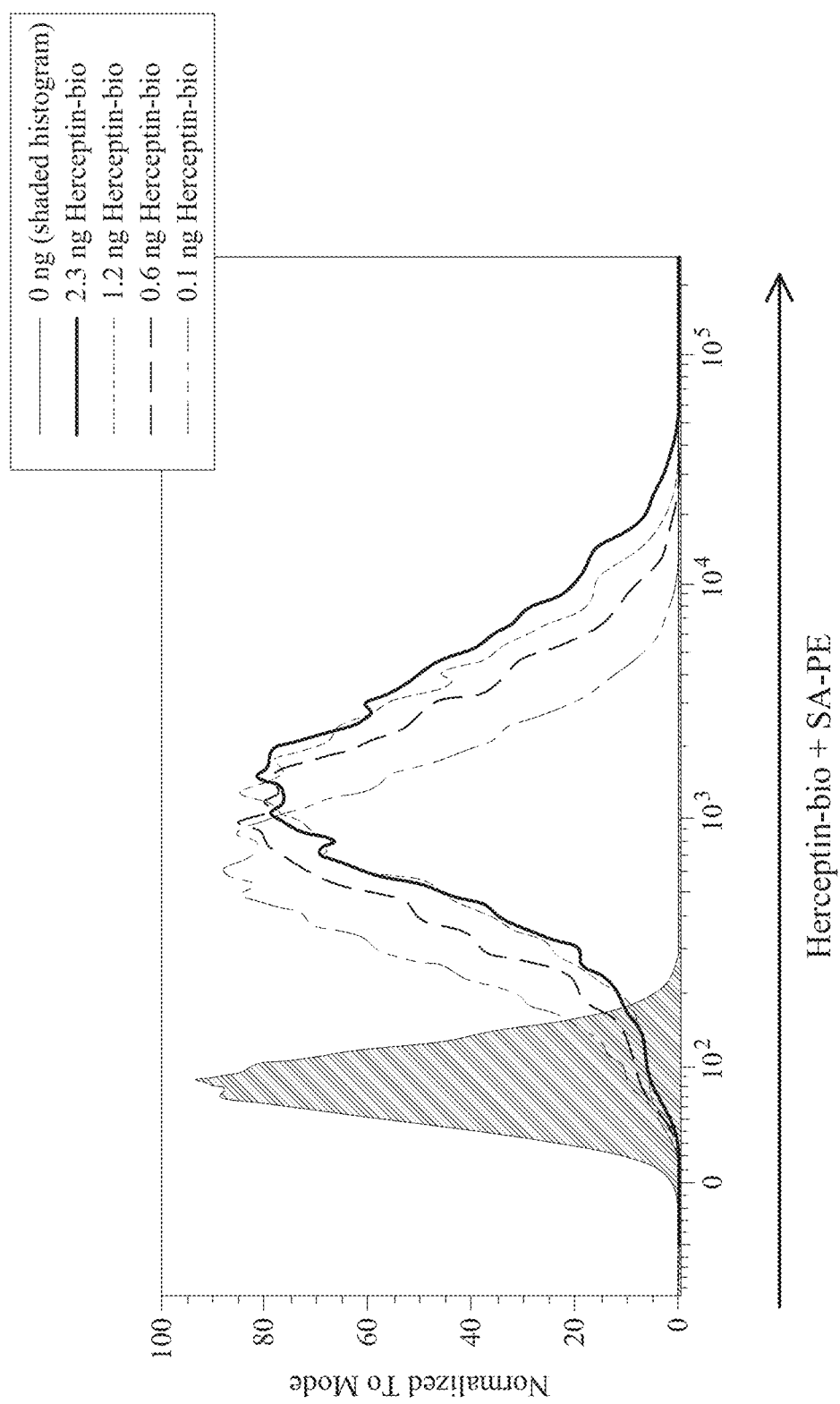

"Naïve" T cells as used herein refers to a non-antigen experienced T lymphocyte that expresses CD62L and CD45RA, and does not express CD45RO– as compared to central or effector memory cells. In some alternatives, naïve CD8+T lymphocytes are characterized by the expression of phenotypic markers of naïve T cells including CD62L, CCR7, CD28, CD127, and/or CD45RA. In some alternatives, a host cell is provided wherein the host cell is antigen specific. In some alternatives, the cell is a naïve T cell.

"Effector" "$T_E$" T cells as used herein, refers to an antigen experienced cytotoxic T lymphocyte cells that do not express or have decreased expression of CD62L, CCR7, and/or CD28, and are positive for granzyme B and/or perforin as compared to central memory or naïve T cells. In some alternatives, a host cell is provided wherein the host cell is antigen specific. In some alternatives, the cell is an effector T cell.

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative ($CD4^-CD8^-$) cells. As they progress through their development, they become double-positive thymocytes ($CD4^+CD8^+$), and finally mature to single-positive ($CD4^+CD8^-$ or $CD4^-CD8^+$) thymocytes that are then released from the thymus to peripheral tissues.

About 98% of thymocytes die during the development processes in the thymus by failing either positive selection or negative selection, whereas the other 2% survive and leave the thymus to become mature immunocompetent T cells.

The double negative (DN) stage of the precursor T cell is focused on producing a functional β-chain whereas the double positive (DP) stage is focused on producing a functional α-chain, ultimately producing a functional αβ T cell receptor. As the developing thymocyte progresses through the four DN stages (DN1, DN2, DN3, and DN4), the T cell expresses an invariant α-chain but rearranges the β-chain locus. If the rearranged β-chain successfully pairs with the invariant α-chain, signals are produced which cease rearrangement of the β-chain (and silence the alternate allele) and result in proliferation of the cell. Although these signals require this pre-TCR at the cell surface, they are dependent on ligand binding to the pre-TCR. These thymocytes will then express both CD4 and CD8 and progresses to the double positive (DP) stage where selection of the α-chain takes place. If a rearranged β-chain does not lead to any signaling (e.g. as a result of an inability to pair with the invariant α-chain), the cell may die by neglect (lack of signaling).

"Hematopoietic stem cells" or "HSC" as described herein, are precursor cells that can give rise to myeloid cells such as, for example, macrophages, monocytes, macrophages, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M).

"Enriched" and "depleted" as used herein to describe amounts of cell types in a mixture, refers to the subjecting of the mixture of the cells to a process or step which results in an increase in the number of the "enriched" type and a decrease in the number of the "depleted" cells. Thus, depending upon the source of the original population of cells subjected to the enriching process, a mixture or composition can contain 60, 70, 80, 90, 95, or 99 percent or more (in number or count) of the "enriched" cells, including any integer between any two endpoints of any of the listed values and 40, 30, 20, 10, 5 or 1 percent or less (in number or count) of the "depleted" cells, including any integer between any two endpoints of any of the listed values.

"Epitope" as used herein refers to a part of an antigen or molecule that is recognized by the immune system including antibodies, T cells, and/or B cells. Epitopes usually have at least 7 amino acids and can be linear or conformational.

"Her2" or "ERBB2" refers to a membrane bound protein kinase receptor that needs a co-receptor for ligand binding. An exemplary polypeptide reference sequence for Her2 is found at Uniprot record P04626 and SEQ ID NO: 23. (Table 8) The full length reference sequence has 1255 amino acids including 1-22 amino acid signal sequence, 23-652 amino acid extracellular domain, 653-675 amino acid transmembrane domain, and 676-1255 amino acid cytoplasmic domain as shown in Table 8. The full length mature polypeptide sequence has 1233 amino acids as the leader sequence is not included in the mature polypeptide. A number of naturally occurring variants and isoforms are known. A nucleic reference sequence is found at Genbank X03363/gI 31197. The extracellular domain has 4 regions that correspond to: Domain I amino acids 23-217; domain II amino acids 218 to 341; domain III amino acids 342 to 510; and Domain IV amino acids 511 to 562 of SEQ ID NO: 23.

"Her2t" refers to a fragment of the sequence of Her2, and is useful as a genetic tag for transgene expression. In some alternatives, Her2t comprises domain IV of the extracellular domain of Her2 and excludes full length Her2. In some alternatives, Her2t specifically binds to an antibody specific for Domain IV of Her2. In other alternatives, Her2t comprises amino acids 511 to 562 or 563-652 of SEQ ID NO: 23.

"Isolated," is used to describe the various polypeptides disclosed herein, and means polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and can include enzymes, hormones, and other proteinaceous or non-proteinaceous solutes.

"Intracellular signaling domain" as used herein refers to all or a portion of one or more domains of a molecule (here the chimeric receptor molecule) that provides for activation of a lymphocyte. Intracellular domains of such molecules mediate a signal by interacting with cellular mediators to result in proliferation, differentiation, activation and other effector functions. In some alternatives, such molecules include all or portions of CD28, CD3, and/or 4-1BB, or combinations thereof.

"Ligand" as used herein refers to a substance that binds specifically to another substance to form a complex. Examples of ligands include epitopes on antigens, molecules that bind to receptors, substrates, inhibitors, hormones, and activators. "Ligand binding domain" as used herein refers to a substance or portion of a substance that binds to a ligand.

Examples of ligand binding domains include antigen binding portions of antibodies, extracellular domains of receptors, and active sites of enzymes.

"Operably linked" as used herein, refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary, it is to join two protein coding regions, in the same reading frame.

"Percent (%) amino acid sequence identity" with respect to the genetic tag polypeptide sequences identified herein, is defined as the percentage of amino acid residues in a candidate sequence that are identical with the amino acid residues in the reference sequence after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program [Altschul et al., Methods in Enzymology, 266:460-480 (1996)] uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between each or all of the polypeptide amino acid sequence of the reference Her2 sequence provided in SEQ ID NO: 15 or amino acids 563-652 of SEQ ID NO: 23 and the comparison amino acid sequence of interest as determined by WU-BLAST-2 by (b) the total number of amino acid residues of the polypeptide of interest.

"Genetic tag variant polynucleotide" as used herein refers to a polypeptide-encoding nucleic acid molecule as defined below having at least about 80% nucleic acid sequence identity with the polynucleotide acid sequence shown in SEQ ID NO: 15 or nucleotides or a specifically derived fragment thereof. Ordinarily, a variant of polynucleotide or fragment thereof will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with the nucleic acid sequence as shown in SEQ ID NO: 14 or a derived fragment thereof, or any percent nucleic acid sequence identity between any two of the values of percent nucleic acid sequence identity listed. Variants do not encompass the native nucleotide sequence. In this regard, due to the degeneracy of the genetic code, one of ordinary skill in the art will immediately recognize that a large number of chimeric receptor variant polynucleotides having at least about 80% nucleic acid sequence identity to the nucleotide sequence of SEQ ID No: 14 or nucleotides that encodes a polypeptide having an amino acid sequence of SEQ ID NO: 18.

"Substantially purified" refers to a molecule that has 10%, 9%, 8%, 7%, 6%, 5%, 4%, 3%, 2%, or 1% or less other molecule types or other cell types, or any value between any two of the percent purification values listed. A substantially purified cell also refers to a cell, which has been separated from other cell types with which it is normally associated in its naturally occurring state. In some instances, a population of substantially purified cells refers to a homogenous population of cells.

"Not substantially found" when used in reference the presence of a tumor antigen or other molecules on normal cells refers to the percentage of a normal cell type that has the antigen or molecule, and/or the density of the antigen on the cells. In some alternatives, not substantially found means that the antigen or molecule is found on less than 50% of normal cell type and/or at a 50% less density as compared to the amount of cells or antigen found on a tumor cell or other diseased cell.

"T cells" or "T lymphocytes" as used herein can be from any mammalian, preferably primate, species, including monkeys, dogs, and humans. In some alternatives, the T cells are allogeneic (from the same species but different donor) as the recipient subject; in some alternatives, the T cells are autologous (the donor and the recipient are the same); in some alternatives, the T cells arc syngeneic (the donor and the recipients are different but are identical twins).

"Vector" or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes.

DETAILED DESCRIPTION

This disclosure provides for a genetic tag polypeptide or variant thereof and a nucleic acid coding for the genetic tag useful to provide a selection marker and/or an identification marker for transgene expressing cells.

Transgene Genetic Tag and Polypeptides and Variants.

One aspect of the disclosure provides a genetic tag for transgene expression that provides stable expression of the transgene expression in cells. In some alternatives, the genetic tag provides for selection of transduced cells that express the transgene at levels comparable to endogenous genes. In some alternatives, the genetic tag is expressed on the cell surface, has decreased immunogenicity, does not substantially increase the genetic payload in a vector, and/or provides for transgene expression in a variety of cells.

In some alternatives, the genetic tag is a fragment of Her2 designated as Her2t that at least includes an epitope recognized by an anti-Her2 antibody. In some alternatives, the antibody specifically binds to Domain IV of Her2. In other alternatives, the antibody specifically binds to Domain IV of Her2 and does not bind to epitopes in domains I, II, and/or III of Her2. In some alternatives, the anti-Her2 antibody is an antibody therapeutically useful for treating cancer. In some alternatives, the epitope is recognized by trastuzumab (Herceptin). In some alternatives, the epitope is recognized by trastuzumab and/or antibodies that compete for binding with trastuzumab but no other anti-Her2 antibodies that bind for example, to epitopes in domains I, II, and/or III of Her2.

In a specific alternative, the epitope includes amino acids as determined by the crystal structure of Her2 in complex with Herceptin Fab (Cho et al., Nature (2003) 421:756). The interaction between Her2 and Herceptin occurs between three loop regions (two electrostatic and one hydrophobic) in Domain IV. Key interactive amino acids in HER2 towards Herceptin are as follows: loop 1 (electrostatic), which includes amino acid sequence 580-584 EADQC (including Glu 580 and Asp 582) (SEQ ID NO: 42), loop 2 (hydrophobic) which includes amino acid sequence 592-595 DPPF (including Asp 592 and Phe 595) (SEQ ID NO: 43), and loop 3 (electrostatic) which includes amino acid sequence 616-625 FPDEEGACQP (Including Gln 624) (SEQ ID NO: 44) (aa numbering system is based off of the entire ErbB2(Her2) sequence of SEQ ID NO:23, including the signaling sequence and as shown in Table 8). Using the numbering system of Cho et al. which removes the 22aa from the signal sequence resulting in the following amino acids of HER2 involved with Herceptin: loop 1 Glu 558 and Asp 560, loop 2 Asp 570 and Phe 573, and loop 3 Gln 602. In some alternatives, a fragment of Her2 contains at least these amino acid residues and is further selected for binding to trastuzumab or an antibody that competes for binding with trastuzumab when expressed on a cell surface. While not meant to limit the scope of the disclosure, it is believed that a Her2t fragment containing at least amino acids 563-652 includes an epitope that can bind trastuzumab as a smaller epitope containing amino acids 578 to 652 did not bind to trastuzumab. In some alternatives, the Her2t fragment comprises the amino acids 563-652 of Her2t. In some alternatives, the Her2t fragment comprises the amino acid sequences 580-584 of Her2t, amino acid sequences 592-595 of Her2t and amino acid sequences 616-625 of Her2t.

In a specific alternative, a fragment of Her2 comprises, consists essentially of, or consists of amino acids 511-652 (Domain IV) or 563-652 as shown in Table 6 (SEQ ID NO:18). In some alternatives, a variant of the Her2 fragment has at least 90%, 91%, 92%, 93%, 94%, 95%, 96%, 97%, 98%, or 99% sequence identity with the sequence of SEQ ID NO:18 or a percentage sequence identity that is between a range defined by any two of the aforementioned percentages, and when expressed on the cell surface binds to trastuzumab. In some alternatives, the variant fragment has at least 9, 8, 7, 6, 5, 4, 3, 2, or 1 amino acid substitutions, preferably conservative amino acid substitutions. Such substitutions can be identified using the crystal structure of Her2 in complex with Herceptin Fab (Cho et al., Nature (2003)). In some alternatives, the variant fragment does not include amino acid substitution in the residues involved in binding to trastuzumab as described herein. In some alternatives, the fragment includes residues in Domain IV of Her2 and excludes one or more other domains of Her2 including domain 1, domain II, domain III, and/or intracellular domains.

In some alternatives, the genetic tag generates little or no immune response. In some alternatives, a genetic tag is selected from endogenously occurring proteins in order to take advantage of the subject's tolerance to endogenous proteins. In some alternatives, the genetic tag is analyzed with software for predicting antigenic epitopes such as MHC-I antigenic peptide processing prediction algorithm. A sequence: MLLLVTSLLLCELPHPAFLLIPCHPECQPQNGSVT (SEQ ID NO: 16) is analyzed for antigenic determinants. In some alternatives, the nucleic acid sequence of the genetic tag is derived from and/or modified from the germ line sequence for incorporation in an artificial or synthetic transgene construct.

In some alternatives, a genetic tag further includes a transmembrane domain. The transmembrane domain can be derived either from a natural or a synthetic source. When the source is natural, the domain can be derived from any membrane-bound or transmembrane protein. Transmembrane regions comprise at least the transmembrane region(s) of) the alpha, beta or zeta chain of the T-cell receptor, CD28, CD3, CD45, CD4, CD8, CD9, CD16, CD22; CD33, CD37, CD64, CD80, CD86, CD134, CD137 and/or CD154. In a specific alternative, the transmembrane domain comprises the amino acid sequence of the Her2 transmembrane domain as shown in Table 6 (e.g. amino acids 653-675 (SEQ ID NO: 20). A representative polynucleotide sequence coding for the Her2 transmembrane domain (SEQ ID NO: 19) is shown in Table 6.

In some alternatives, synthetic or variant transmembrane domains comprise predominantly hydrophobic residues, such as leucine and valine. In some alternatives, a transmembrane domain can have at least 80%, 85%, 90%, 95%, or 100% amino acid sequence identity with a transmembrane domain as shown in Table 6 or percentage sequence identity that is between a range defined by any two of the aforementioned percentages. Variant transmembrane domains preferably have a hydrophobic score of at least 50 as calculated by Kyte Doolittle.

In some alternatives, a genetic tag includes a peptide that enhances surface expression of the genetic tag. Such peptides include, for example, including the granulocyte macrophage stimulating factor signal sequence, endogenous Her2 leader peptide (aa 1-22), type I signal peptides, IgGκ signal peptide, and/or CD8 leader sequence. In some alternatives, the leader sequence has a sequence of SEQ ID NO: 17.

In a specific alternative, a genetic tag comprises a fragment of Her2 that binds trastuzumab, and a transmembrane domain as exemplified by SEQ ID NO: 20. In another specific alternative, a genetic tag comprises a peptide that enhances surface expression, a fragment of Her2 that binds trastuzumab, and a transmembrane domain as exemplified by SEQ ID NO: 15. In some alternatives, a variant of the genetic tag has 90%, 91%, 92%, 93%, 94%, 95%, 96%, 97%, 98%, or 99% sequence identity with the sequence of SEQ ID NO:16 or SEQ ID NO:20 or a percentage sequence identity that is between a range defined by any two of the aforementioned percentages, and when expressed on the cell surface binds to trastuzumab. In some alternatives, the variant fragment has at least 9, 8, 7, 6, 5, 4, 3, 2, or 1 amino acid substitutions, preferably conservative amino acid substitutions. In some alternatives, the variant fragment does not include amino acid substitution in the residues involved in binding to trastuzumab.

Optionally, a linker sequence can precede the genetic tag sequence and/or separate one or more functional domains (e.g. peptide to enhance surface expression, genetic tag, transmembrane domain) of the genetic tag. Linker sequences are optionally cleavable, for example, T2A sequences (as shown in Table 1) or IRES sequences. Cleavable linker sequences are typically placed to precede the genetic tag sequence in a nucleic acid construct. Other linker sequences are typically short peptides, of about 2 to 15 amino acids and are located between functional domains of the genetic tag including the peptide to enhance surface expression, genetic tag, and transmembrane domain. In some alternatives, the linkers are between 2, 3, 4, 5, 6, 7, 8, 9, 10, 11, 12, 13, 14 or 15 amino acids and are located between functional domains of the genetic tag including the peptide to enhance surface expression, genetic tag, and transmembrane domain. In some alternatives the linker is a cleavable linker. In some alternatives the linker is a cleavable T2A sequence. In some alternatives, the linker comprises IRES sequences.

In some alternatives, the system further comprises one or more additional genetic tags. In an alternative, the additional genetic tag sequence is a fragment of an epidermal growth factor receptor (EGFRt) sequence. An example of such a sequence is provided in Table 7. Typically a genetic tag sequence has a functional characteristic that allows for selection of transduced cells and/or detection of transduced cells. In some alternatives, the genetic tag sequence is compatible with transduction of human lymphocytes.

In other alternatives, an additional genetic tag is a positive selectable marker. A positive selectable genetic tag can be a gene, which upon being introduced into the host cell, expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene which provides resistance to methotrexate, DHFR dm, the pac gene that provides resistance to puromycin, Sh ble gene which inactivates zeocin, the adenosine deaminase gene (ADA), and the multi-drug resistance (MDR) gene. Transduced cells cultured in the presence of these agents will survive and be selected. In some alternatives, the host cells are precursor T cells. In some alternatives, the host cells are hematopoietic stem cells.

In an alternative, a first nucleic acid further comprises a polynucleotide coding for a genetic tag sequence. In some alternatives, the genetic tag sequence is a Her2t sequence. An exemplary polynucleotide and amino acid for the Her2t sequences is shown in Table 6 and provided by SEQ ID NO:14 and SEQ ID NO:15, respectively. In an alternative, the genetic tag sequence is an epidermal growth factor receptor fragment (EGFRt) as shown in Table 7. An exemplary polynucleotide for the truncated epidermal growth factor receptor is SEQ ID NO: 22.

A polynucleotide coding for genetic tag can be readily prepared by synthetic or recombinant methods from the amino acid sequence. In some alternatives, a polynucleotide coding for a genetic tag sequence is operably linked to a polynucleotide coding for a linker sequence. In some alternatives, the polynucleotide coding for a genetic tag sequence can also have one or more restriction enzyme sites at the 5' and/or 3' ends of the coding sequence in order to provide for easy excision and replacement of the polynucleotide coding for a tag sequence with another polynucleotide coding for a different genetic tag sequence. In some alternatives, the polynucleotide coding for a marker sequence is codon optimized for expression in mammalian cells, preferably humans.

In some alternatives, two or more genetic tag sequences can be employed. In some alternatives, a first genetic tag sequence is operably linked to a first chimeric antigen receptor and provides for an indication that the transduced cell is expressing the first CAR. In other alternatives, a second genetic tag sequence is operably linked to a second and different CAR and provides an indication that the transduced cell is expressing the second CAR.

Nucleic Acids, and Vectors.

Another aspect of the disclosure includes nucleic acid constructs and variants thereof coding for the genetic tags as described herein.

In some alternatives, a nucleic acid codes for an amino acid sequence of a fragment Her2 or a variant thereof. In a specific alternative, a nucleic acid codes for a polypeptide having an amino acid sequence of SEQ ID NO: 18. In a specific alternative, a nucleic acid codes for a polypeptide having an amino acid sequence of SEQ ID NO: 15. In an alternative, the genetic tag sequence is an epidermal growth factor receptor fragment (EGFRt) as shown in Table 7. An exemplary polynucleotide for the truncated epidermal growth factor receptor is SEQ ID NO: 21. Nucleic acids include nucleic acid sequences that are codon optimized for expression in humans, degenerate sequences, and variant sequences.

Vectors.

In some alternatives, a vector comprises a nucleic acid coding for a genetic tag. A nucleic acid coding for a genetic tag can be packaged in a vector as a separate construct or linked to a nucleic acid coding for a transgene. In some alternatives, a nucleic acid coding for a genetic tag is packaged in a vector as a separate construct or linked to a nucleic acid coding for a transgene A variety of vector combinations can be constructed to provide for efficiency of transduction and transgene expression. In some alternatives, the vector is a dual packaged or single (all in one) viral vector. In other alternatives, the vectors can include a combination of viral vectors and plasmid vectors. Other viral vectors include foamy virus, adenoviral vectors, retroviral vectors, and lentiviral vectors. In alternatives, the vector is a lentiviral vector.

In some alternatives, a plasmid vector or a viral vector comprises a nucleic acid comprising a polynucleotide coding for a genetic tag. In some alternatives, the genetic tag comprises a polynucleotide coding for Her2t, and further comprises a promoter, a polynucleotide coding for a peptide to enhance surface expression and/or a polynucleotide coding for a transmembrane domain. In a specific alternative, the first nucleic acid codes for a polypeptide having a sequence of SEQ ID NO: 18 or SEQ ID NO: 20 or SEQ ID NO: 15 or variant thereof operably linked to a promoter.

In some alternatives, a plasmid or viral vector comprises a promoter operably linked to a polynucleotide coding for a chimeric antigen receptor operably linked to a polynucleotide coding for a genetic tag. In some alternatives, the chimeric antigen receptor is directed to CD19 or CD20 and the genetic tag comprises Her2t fragment. In some alternatives, the polynucleotide coding for the CAR is operably linked to the genetic tag with a self-cleavable linker. In other alternatives, a plasmid or viral vector comprises a promoter operably linked to a polynucleotide coding for a CD19 chimeric antigen receptor operably linked to a polynucleotide coding for Her2t or EGFRt. In other alternatives, a plasmid or viral vector comprises a promoter operably linked to a polynucleotide coding for a CD20 chimeric antigen receptor operably linked to a polynucleotide coding for Her2t or EGFRt.

Each element of the nucleic acid can be separated from one another with a linker sequence, preferably, a self-cleaving linker such as a T2A self-cleaving sequence.

In other alternatives, the heterogeneous (heterogeneous to the vector, e,g, lentiviral vector) nucleic acid sequence is limited by the amount of additional genetic components that can be packaged in the vector. In some alternatives, a construct contains at least two genes heterogenous to the viral vector. In some alternatives, the construct contains no more than 4 genes heterogenous to the viral vector. The number of genes heterogenous to the viral vector that can be packaged in the vector can be determined by detecting the expression of one or more transgenes, and selecting vector constructs that provide for transduction of at least 10% of the cells and/or detectable expression levels of the transgene in at least 10% of the cells.

In some alternatives, a lentivirus is a dual packaged virus. A dual packaged virus contains at least one nucleic acid comprising a polynucleotide coding for a chimeric antigen receptor and a first genetic tag. Optionally the nucleic acid further comprises a polynucleotide coding for a cytokine, and/or a chemokine receptor. A dual packaged virus contains at least one nucleic acid comprising a polynucleotide coding for a chimeric antigen receptor and a second genetic tag. Optionally the nucleic acid further comprises a polynucleotide coding for a cytokine, and/or a chemokine receptor. In some alternatives of a system with two constructs, each construct can be packaged in a separate viral vector and the viral vectors can be mixed together for transduction in a cell population. In some alternatives, the first and second genetic tags are different from one another.

In some alternatives, the dual packaged virus provides for expression of at least two different transgenes, (e.g. CAR constructs) in a single cell type. Using different genetic tags provides for selection of dual transduced cells. In a specific alternative, a plasmid or viral vector comprises a promoter operably linked to a polynucleotide coding for a CD19 chimeric antigen receptor operably linked to a polynucleotide coding for Her2t. In other alternatives, the plasmid or viral vector further comprises a promoter operably linked to a polynucleotide coding for a CD20 chimeric antigen receptor operably linked to a polynucleotide coding for EGFRt.

In some alternatives, the vector is a minicircle. Minicircles are episomal DNA vectors that are produced as circular expression cassettes devoid of any bacterial plasmid DNA backbone. Their smaller molecular size enables more efficient transfections and offers sustained expression over a period of weeks as compared to standard plasmid vectors that only work for a few days. In some alternatives, a minicircle comprises a promoter linked to a polynucleotide coding for a chimeric antigen receptor operably linked to a genetic tag. One or more minicircles can be employed. In some alternatives, a minicircle comprises a promoter linked to a polynucleotide coding for a chimeric antigen receptor and first genetic tag, another minicircle comprises a promoter linked to a polynucleotide coding for a chimeric antigen receptor and a second and different genetic tag. In some alternatives, each element of the constructs is separated by a nucleic acid, such as one coding for a self-cleaving T2A sequence. In some alternatives, each minicircle differs from one another in the chimeric antigen receptor including but not limited to the spacer length and sequence, the intracellular signaling domain, and/or the genetic tag sequence.

In some alternatives, the vector is a PiggyBac transposon. The PiggyBac (PB) transposon is a mobile genetic element that efficiently transposes between vectors and chromosomes via a "cut and paste" mechanism. During transposition, the PB transposase recognizes transposon-specific inverted terminal repeat sequences (ITRs) located on both ends of the transposon vector and efficiently moves the contents from the original sites and efficiently integrates them into TTAA chromosomal sites. The powerful activity of the PiggyBac transposon system enables genes of interest between the two ITRs in the PB vector to be easily mobilized into target genomes.

In some alternatives, a PB contains a promoter linked to a polynucleotide coding for a chimeric antigen receptor operably linked to a genetic tag. One or more PB transposons can be employed. In some alternatives, a PB comprises a promoter linked to a polynucleotide coding for a chimeric antigen receptor and a first genetic tag, another PB comprises a promoter linked to a polynucleotide coding for a chimeric antigen receptor, and a second and different genetic tag. Each element of the constructs is separated by a nucleic acid, such as that coding for a self-cleaving T2A sequence. In some alternatives, each PB differs from one another in the chimeric antigen receptor including but not limited to the spacer length and sequence, the intracellular signaling domain, and/or the genetic tag sequence.

In some alternatives, a first nucleic acid comprises a first promoter operably linked to a polynucleotide coding for chimeric antigen receptor comprising a ligand binding domain, wherein the ligand binding domain binds to a ligand, wherein the ligand is a tumor specific molecule, viral molecule, or any other molecule expressed on a target cell population that is suitable to mediate recognition and elimination by a lymphocyte; a polynucleotide coding for a polypeptide spacer, wherein the spacer provides for increased T cell proliferation and/or cytokine production in response to the ligand as compared to a reference chimeric receptor; a polynucleotide coding for a transmembrane domain; and d) a polynucleotide coding for an intracellular signaling domain. In some alternatives, the first nucleic acid further comprises a genetic tag.

In some alternatives, a second nucleic acid comprises a polynucleotide coding for a second and different chimeric antigen receptor. The first and second chimeric antigen receptor can differ from one another in the ligand binding domain, the target antigen, an epitope of the target antigen, the spacer domain in length and sequence (short medium or long), and in the intracellular signaling domains. In some alternatives, the second nucleic acid further comprises a second and different genetic tag from that of the first nucleic acid.

In some alternatives, in a single lentivirus construct the first and second nucleic acids can be separated by a genomic insulator nucleic acid such as the sea urchin insulator chromatin domain.

In some alternatives, promoters used herein can be inducible or constitutive promoters. Inducible promoters include a tamoxifen inducible promoter, tetracycline inducible promoter, and doxocycline inducible promoter (e.g. tre) promoter. Constitutive promoters include SV40, CMV, UBC, EF1alpha, PGK, and CAGG.

One or more of these vectors can be used in conjunction with one another to transduce target cells and provide for expression of a chimeric antigen receptor.

Transgenes.

Several transgenes are also aspects of the invention.

The genetic tags as described herein are useful for the selection, tracking, and killing of cells transduced with and expressing a transgene. The genetic tags can be utilized with any number of different transgenes. In this disclosure, chimeric antigen receptor transgenes are exemplified but similar principals apply to the design, identification and selection of other transgenes expressed in transduced cells.

Chimeric Antigen Receptors.

Several chimeric antigen receptors can be utilized in the alternatives described herein.

A system for expression of chimeric antigen receptor comprises: a first nucleic acid comprising a first promoter linked to a polynucleotide coding for a chimeric antigen receptor, the chimeric antigen receptor comprising a ligand binding domain, wherein the ligand binding domain binds to a ligand, wherein the ligand is a tumor specific molecule, viral molecule, or any other molecule expressed on a target cell population that is suitable to mediate recognition and elimination by a lymphocyte; a polynucleotide coding for a polypeptide spacer, wherein the spacer provides for increased T cell proliferation and/or cytokine production in response to the ligand as compared to a reference chimeric receptor; a polynucleotide coding for a transmembrane domain; and d) a polynucleotide coding for an intracellular signaling domain. In other alternatives, another polynucleotide coding for a chimeric antigen receptor is under the control of a constitutive promoter.

Ligand Binding Domain.

Many ligand binding domains can be utilized in the alternatives described herein.

In some alternatives, the chimeric receptor nucleic acid comprises a polynucleotide coding for a ligand binding domain. In some alternatives, the ligand binding domain specifically binds to a tumor or viral specific antigen. In some alternatives, a ligand binding domain, includes without limitation, receptors or portions thereof, small peptides, peptidomimetics, substrates, cytokines, and the like. In some alternatives, the ligand binding domain is an antibody or fragment thereof. A nucleic acid sequence coding for an antibody or antibody fragment can readily be determined. In a specific alternative, the polynucleotide codes for a single chain Fv that specifically binds CD19. In other specific some alternatives, the polynucleotide codes for a single chain Fv that specifically binds CD20, HER2, CE7, hB7H3, or EGFR. The sequences of these antibodies are known to or can readily be determined by those of skill in the art.

Tumor antigens are proteins that are produced by tumor cells that elicit an immune response. The selection of the ligand binding domain of the disclosure will depend on the type of cancer to be treated, and can target tumor antigens or other tumor cell surface molecules. A tumor sample from a subject can be characterized for the presence of certain biomarkers or cell surface markers. For example, breast cancer cells from a subject can be positive or negative for each of Her2Neu, Estrogen receptor, and/or the Progesterone receptor. A tumor antigen or cell surface molecule is selected that is found on the individual subject's tumor cells. Tumor antigens and cell surface molecules are well known in the art and include, for example, carcinoembryonic antigen (CEA), prostate specific antigen, PSMA, Her2/neu, estrogen receptor, progesterone receptor, ephrinB2, CD19, CD171, EGFR, CD20, CD22, CD23, CD123, CS-1, CE7, hB7H3, ROR1, mesothelin, c-Met, GD-2, and/or MAGE A3 TCR. In some alternatives a target molecule is a cell surface molecule that is found on tumor cells and is not substantially found on normal tissues, or restricted in its expression to non-vital normal tissues.

In one alternative, the target molecule on the tumor comprises one or more epitopes associated with a malignant tumor. Malignant tumors express a number of proteins that can serve as target antigens for T cell receptor or chimeric receptor mediated recognition. Other target molecules belong to the group of cell transformation-related molecules such as CD19 or CD20. In some alternatives, the tumor antigen is selectively expressed or overexpressed on the tumor cells as compared to control cells of the same tissue type. In other alternatives, the tumor antigen is a cell surface polypeptide.

Once a tumor cell surface molecule that might be targeted with a chimeric receptor is identified, an epitope of the target molecule is selected and characterized. Antibodies that specifically bind a tumor cell surface molecule can be prepared using methods of obtaining monoclonal antibodies, methods of phage display, methods to generate human or humanized antibodies, or methods using a transgenic animal or plant engineered to produce human antibodies. Phage display libraries of partially or fully synthetic antibodies are available and can be screened for an antibody or fragment thereof that can bind to the target molecule. Phage display libraries of human antibodies are also available. In some alternatives, antibodies specifically bind to a tumor cell surface molecule and do not cross react with nonspecific components such as bovine serum albumin or other unrelated antigens. Once identified, the amino acid sequence or polynucleotide sequence coding for the antibody can be isolated and/or determined. In some alternatives, phage display libraries of partially or fully synthetic antibodies are screened for an antibody or fragment thereof that can bind to a target molecule.

Antibodies or antigen binding fragments include all or a portion of polyclonal antibodies, a monoclonal antibody, a human antibody, a humanized antibody, a synthetic antibody, a chimeric antibody, a bispecific antibody, a minibody, and a linear antibody. Antibody fragments" comprise a portion of an intact antibody, preferably the antigen binding or variable region of the intact antibody and can readily be prepared. Examples of antibody fragments include Fab, Fab', F(ab')2, and Fv fragments; diabodies; linear antibodies; single-chain antibody molecules; and multispecific antibodies formed from antibody fragments.

In some alternatives, a number of different antibodies that bind to particular tumor cell surface molecules can be isolated and characterized. In some alternatives, the antibodies are characterized based on epitope specificity of the targeted molecule. In addition, in some alternatives, antibodies that bind to the same epitope can be selected based on the affinity of the antibody for that epitope. In some alternatives, an antibody has an affinity of at least 1 mM, and preferably <50 nM. In some alternatives, an antibody is selected that has a higher affinity for the epitope as compared to other antibodies. For example, an antibody is selected that has at least a 2 fold, at least a 5 fold, at least a 10 fold, at least a 20 fold, at least a 30 fold, at least a 40 fold, or at least a 50 fold greater affinity than a reference antibody that binds to the same epitope. In some alternatives, an antibody is selected that has at least a 2 fold, at least a 5 fold, at least a 10 fold, at least a 20 fold, at least a 30 fold, at least a 40 fold, or at least a 50 fold greater affinity, than a reference antibody that binds to the same epitope or any value of greater affinity between any of the defined values listed.

In some alternatives, target molecules are selected from CD19, CD20, CD22, CD23, CE7, hB7H3, EGFR, CD123, CS-1, ROR1, mesothelin, Her2, c-Met, PSMA, GD-2, and/or MAGE A3 TCR and combinations thereof. In some alternatives, when a Her2 CAR construct is desired, the genetic tag comprises an epitope that does not bind to the scFv for Her2 used in the CAR construct. In some alternatives, when a EGFR CAR construct is desired, the genetic tag comprises an epitope that does not bind to the scFv for EGFR used in the CAR construct.

In specific alternatives, the target antigen is CD19. A number of antibodies specific for CD19 are known to those of skill in the art and can be readily characterized for sequence, epitope binding, and affinity. In a specific alternative, the chimeric receptor construct includes a scFV sequence from FMC63 antibody. In other alternatives, the scFV is a human or humanized ScFv comprising a variable light chain comprising a CDRL1 sequence of RASQDISKYLN (SEQ ID NO: 27), CDRL2 sequence of SRLHSGV (SEQ ID NO:28), and a CDRL3 sequence of GNTLPYTFG (SEQ ID NO: 29). In other alternatives, the scFV is a human or humanized ScFv comprising a variable heavy chain comprising CDRH1 sequence of DYGVS (SEQ ID NO: 30), CDRH2 sequence of VIWGSETTYYNSALKS (SEQ ID NO: 31), and a CDRH3 sequence of YAMDY (SEQ ID NO: 32). The disclosure also contemplates variable regions that have at least 90%, 91%, 92%, 93%, 94%, 95%, 96%, 97%, 98%, or 99% amino acid sequence identity to that of the scFv for FMC63 or a percentage sequence identity that is between a range defined by any two of the aforementioned percentages and that have at least the same affinity for CD19.

In some alternatives, CDR regions are found within antibody regions as numbered by Kabat as follows: for the light chain; CDRL1 amino acids 24-34; CDRL2 amino acids 50-56; CDRL3 at amino acids 89-97; for the heavy chain at CDRH1 at amino acids 31-35; CDRH2 at amino acids 50-65; and for CDRH3 at amino acids 95-102. CDR regions in antibodies can be readily determined.

In specific alternatives, the target antigen is CD20. A number of antibodies specific for CD20 are known to those of skill in the art and can be readily characterized for sequence, epitope binding, and affinity. In a specific alternative, the chimeric receptor construct includes a scFV sequence as shown in Table 9. In other alternatives, the scFV is a human or humanized ScFv comprising a variable light chain comprising a CDRL1 sequence of R A S S S V N Y M D (SEQ ID NO: 33), CDRL2 sequence of A T S N L A S (SEQ ID NO: 34), and a CDRL3 sequence of Q Q W S F N P P T (SEQ ID NO: 35). In other alternatives, the scFV is a human or humanized ScFv comprising a variable heavy chain comprising CDRH1 sequence of S Y N M H (SEQ ID NO: 36), CDRH2 of A I Y P G N G D T S Y N Q K F K G (SEQ ID NO: 37), and a CDRH3 sequence of S N Y Y G S S Y W F F D V (SEQ ID NO: 38). The CDR sequences can readily be determined from the amino acid sequence of the scFv. The disclosure also contemplates variable regions that have at least 90%, 91%, 92%, 93%, 94%, 95%, 96%, 97%, 98%, or 99% amino acid sequence identity to that of the scFv for CD20 or a percentage sequence identity that is between a range defined by any two of the aforementioned percentages and that have at least the same affinity for CD20.

In some alternatives, a polynucleotide coding for a ligand binding domain is operably linked to a polynucleotide coding for a spacer region. In some alternatives, the polynucleotide coding for a ligand binding domain can also have one or more restriction enzyme sites at the 5' and/or 3' ends of the coding sequence in order to provide for easy excision and replacement of the polynucleotide with another polynucleotide coding for a ligand binding domain coding for a different antigen or that has different binding characteristics. For example, a restriction site, NheI, is encoded upstream of the leader sequence; and a 3' RsrII located within the hinge region allows sub-cloning of any desirable scFv into a chimeric receptor vector. In some alternatives, the polynucleotide is codon optimized for expression in mammalian cells. In some alternatives, the polynucleotide is codon optimized for expression in human cells.

In some alternatives, the polynucleotide coding for a ligand binding domain is operably linked to a signal peptide. In some alternatives the signal peptide is a signal peptide for granulocyte colony stimulating factor. Polynucleotides coding for other signal peptides such as CD8 alpha can be utilized.

In some alternatives, the polynucleotide coding for a ligand binding domain is operably linked to a promoter. A promoter is selected that provides for expression of the chimeric antigen receptor in a mammalian cell. In a specific alternative the promoter is an inducible promoter.

A specific alternative of a polynucleotide coding for a ligand binding domain is shown in Table 1 as the scFv from an antibody that specifically binds CD19, such as FMC63. A polynucleotide encoding for a flexible linker including the amino acids GSTSGSGKPGSGEGSTKG (SEQ ID NO: 39) separates the VH and VL chains in the scFV. The amino acid sequence of the scFv including the linker is shown in Table 1. (SEQ ID NO: 2) Other CD19-targeting antibodies such as SJ25C1 and HD37 are known. (SJ25C1: Bejcek et al. Cancer Res 2005, PMID 7538901; HD37: Pezutto et al. JI 1987, PMID 2437199).

A specific alternative of a polynucleotide coding for a ligand binding domain is shown in Table 9 as the scFv from an antibody that specifically binds CD20. A polynucleotide encoding for a flexible linker including the amino acids GSTSGSGKPGSGEGSTKG (SEQ ID NO: 39) separates the VH and VL chains in the scFV. The amino acid sequence of the scFv is shown in Table 9 (SEQ ID NO: 25). Other CD20-targeting antibodies such as 1F5 (Budde et al. 2013, PLOS One) are known.

Spacer.

In some alternatives, the chimeric receptor nucleic acid comprises a polynucleotide coding for a spacer region. Typically a spacer region is found between the ligand binding domain and the transmembrane domain of the chimeric receptor. In some alternatives, a spacer region provides for flexibility of the ligand binding domain, allows for high expression levels in lymphocytes. A CD19-specific chimeric receptor having a spacer domain of about 229 amino acids had less antitumor activity than a CD19-specific chimeric receptor with a short spacer region comprised of the modified IgG4 hinge only.

In some alternatives, a spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length that is within a range defined by any two of the aforementioned amino acid lengths. In some alternatives, a spacer region has 12 amino acids or less but greater than 1 amino acid, 119 amino acids or less but greater than 1 amino acid, or 229 amino acids or less but greater than 1 amino acid.

In some alternatives, the spacer region is derived from a hinge region of an immunoglobulin like molecule. In some alternatives, a spacer region comprises all or a portion of the hinge region from a human IgG1, human IgG2, a human IgG3, or a human IgG4, and can contain one or more amino acid substitutions. Exemplary sequences of the hinge regions are provided in Table 5. In some alternatives, a portion of the hinge region includes the upper hinge amino acids found between the variable heavy chain and the core, and the core hinge amino acids including a polyproline region.

In some alternatives, hinge region sequences can be modified in one or more amino acids in order to avoid undesirable structural interactions such as dimerization. In a specific alternative, the spacer region comprises a portion of a modified human hinge region from IgG4, for example, as shown in Table 1 or Table 5 (SEQ ID NO: 10). A representative of a polynucleotide coding for a portion of a modified IgG4 hinge region is provided in Table 1. (SEQ ID NO: 1). In some alternatives, a hinge region can have at least about 90%, 92%, 95%, or 100% sequence identity with a hinge region amino acid sequence identified in Table 1 or Table 5. In a specific alternative, a portion of a human hinge region from IgG4 has an amino acid substitution in the core amino acids from CPSP to CPPC.

In some alternatives, all or a portion of the hinge region is combined with one or more domains of a constant region of an immunoglobulin. For example, a portion of a hinge region can be combined with all or a portion of a CH2 or CH3 domain or variant thereof. In some alternatives, the spacer region does not include the 47-48 amino acid hinge region sequence from CD8 alpha or the spacer region comprising an extracellular portion of the CD28 molecule.

In some alternatives, a short spacer region has about 12 amino acids or less but greater than 1 amino acid and comprises all or a portion of a IgG4 hinge region sequence or variant thereof, an intermediate spacer region has about 119 amino acids or less but greater than 1 amino acid and comprises all or a portion of a IgG4 hinge region sequence and a CH3 region or variant thereof, and a long spacer has about 229 amino acids or less but greater than 1 amino acid and comprises all or a portion of a IgG4 hinge region sequence, a CH2 region, and a CH3 region or variant thereof.

A polynucleotide coding for a spacer region can be readily prepared by synthetic or recombinant methods from the amino acid sequence. In some alternatives, a polynucleotide coding for a spacer region is operably linked to a polynucleotide coding for a transmembrane region. In some alternatives, the polynucleotide coding for the spacer region can also have one or more restriction enzyme sites at the 5' and/or 3' ends of the coding sequence in order to provide for easy excision and replacement of the polynucleotide with another polynucleotide coding for a different spacer region. In some alternatives, the polynucleotide coding for the spacer region is codon optimized for expression in mammalian cells. In some alternatives, the polynucleotide coding for the spacer region is codon optimized for expression in human cells.

In an alternative, the spacer region is selected from a hinge region sequence from IgG1, IgG2, IgG3, or IgG4 or portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof, and a CH3 region or variant thereof. In some alternatives, a short spacer region is a modified IgG4 hinge sequence (SEQ ID NO:10) having 12 amino acids or less but greater than 1 amino acid, an intermediate sequence is a IgG4 hinge sequence with a CH3 sequence having 119 amino acids or less but greater than 1 amino acid; or a IgG4 hinge sequence with a CH2 and CH3 region having 229 amino acids or less but greater than 1 amino acid. In some alternatives, a short spacer region has 1, 2, 3, 4, 5, 6, 7, 8, 9, 10, 11 or 12 amino acids or a size within a range defined by any two of the aforementioned amino acid lengths. In some alternatives, a medium spacer region has 13, 20, 30, 40, 50, 60, 70, 80, 90, 100, 110 or 119 amino acids or a size within a range defined by any two of the aforementioned amino acid lengths. In some alternatives, a spacer region has 120, 130, 140, 150, 160, 170, 180, 190, 200, 210 or 219 amino acids or a size within a range defined by any two of the aforementioned amino acid lengths.

Transmembrane Domain.

In some alternatives, the chimeric receptor nucleic acid comprises a polynucleotide coding for a transmembrane domain. The transmembrane domain provides for anchoring of the chimeric receptor in the membrane. In some alternatives, the transmembrane domain of the chimeric antigen receptor is different than that of the genetic tag.

In an alternative, the transmembrane domain that naturally is associated with one of the domains in the chimeric receptor is used. In some cases, the transmembrane domain can be selected or modified by amino acid substitution to avoid binding of such domains to the transmembrane domains of the same or different surface membrane proteins to minimize interactions with other members of the receptor complex.

The transmembrane domain can be derived either from a natural or a synthetic source. When the source is natural, the domain can be derived from any membrane-bound or transmembrane protein. Transmembrane regions comprise at least the transmembrane region(s) of the alpha, beta or zeta chain of the T-cell receptor, CD28, CD3, CD45, CD4, CD8, CD9, CD16, CD22; CD33, CD37, CD64, CD80, CD86, CD134, CD137 and/or CD154. In a specific alternative, the transmembrane domain comprises the amino acid sequence of the CD28 transmembrane domain as shown in Table 2. A representative polynucleotide sequence coding for the CD28 transmembrane domain is shown in Table 1 (within SEQ ID NO: 2).

A transmembrane domain can be synthetic or a variant of a naturally occurring transmembrane domain. In some alternatives, synthetic or variant transmembrane domains comprise predominantly hydrophobic residues such as leucine and valine. In some alternatives, a transmembrane domain can have at least 80%, 85%, 90%, 95%, or 100% amino acid sequence identity with a transmembrane domain as shown in Table 2 or Table 6 or a sequence identity that is a percentage within a range defined by any two of the aforementioned percentages. Variant transmembrane domains preferably have a hydrophobic score of at least 50 as calculated by Kyte Doolittle.

A polynucleotide coding for a transmembrane domain can be readily prepared by synthetic or recombinant methods. In some alternatives, a polynucleotide coding for a transmembrane domain is operably linked to a polynucleotide coding for an intracellular signaling region. In some alternatives, the polynucleotide coding for a transmembrane domain can also have one or more restriction enzyme sites at the 5' and/or 3' ends of the coding sequence in order to provide for easy excision and replacement of the polynucleotide coding for a transmembrane domain with another polynucleotide coding for a different transmembrane domain. In some alternatives, the polynucleotide coding for a transmembrane domain is codon optimized for expression in mammalian cells, preferably human cells.

Intracellular Signaling Domain.

In some alternatives, the chimeric receptor nucleic acid comprises a polynucleotide coding for an intracellular signaling domain. The intracellular signaling domain provides for activation of one function of the transduced cell expressing the chimeric receptor upon binding to the ligand expressed on tumor cells. In some alternatives, the intracellular signaling domain contains one or more intracellular signaling domains. In some alternatives, the intracellular signaling domain is a portion of and/or a variant of an intracellular signaling domain that provides for activation of at least one function of the transduced cell.

Examples of intracellular signaling domains for use in a chimeric receptor of the disclosure include the cytoplasmic sequences of the CD3 zeta chain, and/or co-receptors that act in concert to initiate signal transduction following chimeric receptor engagement, as well as any derivative or variant of these sequences and any synthetic sequence that has the same functional capability. T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner can contain signaling motifs which are known as receptor tyrosine-based activation motifs or ITAMs. Examples of ITAM containing primary cytoplasmic signaling sequences include those derived from CD3 zeta, FcR gamma, CD3 gamma, CD3 delta, CD3 epsilon, CD5, CD22, CD79a, CD79b, and/or CD66d. In some alternatives, the primary signaling intracellular domain can have at least 80%, 85%, 90%, or 95% sequence identity to CD3zeta having a sequence provided in Table 4 or a percentage sequence identity that is within a range defined by any two of the aforementioned percentages. In some alternatives variants of CD3 zeta retain at least one, two, three or all ITAM regions as shown in Table 4.

In a preferred alternative, the intracellular signaling domain of the chimeric receptor can be designed to comprise the CD3-zeta signaling domain by itself or combined with any other desired cytoplasmic domain(s). For example, the intracellular signaling domain of the chimeric receptor can comprise a CD3zeta chain and a costimulatory signaling region.

The co-stimulatory signaling region refers to a portion of the chimeric receptor comprising the intracellular domain of a costimulatory molecule. A co-stimulatory molecule is a cell surface molecule other than an antigen receptor or their ligands that is required for a response of lymphocytes to an antigen. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, zeta chain associated protein kinase (ZAP70), and/or a ligand that specifically binds with CD83. In some alternatives, the co-stimulatory signaling domain can have at least 80%, 85%, 90%, or 95% amino acid sequence identity to the intracellular domain of CD28 as shown in Table 2 or to 4-1BB having a sequence provided in Table 3 or any percent sequence identity that is within a range defined by any two of the aforementioned percentages. In an alternative, a variant of the CD28 intracellular domain comprises an amino acid substitution at positions 186-187, wherein LL is substituted with GG.

The intracellular signaling sequences of the chimeric receptor can be linked to each other in a random or specified order. Optionally, a short oligo- or polypeptide linker, preferably between 2 and 10 amino acids in length can form the linkage. In some alternatives, a short oligo- or polypeptide linker comprise 2, 3, 4, 5, 6, 7, 8, 9, or 10 amino acids or a size that is within a range defined by any two of the aforementioned sizes. In one alternative, the intracellular signaling domains comprises all or a portion of the signaling domain of CD3-zeta or variant thereof and all or a portion of the signaling domain of CD28 or a variant thereof. In another alternative, the intracellular signaling domain comprises all or a portion of the signaling domain of CD3-zeta or variant thereof and all or a portion of the signaling domain of 4-1BB or variant thereof. In yet another alternative, the intracellular signaling domain comprises all or a portion of the signaling domain of CD3-zeta or variant thereof, all or a portion of the signaling domain of CD28 or variant thereof, and all or a portion of the signaling domain of 4-1BB or variant thereof. In a specific alternative, the amino acid sequence of the intracellular signaling domain comprising a variant of CD3zeta and a portion of the 4-1BB intracellular signaling domain is provided in Table 1. A representative nucleic acid sequence is provided in Table 1(within SEQ ID NO: 2).

In an alternative, a polynucleotide coding for an intracellular signaling domain comprises a 4-1BB intracellular domain linked to a portion of a CD3zeta domain. In other alternatives, a 4-1BB intracellular domain and a CD28 intracellular domain are linked to a portion of a CD3 zeta domain.

A polynucleotide coding for an intracellular signaling domain can be readily prepared by synthetic or recombinant methods from the amino acid sequence. In some alternatives, the polynucleotide coding for an intracellular signaling domain can also have one or more restriction enzyme sites at the 5' and/or 3' ends of the coding sequence in order to provide for easy excision and replacement of the polynucleotide coding for an intracellular signaling domain with another polynucleotide coding for a different intracellular signaling domain. In some alternatives, the polynucleotide coding for an intracellular signaling domain is codon optimized for expression in mammalian cells. In some alternatives, the polynucleotide coding for an intracellular signaling domain is codon optimized for expression in human cells.

Linker Domains.

In some alternatives a linker domain is provided for flexibility between domains in a CAR construct. As shown below, a linker (SEQ ID NO: 45) between Domain IV and the transmembrane domain of Her2t led to the construct Her2tG. The linker is used to induce flexibility between protein domains. In other examples, the scFv of many CARs contain four consecutive G3S subunits placed between the Vh and Vl domains of the CAR's scFv. This allows for flexibility in folding of the two scFv domains. In an exemplary alternative, the rational of using two G3S linker subunits would suffice in being able to induce an increased amount of flexibility for Her2tG.

Two G3S linker subunits linked as one (SEQ ID NO: 45) was also used to mimic the spacer length of the CD28hinge and IgG4 hinge. Both the CD28 hinge and IgG4 hinge have been used as spacers previously between the scFv and transmembrane region in CARs that are functional. Both the CD28hinge and IgG4hinge contain a cysteine that facilitate dimerization. While helpful for CARs, this dimerization may inhibit the flexibility of Her2t and therefore not allow for as significant recognition to Herceptin. The advantage of using two G3S linkers (SEQ ID NO: 45) over three or four was to limit vector payload, eliminate potentially unnecessary sequences and at the same time achieve enhanced functionality.

In some alternatives, an isolated polypeptide is provided, wherein the isolated polypeptide comprises at least 95% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab.

Host Cells and Compositions: T Lymphocyte Populations.

The compositions described herein provide for genetically modified host cells with the vectors and/or constructs as described herein. In some alternatives, the host cells are CD4+ and/or CD8+T lymphocytes. In some alternatives, the host cells are precursor T cells. In some alternatives, the host cells are hematopoietic stem cells.

T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some alternatives, the T cells are autologous T cells obtained from the patient.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells or an amount that is within a range defined by any two of the aforementioned amounts for each T lymphocyte in the initial population to be expanded); and incubating the culture (e.g. for a time sufficient to expand the numbers of T cells). The non-dividing feeder cells can comprise gamma-irradiated PBMC feeder cells. In some alternatives, the PBMC are irradiated with gamma rays in the range of 3000 to 3600 rads to prevent cell division. In some alternatives, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25 degrees Celsius, preferably at least 30 degrees, more preferably about 37 degrees. In some alternatives, the temperature for the growth of human T lymphocytes is 22, 24, 26, 28, 30, 32, 34, 36, 37 degrees Celsius or any other temperature between any two endpoints of any of the listed values.

The T lymphocytes expanded include CD8+ cytotoxic T lymphocytes (CTL) and CD4+ helper T lymphocytes that can be specific for an antigen present on a human tumor or a pathogen.

Optionally, the expansion method can further comprise the step of adding non-dividing EBV-transformed lymphoblastoid cells (LCL) as feeder cells. LCL can be irradiated with gamma rays in the range of 6000 to 10,000 rads. In some alternatives, the LCL are irradiated with gamma rays in of 6000, 6500, 7000, 7500, 8000, 8500, 9000, 9500 or 10,000 rads or any amount of rads between two endpoints of any of the listed values. The LCL feeder cells can be provided in any suitable amount, such as a ratio of LCL feeder cells to initial T lymphocytes of at least about 10:1.

Optionally, the expansion method can further comprise the step of adding anti-CD3 and/or anti CD28 antibody to the culture medium (e.g., at a concentration of at least about 0.5 ng/ml). Optionally, the expansion method can further comprise the step of adding IL-2 and/or IL-15 to the culture medium (e.g., wherein the concentration of IL-2 is at least about 10 units/ml).

After isolation of T lymphocytes both cytotoxic and helper T lymphocytes can be sorted into naïve, memory, and effector T cell subpopulations either before or after expansion.

CD8+ cells can be obtained by using standard methods. In some alternatives, CD8+ cells are further sorted into naïve, central memory, and effector memory cells by identifying cell surface antigens that are associated with each of those types of CD8+ cells. In some alternatives, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some alternatives, the expression of phenotypic markers of central memory TCM include CD45RO, CD62L, CCR7, CD28, CD3, and CD127 and are negative or low for granzyme B. In some alternatives, central memory T cells are CD45RO+, CD62L+, CD8+ T cells. In some alternatives, effector $T_E$ are negative for CD62L, CCR7, CD28, and CD127, and positive for granzyme B and perforin. In some alternatives, naïve CD8+T lymphocytes are characterized by the expression of phenotypic markers of naïve T cells including CD62L, CCR7, CD28, CD3, CD127, and CD45RA.

CD4+T helper cells are sorted into naïve, central memory, and effector cells by identifying cell populations that have cell surface antigens. CD4+ lymphocytes can be obtained by standard methods. In some alternatives, naïve CD4+T lymphocytes are CD45RO−, CD45RA+, CD62L+, CD4+ T cells. In some alternatives, central memory CD4+ cells are CD62L+ and CD45RO+. In some alternatives, effector CD4+ cells are CD62L− and CD45RO−.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% ofthe cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population or any percent range of cells between the percent values of any of the aforementioned values when compared to a reference cell population. In some alternatives, a cell population positive for one or markers refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any percentage within a range defined by any two of the aforementioned percentages when compared to a reference cell population.

In some alternatives, populations of CD4+ and CD8+ that are antigen specific can be obtained by stimulating naïve or antigen specific T lymphocytes with antigen. For example, antigen-specific T cell lines or clones can be generated to Cytomegalovirus antigens by isolating T cells from infected subjects and stimulating the cells in vitro with the same antigen. Naïve T cells can also be used. Any number of antigens from tumor cells can be utilized as targets to elicit T cell responses. In some alternatives, the adoptive cellular immunotherapy compositions are useful in the treatment of a disease or disorder including a solid tumor, hematologic malignancy, breast cancer or melanoma.

Modification of T Lymphocyte Populations.

In some alternatives, it can be desired to introduce functional genes into the T cells to be used in immunotherapy in accordance with the present disclosure. For example, the introduced gene or genes can improve the efficacy of therapy by promoting the viability and/or function of transferred T cells; or they can provide a genetic marker to permit selection and/or evaluation of in vivo survival or migration; or they can incorporate functions that improve the safety of immunotherapy, for example, by making the cell susceptible to controlled expression of the transgene. This can be carried out in accordance with known techniques that will be apparent to those skilled in the art based upon the present disclosure.

In some alternatives, T cells are modified with vector coding for genetic tags as described herein. In some alternatives, cells are modified with a vector comprising a polynucleotide coding for a chimeric antigen receptor operably linked to a genetic tag. In other alternatives, cells are modified with a vector comprising a polynucleotide coding for a genetic tag alone. In some alternatives, the T cells are obtained from the subject to be treated, in other alternatives, the lymphocytes are obtained from allogeneic human donors, preferably healthy human donors.

Chimeric receptors can be constructed with a specificity for any cell surface marker by utilizing antigen binding fragments or antibody variable domains of, for example, antibody molecules. The antigen binding molecules can be linked to one or more cell signaling modules. In some alternatives, cell signaling modules include CD3 transmembrane domain, CD3 intracellular signaling domains, and CD28 transmembrane domains. In some alternatives, the intracellular signaling domain comprises a CD28 transmembrane and signaling domain linked to a CD3 zeta intracellular domain.

In some alternatives, the same or a different chimeric receptor can be introduced into each of population of CD4+ and CD8+T lymphocytes. In some alternatives, the chimeric receptor in each of these populations has a ligand binding domain that specifically binds to the same ligand on the tumor or infected cell or a different antigen or epitope. The cellular signaling modules can differ. In some alternatives, the intracellular signaling domain of the CD8+ cytotoxic T cells is the same as the intracellular signaling domain of the CD4+ helper T cells. In other alternatives, the intracellular signaling domain of the CD8+ cytotoxic T cells is different than the intracellular signaling domain of the CD4+ helper T cells. Each chimeric receptor is operably linked to a different genetic tag allowing for selection and identification of transduced cells expressing both chimeric antigen receptors.

Alternatives include methods of manufacturing compositions comprising host cells as described herein. In some alternatives, a method comprises introducing an isolated nucleic acid, such as a nucleic acid coding for isolated polypeptide comprising at least 95% sequence identity to a polypeptide of an extracellular domain of HER2 polypeptide having a sequence of amino acids 511 to 652 or 563 to 652 of SEQ ID NO: 23 linked to a transmembrane domain, wherein the isolated polypeptide specifically binds to an antibody that binds to an epitope in Domain IV of Her2, into a host cell; and culturing the host cells in a medium comprising at least one growth factor. In some alternatives, a method further comprises selecting the host cells for expression of Her2t before or after or both before and after the culturing step. In other alternatives, a method of manufacturing further comprises introducing a second nucleic acid coding for a second chimeric antigen receptor and a second genetic tag into the host cell. In some alternatives, the method further comprises selecting the host cells for expression of the second genetic tag before or after or both before and after the culturing step. In some alternatives, the host cells are precursor T cells. In some alternatives, the host cells are hematopoietic stem cells.

In other alternatives, a method comprises introducing a first isolated nucleic acid, such as a nucleic acid coding for isolated polypeptide comprising at least 95% sequence identity to a polypeptide of an extracellular domain of HER2 polypeptide having a sequence of amino acids 511 to 652 or 563 to 652 of SEQ ID NO: 23 linked to a transmembrane domain, wherein the isolated polypeptide specifically binds to an antibody that binds to an epitope in Domain IV of Her2, into a first host cell; selecting first host cells that express Her2t, introducing a second nucleic acid coding for a second chimeric antigen receptor and a second genetic tag into a second host cell, selecting second host cells for expression of the second genetic tag, and optionally, culturing the first and second host cells in a medium comprising at least one growth factor. In some alternatives, a composition comprises a first and second host cell population. In some alternatives, the host cells are precursor T cells. In some alternatives, the host cells are hematopoietic stem cells.

In some alternatives each of the CD4 or CD8 T lymphocytes can be sorted in to naïve, central memory, effector memory or effector cells prior to transduction as described herein. In some alternatives, each of the CD4 or CD8 T lymphocytes can be sorted into naïve, central memory, effector memory, or effector cells after transduction.

As described herein, in some alternatives, naïve CD4+ cells are CD45RO−, CD45RA+, CD62L+, and/or CD4+ positive T cells. In some alternatives, central memory CD4+ cells are CD62L positive and/or CD45RO positive. In some alternatives, effector CD4+ cells are CD62L negative and/or CD45RO positive. Each of these populations can be independently modified with a chimeric receptor.

As described herein, in some alternatives, memory T cells are present in both CD62L+ and/or CD62L− subsets of CD8+ peripheral blood lymphocytes. PBMC are sorted into CD62L-CD8+ and/or CD62L+CD8+ fractions after staining with anti-CD8 and anti-CD62L antibodies. In some alternatives, the expression of phenotypic markers of central memory T cells (TCM) include CD62L, CCR7, CD28, CD3, and/or CD127 and are negative or low for granzyme B. In some alternatives, central memory T cells are CD45RO+, CD62L+, and/or CD8+ T cells. In some alternatives, effector T cells ($T_E$) are negative for CD62L, CCR7, CD28, and/or CD127, and positive for granzyme B and/or perforin. In some alternatives, naïve CD8+T lymphocytes are characterized by CD8+, CD62L+, CD45RO+, CCR7+, CD28+ CD127+, and/or CD45RO+. Each of these populations can be independently modified with a chimeric receptor.

Various transduction techniques have been developed which utilize recombinant infectious virus particles for gene delivery. This represents a currently preferred approach to the transduction of T lymphocytes of the present invention. The viral vectors which have been used in this way include virus vectors derived from simian virus 40, adenoviruses, adeno-associated virus (AAV), lentiviral vectors, and retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral or lentiviral infection.

Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell. In some alternatives, retroviral or lentiviral vectors are used for gene transfer into eukaryotic cells. In some alternatives, the cells are human cells.

It is contemplated that overexpression of a stimulatory factor (for example, a lymphokine or a cytokine) can be toxic to the treated individual. Therefore, it is within the scope of the invention to include gene segments that cause the T cells of the invention to be susceptible to negative selection in vivo. By "negative selection" it is meant that the infused cell can be eliminated as a result of a change in the in vivo condition of the individual. The negative selectable phenotype can result from the insertion of a gene that confers sensitivity to an administered agent, for example, a compound. In some alternatives, the genetic tag Her2t also provides for negative selection in vivo. For example, if it was desired to eliminate CAR expressing cells with the genetic tag Her2t, an antibody that binds to Domain IV of Her2 (e.g. trastuzumab) or an antibody that competes for binding with an antibody that binds to Domain IV of Her2, is administered to the subject. In preferred alternatives for eliminating the transduced cells the antibodies, the antibodies contain an Fc region in order to activate antibody dependent cellular cytotoxicity reaction to kill the transduced cells. In other alternatives, the antibody or fragment thereof is linked to a cytotoxic agent. The cytotoxic conjugate binds to cells expressing CAR and her2t and kills the cells. This method provides a way to ablate administered cells that are associated with toxicity or adverse side effects.

Other negative selectable genes are known in the art, and include, inter alia the following: the Herpes simplex virus type I thymidine kinase (HSV-I TK) gene, which confers ganciclovir sensitivity; the cellular hypoxanthine phosphribosyltransferase (HPRT) gene, the cellular adenine phosphoribosyltransferase (APRT) gene, and bacterial cytosine deaminase.

A variety of methods can be employed for transducing T lymphocytes, as is well known in the art. In some alternatives, transduction is carried out using lentiviral vectors.

In some alternatives, CD4+ and CD8+ cells each can separately be modified with an expression vector encoding a chimeric receptor to form defined populations. In some alternatives, cells can be separately modified with a vector comprising a polynucleotide coding for a CAR and first genetic tag and/or and a vector comprising a polynucleotide coding for a CAR and second and different genetic tag. In some alternatives, the CAR constructs can be the same or different. For example, CD8 T cells are transduced with a CAR construct having the first genetic tag and CD4 T cells are tranduced with the same CAR with second genetic tag.

In some alternatives, these cells are then further sorted into subpopulations of naïve, central memory and effector cells as described above by sorting for cell surface antigens unique to each of those cell populations. In addition, CD4+ or CD8+ cell populations can be selected by their cytokine profile or proliferative activities. For example, CD4+T lymphocytes that have enhanced production of cytokines such as IL-2, IL-4, IL-10, TNFα, and/or IFNγ as compared to sham transduced cells or transduced CD8+ cells when stimulated with antigen can be selected. In other alternatives, naïve or central memory CD4+ T cells that have enhanced production of IL-2 and/or TNFα are selected. Likewise, CD8+ cells that have enhanced IFNγ production are selected as compared to sham transduced CD8+ cells. In some alternatives, CD4+ or CD8+ cell populations are selected by their cytokine profile or proliferative activities. In some alternatives, CD4+T lymphocytes that have enhanced production of cytokines such as IL-2, IL-4, IL-10, TNFα, and/or IFNγ as compared to sham transduced cells or transduced CD8+ cells when stimulated with antigen are selected.

In some alternatives, CD4+ and CD8+ cells are selected that are cytotoxic for antigen bearing cells. In some alternatives, CD4+ are expected to be weakly cytotoxic as compared to CD8+ cells. In a preferred alternative, transduced lymphocytes, such as CD8+ central memory cells, are selected that provide for tumor cell killing in vivo using an animal model established for the particular type of cancer.

In yet other alternatives, transduced cells are selected for the expression of a genetic tag. In some alternatives, after transduction, cells expressing, for example, Her2t or EGFRt are selected using antibodies that bind to the genetic tags. In some alternatives, the antibodies provide for selection of cell population containing at least 80-100% cells positive for the genetic tag.

Selected cells can be evaluated for transgene expression using techniques such as Western blot or flow cytometry. In some alternatives the cells selected for expression of a genetic tag are also further characterized for expression of the CAR by analyzing, for example, the amount of the stimulatory domain (e.g. CD3zeta), Protein L, and T2A. In some alternatives, cells having a ratio of about 1:0.1 to 10:0.1 of expression of the CAR to the genetic tag are selected. In some alternatives, cells having a ratio of about 1:0.1, 2:0.1, 3:0.1, 4:0.1, 5:01, 6:0.1, 7:0.1, 8:0.1, 9:01, or 10:0.1 of expression of the CAR to the genetic tag, or any other ratio of the CAR to the genetic tag that is between any of the listed ratios, are selected. In some alternatives, the Her2t genetic tag can be utilized in cases where the expression of the CAR is low as it provides better transgene expression levels than EGFRt. In some alternatives, a Her2t genetic tag provides for at least a 1.5 fold, 2 fold, 5 fold, or 10 fold increase in transgene expression as compared to EGFRt genetic tag, or any other fold increase between any two of the listed values.

In yet other alternatives, transduced chimeric receptor expressing T cells are selected that can persist in vivo using an animal model established for the particular type of cancer. In some alternatives, transduced chimeric receptor CD8+ central memory cells have been shown to persist in vivo after introduction into the animal for about 3 day or more, 10 days or more, 20 days or more, 30 days or more, 40 days or more, or 50 days or more, or any other time between any two of the listed values. Persistence in vivo can be determined by imaging with a detectably labeled antibody that binds to a genetic tag, such as Her2t or EGFRt.

The disclosure contemplates that combinations of CD4+ and CD8+ T cells will be utilized in the compositions. In one alternative, combinations of chimeric receptor transduced CD4+ cells can be combined with chimeric receptor transduced CD8+ cells of the same ligand specificity or combined with CD8+ T cells that are specific for a distinct tumor ligand and different genetic tag. In other alternatives, chimeric receptor transduced CD8+ cells are combined with chimeric receptor transduced CD4+ cells specific for a different ligand expressed on the tumor. In yet another alternative, chimeric receptor modified CD4+ and CD8+ cells are combined. In some alternatives CD8+ and CD4+ cells can be combined in different ratios for example, a 1:1 ratio of CD8+ and CD4+, a ratio of 10:1 of CD8+ to CD4+, or a ratio of 100:1 of CD8+ to CD4+, or any other ratio of CD8+ to CD4+ that is between any two of the listed ratio values. In some alternatives, the combined population is tested for cell proliferation in vitro and/or in vivo, and the ratio of cells that provides for proliferation of cells is selected.

Before or after transduction and/or selection for chimeric receptor bearing cells, the cell populations are preferably expanded in vitro until a sufficient number of cells are obtained to provide for at least one infusion into a human subject, typically around $10^4$ cells/kg to $10^9$ cells/kg. In some alternatives, the transduced cells are cultured in the presence of antigen bearing cells, anti CD3, anti CD28, and IL 2, IL-7, IL 15, and/or IL-21 and combinations thereof.

Each of the subpopulations of CD4+ and CD8+ cells can be combined with one another. In a specific alternative, modified naïve or central memory CD4+ cells are combined with modified central memory CD8+ T cells to provide a synergistic cytotoxic effect on antigen bearing cells, such as tumor cells.

Compositions.

The disclosure provides for an adoptive cellular immunotherapy composition comprising a genetically modified T lymphocyte cell preparation as described herein.

In some alternatives, the T lymphocyte cell preparation comprises CD4+ T cells that have a chimeric receptor comprising an extracellular antibody variable domain specific for a ligand associated with the disease or disorder, a spacer region, a transmembrane domain, and an intracellular signaling domain of a T cell receptor and a genetic tag as described herein. In other alternatives, an adoptive cellular immunotherapy composition further comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a spacer region, a transmembrane domain, and an intracellular signaling domain of a T cell receptor and a genetic tag as described herein. In some alternatives, the chimeric receptor modified T cell population of the disclosure can persist in vivo for at least about 3 days or longer. In alternative each of these populations can be combined with one another or other cell types to provide a composition.

Alternatives include CD4 and/or CD8 host cells as described herein. In some alternatives, a host cell comprises an isolated nucleic acid, such as a nucleic acid coding for an isolated polypeptide comprising at least 95% sequence identity to a polypeptide of an extracellular domain of HER2 polypeptide having a sequence of amino acids 511 to 652 or 563 to 652 of SEQ ID NO:23 linked to a transmembrane domain, wherein the isolated polypeptide specifically binds to an antibody that binds to an epitope in Domain IV of Her2, and a second nucleic acid coding for a second chimeric antigen receptor and a second genetic tag. In some alternatives, the host cells are precursor T cells. In some alternatives, the host cells are hematopoietic stem cells.

In other alternatives, a composition comprises a first host cell comprising a first isolated nucleic acid, such as a nucleic acid coding for an isolated polypeptide comprising at least 95% sequence identity to a polypeptide of an extracellular domain of HER2 polypeptide having a sequence of amino acids 511 to 652 or 563 to 652 of SEQ ID NO:23 linked to a transmembrane domain, wherein the isolated polypeptide specifically binds to an antibody that binds to an epitope in Domain IV of Her2, and a second host cell comprising a second nucleic acid coding for a second chimeric antigen receptor and a second genetic tag. In some alternatives, the first host cell and the second host cell can be the same or different type of host cells, for example, the first host cell can be a CD8 central memory cells and the second host cell can be a naïve CD4 cell. In some alternatives, first and second host cells are each selected from the group consisting of CD8 T cells, CD4 T cells, CD4 naïve T cells, CD8 naïve T cells, CD8 central memory cells, CD4 central memory cells, and combinations thereof.

In some alternatives, the CD4+T helper lymphocyte cell is selected from the group consisting of naïve CD4+ T cells, central memory CD4+ T cells, effector memory CD4+ T cells, or bulk CD4+ T cells. In some alternatives, CD4+ helper lymphocyte cell is a naïve CD4+ T cell, wherein the naïve CD4+ T cell comprises a CD45RO−, CD45RA+, CD62L+CD4+ T cell.

In some alternatives, the CD8+T cytotoxic lymphocyte cell is selected from the group consisting of naïve CD8+ T cells, central memory CD8+ T cells, effector memory CD8+ T cells or bulk CD8+ T cells. In some alternatives, the CD8+ cytotoxic T lymphocyte cell is a central memory T cell wherein the central memory T cell comprises a CD45RO+, CD62L+, CD8+ T cell. In yet other alternatives, the CD8+ cytotoxic T lymphocyte cell is a central memory T cell and the CD4+ helper T lymphocyte cell is a naïve or central memory CD4+ T cell.

Methods.

The disclosure provides methods of making adoptive immunotherapy compositions and uses or methods of using these compositions for performing cellular immunotherapy in a subject having a disease or disorder.

Alternatives include methods of manufacturing compositions comprising host cells as described herein. In some alternatives, a method comprises introducing an isolated nucleic acid, such as a nucleic acid coding for isolated polypeptide comprising at least 95% sequence identity to a polypeptide of an extracellular domain of HER2 polypeptide having a sequence of amino acids 511 to 652 or 563 to 652 of SEQ ID NO: 23 linked to a transmembrane domain, wherein the isolated polypeptide specifically binds to an antibody that binds to an epitope in Domain IV of Her2, into a host cell; and culturing the host cells in a medium comprising at least one growth factor. In some alternatives, a method further comprises selecting the host cells for expression of Her2t before or after or both before and after the culturing step. In other alternatives, a method of manufacturing further comprises introducing a second nucleic acid coding for a second chimeric antigen receptor and a second genetic tag into the host cell. In some alternatives, the method further comprises selecting the host cells for expression of the second genetic tag before or after or both before and after the culturing step. In some alternatives, the host cells are precursor T cells. In some alternatives, the host cells are hematopoietic stem cells.

In other alternatives, a method comprises introducing a first isolated nucleic acid, such as a nucleic acid coding for isolated polypeptide comprising at least 95% sequence identity to a polypeptide of an extracellular domain of HER2 polypeptide having a sequence of amino acids 511 to 652 or 563 to 652 of SEQ ID NO: 23 linked to a transmembrane domain, wherein the isolated polypeptide specifically binds to an antibody that binds to an epitope in Domain IV of Her2, into a first host cell; selecting first host cells that express Her2t, introducing a second nucleic acid coding for a second chimeric antigen receptor and a second genetic tag into a second host cell, selecting second host cells for expression of the second genetic tag, and optionally, culturing the first and second host cells in a medium comprising at least one growth factor. In some alternatives, a composition comprises a first and second host cell population.

In some alternatives, a method of manufacturing the compositions comprises obtaining a modified naïve or central memory CD4+T helper cell, wherein the modified helper T lymphocyte cell preparation comprises CD4+ T cells that have a chimeric receptor comprising a ligand binding domain specific for a tumor cell surface molecule, a spacer domain, a transmembrane domain, and an intracellular signaling domain and a genetic tag as described herein.

In another alternative, a method further comprises obtaining a modified CD8+ central memory T cell, wherein the modified central memory CD8 T lymphocyte cell preparation comprises CD8+ cells that have a chimeric receptor comprising a ligand binding domain specific for a tumor cell surface molecule, a spacer domain, a transmembrane domain, and an intracellular signaling domain and a genetic tag as described herein. In other alternatives, CD8+ cells have a cytokine or chemokine receptor under the control of an inducible promoter.

The chimeric antigen receptor and genetic tag in both modified CD4+ T cells and modified CD8+ cytotoxic T cell can be the same or different. For example, modified CD4+ T cells that have a first CAR and first genetic tag, while the CD8+ cytotoxic T cell comprises CD8+ cells that have a second and different CAR and second and different genetic tag. In some alternatives, the polynucleotide can code for a chimeric antigen receptor that is the same in both the CD4+ and the CD8+ cell population. The difference between the two CAR constructs can include the specificity or affinity of the ligand binding domain for an antigen or epitope, the length and sequence of the spacer region, and the intracellular signaling components.

The preparation of the CD4+ and CD8+ cells that are modified with a chimeric receptor has been described above as well as in the examples. Antigen specific T lymphocytes can be obtained from a patient having the disease or disorder or can be prepared by in vitro stimulation of T lymphocytes in the presence of antigen. Subpopulations of CD4+ and CD8+T lymphocytes that are not selected for antigen specificity can also be isolated as described herein and combined in the methods of manufacturing. Cell populations are advantageously selected for expression of one or more genetic tags, such as Her2t and/or EGFRt.

In some alternatives, the combination of cell populations can be evaluated for uniformity of cell surface makers, the ability to proliferate through at least two generations, to have a uniform cell differentiation status. Quality control can be performed by determining the ratio of expression of CAR to the expression of the genetic tag. Cell differentiation status and cell surface markers on the chimeric receptor modified T cells can be determined by flow cytometry. In some alternatives, the markers and cell differentiation status on the CD8+ cells include CD3, CD8, CD62L, CD28, CD27, CD69, CD25, PD-1, CTLA-4, CD45RO, and/or CD45RA. In some alternatives, the markers and the cell differentiation status on the CD4+ cells include CD3, CD4, CD62L, CD28, CD27, CD69, CD25, PD-1, CTLA-4 CD45RO, and/or CD45RA.

In some alternatives, the chimeric receptor modified T cells as described herein are able to persist in vivo for at least 3 days, or at least 10 days. In some alternatives, the chimeric receptor modified T cells as described herein are able to persist in vivo for at least 3 days, 4 days, 5, days, 6 days, 7 days, 8 days, 9 days, or 10 days or any time within a range defined by any two of the aforementioned time points. In some alternatives, the chimeric receptor modified T cells can proliferate in vivo through at least 2, or at least 3 generations as determined by CFSE dye dilution. Proliferation and persistence of the chimeric receptor modified T cells can be determined by using an animal model of the disease or disorder and administering the cells and determining persistence and/or proliferative capacity of the transferred cells by detecting the cells using a detectably labeled antibody that binds to the genetic tag such as Erbitux(EGFRt) and/or Herceptin (Her2t). When using antibodies or antigen binding fragments to detect transgene expressing cells in vivo, and antibody or antigen binding fragment preferably does not include a Fc portion in order to minimize any ADCC reaction. In other some alternatives, proliferation and activation can be tested in vitro by going through multiple cycles of activation with antigen bearing cells.

The disclosure also provides methods of performing cellular immunotherapy in a subject having a disease or disorder comprising: administering a composition of lymphocytes expressing one or more chimeric antigen receptor and genetic tag as described herein. In some alternatives, a method of performing cellular immunotherapy in a subject having a disease or disorder is provided, wherein the method comprises administering a composition of lymphocytes expressing one or more chimeric antigen receptor and genetic tag.

Alternatives include a method of treating patient having cancer expressing a tumor antigen comprises administering an effective amount of a compositions as described herein, wherein the cells of the composition express a chimeric antigen receptor that comprises an antigen binding domain that binds to the tumor antigen expressed on the cancer cell and a genetic tag. In some alternatives, the cancer has a tumor antigen recognized by the chimeric antigen receptor on the cells. In some alternatives, the cancer is selected from the group consisting of breast cancer, diffuse large B cell lymphoma, lymphoma, ALL, CLL, and multiple myeloma.

In some alternatives, a method of treating patient having cancer expressing a tumor antigen comprises administering an effective amount of a compositions as described herein, wherein the cells of the composition express a first chimeric antigen receptor that comprises an antigen binding domain that binds to the tumor antigen expressed on the cancer cell and a first genetic tag and a second chimeric antigen receptor that comprises an antigen binding domain that binds to the tumor antigen expressed on the cancer cell and a second genetic tag.

In some alternatives, a method of treating patient having cancer expressing a tumor antigen comprises administering an effective amount of a composition comprising a first host cell that expresses a first chimeric antigen receptor that comprises an antigen binding domain that binds to the tumor antigen expressed on the cancer cell and a first genetic tag and a second host cell comprising a second chimeric antigen receptor that comprises an antigen binding domain that binds to the tumor antigen expressed on the cancer cell and a second genetic tag. In some alternatives, the host cells are precursor T cells. In some alternatives, the host cells are hematopoietic stem cells.

In other alternatives, a method of treating a patient having cancer and/or expressing a tumor antigen is provided, wherein the method comprises administering an effective amount of a composition as described herein and an antibody that specifically binds to the genetic tag, wherein the cells of the composition express a chimeric antigen receptor that comprises an antigen binding domain that binds to the tumor antigen expressed on the cancer cell and a genetic tag. In some alternatives, the antibody binds to Domain IV of Her2, or binds to EGFRt. In some alternatives, the antibodies are Herceptin or Erbitux.

In some alternatives, if a toxic effect of the composition is observed, an antibody that binds the genetic tag is administered. The antibody can bind to and kill the CAR expressing cells of the composition in order to avoid toxic and/or fatal side effects. In some alternatives, the antibody or antigen binding fragment preferable contains a Fc fragment in order to activate ADCC reactions. In other alternatives, the antibody or antigen binding fragment is conjugated to a cytotoxic agent. Cytotoxic agents include cantansinoids, calicheamicin and/or auristatins. In some alternatives, the cytotoxic agents comprise cantansinoids, calicheamicin and/or auristatins.

In some alternatives, an antibody is detectably labelled in order to allow tracking of the cells in vivo. In some alternatives, when the antibody is used for detection in vivo, it is preferred that the antibody or antigen binding fragment lacks all or a portion of the Fc region in order to avoid ADCC reactions. Detectable labels include biotin, His tags, myc tags, radiolabels, and/or fluorescent labels. In some alternatives the detectable labels comprise biotin, His tags, myc tags, radiolabels, and/or fluorescent labels.

In other alternatives, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain specific for a tumor cell surface molecule, a spacer domain, a transmembrane domain, and an intracellular signaling domain and a first genetic tag as described herein, and/or a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that have a chimeric receptor comprising a ligand binding domain specific for a tumor cell surface molecule, a spacer domain, a transmembrane domain, and an intracellular signaling domain and a second genetic tag.

Another alternative describes a method of performing cellular immunotherapy in a subject having a disease or disorder comprising: analyzing a biological sample of the subject for the presence of a target molecule associated with the disease or disorder and administering the adoptive immunotherapy compositions described herein, wherein the chimeric receptor specifically binds to the target molecule.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects. In some alternatives, the subject is a primate subject or a human.

The methods are useful in the treatment of, for example, hematologic malignancy, melanoma, breast cancer, and other epithelial malignancies or solid tumors. In some alternatives, the molecule associated with the disease or disorder is selected from the group consisting of orphan tyrosine kinase receptor ROR1, Her2, EGFR, CE7, hB7H3, CD19, CD20, CD22, mesothelin, CEA, and hepatitis B surface antigen.

Subjects that can be treated include subjects afflicted with cancer, including but not limited to colon, lung, liver, breast, renal, prostate, ovarian, skin (including melanoma), bone, and brain cancer, etc. In some alternatives, the tumor associated antigens or molecules are known, such as melanoma, breast cancer, squamous cell carcinoma, colon cancer, leukemia, myeloma, and prostate cancer. In other alternatives the tumor associated molecules can be targeted with genetically modified T cells expressing an engineered chimeric receptor. Examples include but are not limited to B cell lymphoma, breast cancer, prostate cancer, and leukemia. In some alternatives, the subject has B cell lymphoma, breast cancer, prostate cancer, and/or leukemia.

Cells prepared as described above can be utilized in methods and compositions for adoptive immunotherapy in accordance with known techniques, or variations thereof that will be apparent to those skilled in the art based on the instant disclosure.

In some alternatives, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

In some alternatives, a treatment effective amount of cells in the composition is a transduced CD4 or CD8 cell or at least 2 cell subsets (for example, 1 CD8+ central memory T cell subset and 1 CD4+ helper T cell subset) or is more typically greater than $10^2$ cells, and up to $10^6$, up to and including $10^8$ or $10^9$ cells and can be more than $10^{10}$ cells or any amount of cells defined between any two endpoints of any of the listed values.

The number of cells will depend upon the ultimate use for which the composition is intended, as will the type of cells included therein. For example, if cells that are specific for a particular antigen are desired, then the population will contain greater than 70%, generally greater than 80%, 85% and 90-95% of such cells or any percent amount of cells within a range defined by any two of the aforementioned percentages.

For uses provided herein, the cells are generally in a volume of a liter or less but greater than 1 nl, can be 500 mls or less but greater than 1 nl, even 250 mls or 100 mls or less but greater than 1 nl, or any volume defined between two endpoints of any of the listed values.

Hence the density of the desired cells is typically greater than $10^4$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^9$, $10^{10}$ or $10^{11}$ cells or any amount of cells within a range defined by two of the aforementioned amounts.

In some alternatives, the lymphocytes can be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $3\times10^{10}$ cells, preferably in the range of at least $10^7$ to $10^9$ cells or any amount of cells within a range defined by two of the aforementioned amounts.

The T cells can be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein.

In some alternatives, the composition as described herein are administered intravenously, intraperitoneally, intratumorly, into the bone marrow, into the lymph node, and/or into cerebrospinal fluid. In some alternatives, the chimeric receptor engineered compositions are delivered to the site of the tumor. Alternatively, the compositions as described herein can be combined with a compound that targets the cells to the tumor or the immune system compartments and avoid sites such as the lung.

In some alternatives, the compositions as described herein are administered with chemotherapeutic agents and/or immunosuppressants. In an alternative, a patient is first treated with a chemotherapeutic agent that inhibits or destroys other immune cells followed by the compositions described herein. In some cases, chemotherapy can be avoided entirely. The present invention is illustrated further in the examples set forth below.

Additional Alternatives.

In some alternatives, an isolated polypeptide is provided, wherein the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab.

In some alternatives, an isolated polypeptide is provided wherein the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab.

In some alternatives, an isolated nucleic acid is provided wherein the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of L E G G G E G R G S L L T C G (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR). In some alternatives, the size of the isolated nucleic acid comprises a size of 5, 6, 7, 8, 9, 10, 11, 12, 13, 14, 14.9 Kb, or any size in between any two of the construct size listed.

In some alternatives, a host cell is provided wherein the host cell comprises an isolated nucleic acid, wherein the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of L E G G G E G R G S L L T C G (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR). In some alternatives, the host cell is selected from the group consisting of CD8 T cells, CD4 T cells, CD4 naïve T cells, CD8 naïve T cells, CD8 central memory cells, and CD4 central memory cells, or combinations thereof. In some alternatives, the host cell is autologous. In some alternatives, the host cell is antigen specific. In some alternatives, the host cells are precursor T cells. In some alternatives, the host cells are hematopoietic stem cells. In some alternatives, the size of the isolated nucleic acid comprises a size of 5, 6, 7, 8, 9, 10, 11, 12, 13, 14, 14.9 Kb, or any size in between any two of the construct size listed.

In some alternatives, a composition comprising host cells is provided wherein the host cells comprise an isolated nucleic acid, wherein the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of L E G G G E G R G S L L T C G (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR). In some alternatives, the host cell is selected from the group consisting of CD8 T cells, CD4 T cells, CD4 naïve T cells, CD8 naïve T cells, CD8 central memory cells, and CD4 central memory cells, or combinations thereof. In some alternatives, the host cell is autologous. In some alternatives, the host cell is antigen specific. In some alternatives, the host cells are precursor T cells. In some alternatives, the host cells are hematopoietic stem cells. In some alternatives, the size of the isolated nucleic acid comprises a size of 5, 6, 7, 8, 9, 10, 11, 12, 13, 14, 14.9 Kb, or any size in between any two of the construct size listed.

In some alternatives, a method of manufacturing a composition is provided, wherein the method comprises introducing an isolated nucleic acid into a host cell and culturing the host cells in a medium comprising at least one growth factor. In some alternatives, the isolated nucleic acid encodes a polypeptide. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide has the sequence of SEQ ID NO: 17. In some alternatives, the antibody is trastuzumab. In some alternatives, the isolated polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER, and wherein the extracellular domain of HER2 polypeptide having a sequence of amino acids 563 to 652 of SEQ ID NO: 23 is linked to the transmembrane domain by a sequence comprising amino acids GGGSGGGS (SEQ ID NO: 45). In some alternatives, the HER2 polypeptide comprises amino acids glutamic acid 580, aspartic acid 582, aspartic acid 592, phenylalanine 595, and glutamine 624 of SEQ ID NO: 23. In some alternatives, the HER2 polypeptide comprises amino acids 563-652 of SEQ ID NO: 23. In some alternatives, the transmembrane domain comprises amino acids 653-675 of SEQ ID NO: 23. In some alternatives, the isolated polypeptide further comprises a leader peptide that provides for cell surface expression. In some alternatives, the leader peptide comprises an amino acid sequence set forth in SEQ ID NO: 17. In some alternatives, the antibody is trastuzumab. In some alternatives, the isolated nucleic acid further comprises a promoter. In some alternatives, the isolated nucleic acid further comprises a transgene. In some alternatives, the transgene comprises a polynucleotide encoding a chimeric antigen receptor. In some alternatives, the chimeric antigen receptor comprises an antigen binding domain, a spacer domain, a transmembrane domain and at least one stimulatory domain. In some alternatives, the polynucleotide encoding the transgene is linked to the nucleic acid encoding the HER2 polypeptide with a self-cleaving linker. In some alternatives, the HER2 polypeptide comprises at least 95%, 96%, 97%, 98%, or 99% sequence identity to a polypeptide of an extracellular domain of HER2 polypeptide having a sequence of amino acids 563 to 652 of SEQ ID NO: 23 linked to a transmembrane domain, wherein the isolated polypeptide specifically binds to an antibody that binds to an epitope in Domain IV of Her2, and wherein the isolated polypeptide excludes the full length mature HER2. In some alternatives, the self-cleaving linker is a T2A linker having the sequence of L E G G G E G R G S L L T C G (SEQ ID NO: 26). In some alternatives, the chimeric antigen receptor comprises the amino acid sequence of SEQ ID NO: 2. In some alternatives, the chimeric antigen receptor comprises the amino acid sequence of SEQ ID NO: 25 (CD20CAR). In some alternatives, the host cell is selected from the group consisting of CD8 T cells, CD4 T cells, CD4 naïve T cells, CD8 naïve T cells, CD8 central memory cells, and CD4 central memory cells, or combinations thereof. In some alternatives, the host cell is autologous. In some alternatives, the host cell is antigen specific. In some alternatives, the growth factor is selected from IL-15, IL-7, IL-21, or IL-2, and combinations thereof. In some alternatives, the method further comprises selecting cells that express the Her2t polypeptide. In some alternatives, the cells are selected before culturing the cells in the medium. In some alternatives, the cells are selected using an antibody that binds to Domain IV of Her2. In some alternatives, the antibody is trastuzumab. In some alternatives, the method further comprises introducing a second isolated nucleic acid coding for a chimeric antigen receptor linked to a second genetic tag. In some alternatives, the method further comprises selecting cells expressing the second genetic tag. In some alternatives, the second genetic tag comprises EGFRt.

The preparation of transduced cells containing a CAR with a her2t marker sequence is described in the following.
Antibodies and Flow Cytometry.

Fluorochrome-conjugated isotype controls, anti-CD3, CD4, CD8, CD45, Her2, and streptavidin were obtained from BD Biosciences. Cetuximab (Erbitux) and trastuzumab (Herceptin) were purchased from the Seattle Children's Hospital. Erbitux and Herceptin were biotinylated (Pierce) or directly conjugated to APC (Solulink), according to manufacturer's instructions. Data acquisition was performed on an LSRFortessa (BD Biosciences), and the percentage of cells in a region of analysis was calculated using FlowJo data analysis software.
Cell Lines.

All cell lines were maintained in RPMI 1640 supplemented with 2 mM L-glutamine, 25 mM HEPES (Irvine Scientific), and 10% heat-inactivated fetal bovine serum (Hyclone or Atlas), unless otherwise noted. K562 erythroleukemia target cell lines were kindly provided by Dr. Stanley Riddell (Fred Hutchinson Cancer Research Center). Other cell lines H9 T lymphoblast, Raji (human Burkitt's lymphoma), and 293T (highly transfectable derivative of human embryonic kidney 293 cells) were supplied by the American Type Culture Collection. Epstein-Barr virus-transformed lymphoblastoid cell lines (TM-LCLs) as made from peripheral blood mononuclear cells (PBMCs) as previously described (Pelloquin et al. 1986). GFP:ffluc-expressing cell lines were transduced with GFP:ffluc_epHIV7 and sorted using the BD FACSJazz sorter.

Vector Construction and Preparation of Her2t or EGFRt-Encoding Lentivirus.

The second-generation 41BB-zeta CD19CAR-T2A-EGFRt_epHIV7 lentiviral construct was previously described (Hudecek et al. 2013). (Table 1)

The CD20CAR-T2A-EGFRt_epHIV7 contains a Leu16 (murine anti-human CD20) scFv fused to the human IgG4Hinge-CH3 (119 aa) spacer domain portion of IgG4 along with the same signaling components of the CD19CAR (4-1BB-zeta). (Table 9)

Her2t was synthesized by PCR, using pDONR223-ErbB2 (Addgene) as a template and the epHIV7 lentiviral vector as a recipient. (Tables 6 and 8) The final product, Her2t_epHIV7, contains the human granulocyte-macrophage colony stimulating factor receptor leader peptide (GMCSFRss) fused in frame to domain IV (aa 563-652) and the transmembrane spanning components of Her2 (aa 653-675). Her2t replaced EGFRt in the CD19CAR-T2A-EGFRt_epHIV7 construct by PCR and Gibson cloning. EGFRt was synthesized as previously described (Wang et al. 2011). (Table 7)

The CD19CAR-T2A-Her2t-, CD19CAR-T2A-EGFRt-, CD20CAR-T2A-EGFRt-, Her2t-, and EGFRt-encoding lentiviruses were produced in 293T cells using the packaging vectors pCHGP-2, pCMV-Rev2, and pCMV-G.
Generation of CAR-, Her2t-, and/or EGFRt-Expressing Cell Lines.

To generate CD4 or CD8 central memory T cells, human PBMCs were isolated over Ficoll-Paque (Pharmacia Biotech) from blood discard kits of healthy donors (Puget Sound Blood Center). PBMCs from each donor were split into two groups (CD4 or CD8 central memory T cell isolation) and subsequently AutoMACS depleted using CD4 or CD8 isolation kits and anti-CD45RA microbeads (Miltenyi Biotec), per the manufacturer's protocol. The depleted fraction was then positively selected on AutoMACS using anti-CD62L microbeads to produce CD4+CD45RO+CD62L+ or CD8+CD45RO+CD62L+ central memory T cells. Isolated cells were then stimulated with 50 U/ml interleukin-2 (IL-2), 2 ng/ml interleukin-15 (IL-15), and anti-CD3/CD28 beads (Life Technologies). Primary T cell lines were transduced on day 3 after activation using protamine sulfate (1:100 dilution) and a virus MOI of 1 followed by centrifugation at 800×g for 45 minutes at 32° C. All other cell lines were similarly transduced at a low cell passage number.

The Her2t+ or EGFRt+ subset of each cell line was enriched by immunomagnetic selection with biotin-conjugated Herceptin or Erbitux and anti-biotin microbeads (Miltenyi). Selected CD19 or CD20CAR+ T cells were expanded 12-18 days post transduction by stimulation with irradiated (8000 rad) TM-LCLs at a T cell:TM-LCL ratio of 1:7 in the presence of 50 U/ml IL-2 and 2 ng/ml of IL-15. CD19CAR-T2A-Her2t+/CD20CAR-T2A-EGFRt+ T cells were sorted using biotinylated Herceptin and anti-biotin multisort microbeads (Miltenyi) followed by bead removal, Erbitux-APC cell labeling, and anti-APC microbeads (Miltenyi).
Protein Analysis.

Cell lysis was carried out in RIPA buffer containing protease inhibitor cocktail. Cell lysates were analyzed by BCA assay (Pierce), equally loaded onto gels and western blots were probed with the primary antibodies Her2 and phospho-Her2 (Cell Signaling Technology), anti CD247 (CD3ζ), biotinylated Herceptin, or anti-β-actin (loading control). Secondary IRDye 800CW conjugated Streptavidin or goat anti-mouse or rabbit (LI-COR) was added as per the manufacturer's instructions. Blots were imaged on the Odyssey Infrared Imaging System (LI-COR).

Cytotoxicity, Cytokine Secretion, and Proliferation Assays.

Cytotoxicity: Four-hour chromium release assays were performed as previously described (Wang et al. 2011). Antibody-dependent cell-mediated cytotoxicity (ADCC) was determined using up to $2.5 \times 10^5$ Tcm cells expressing CD19CAR with Her2t marker, CD20CAR with EGFRt marker, CD19CAR-Her2t and CD20CAREGFRt, and CD19CAR with EGFRt as a marker sequence as effector cells in co-cultures with $5 \times 10^3$ $Cr^{51}$-labeled K562 cell expressing either CD19 or CD20.

Cytokine secretion: T cells ($5 \times 10^5$) were plated in triplicate with target cells at an E:T ratio of 2:1 in a 96-well plate and supernatants were analyzed by cytometric bead array using a Bio-Plex Human Cytokine Panel (Bio-Rad), according to the manufacturer's instructions.

Proliferation: T cells were labeled with 0.2 µM carboxyfluorescein succinimidyl ester (CFSE; Invitrogen), washed, and plated in triplicate with stimulator cells in medium without exogenous cytokines. After 72 hours of incubation, cells were labeled with anti-CD3 and live/dead stain, and subsequently analyzed by flow cytometry to assess cell division of viable CD3+ cells.

In Vivo T-Cell Engraftment and ADCC.

All mouse experiments were approved by the Animal Care and Use Committee of Seattle Children's Research Institute. NOD/Scid IL2RγCnull mice were obtained from The Jackson Laboratory or bred in-house.

Engraftment: Six- to 10-week old NOD/Scid IL2RγCnull mice were injected intravenously on day 0 with $10^7$ of either Her2t/EGFRt-negative (Mock) or Her2t or EGFRt-selected T cells and subcutaneously with $5 \times 10^6$ viable NS0-IL15 cells to provide a systemic supply of human IL-15 in vivo. Bone marrow was harvested from killed animals 14 days later, and cell suspensions were analyzed by flow cytometry using anti-CD45, live/dead, CD4, CD8, biotinylated Herceptin or Erbitux, and streptavidin-APC provided by BD Biosciences. Alternatively, femurs were fixed in 10% formalin for 24 hours, decalcified for 2 hours (Richard-Allan Scientific), and embedded in paraffin for immunohistochemical staining with anti-CD45 (DAKO), anti-EGFR (clone 31G7; Invitrogen) according to the manufacturer's instructions, or biotinylated Herceptin and SA-AF647 followed by counterstain with Hoechst. Similarly, $Her2^+$ or $Her2t^+$ cell lines were adhered to slides using poly-L-Lysine and then stained using biotinylated Herceptin and SA-AF647. Fluorescent images were acquired using the Nuance FX Biomarker Imaging System.

Statistical Analyses.

Statistical analyses were conducted using Prism Software (GraphPad). Student's t-tests were conducted as two-sided paired tests with a confidence interval of 95%, and results with a P value less than 0.05 were considered significant. Statistical analyses of survival were conducted by log-rank testing, and results with a P value less than 0.05 were considered significant.

Design and Initial Characterization of a Multifunctional Surface Epitope Based on Human ErbB2 (Her2).

The use and selection of homogenous immune cell products has been a limiting factor to the clinical success and reproducibility of adoptive therapy strategies. To this end, a non-immunogenic epitope based on human Her2, coined Her2t was designed, as a candidate genetic tag and tool for cellular engineering (FIG. 1A). Her2t is devoid of all Her2 intracellular components, yet contains the Her2 transmembrane region, a conformationally intact binding epitope recognized by the monoclonal antibody trastuzumab (Herceptin) and a GMCSFRss to facilitate surface expression (FIG. 1B). Three variants of the Her2t construct, one containing the full Her2 Domain IV and two minimal conformational epitopes designed based on the three dimensional structure of Her2 in complex with Herceptin (Garrett et al 2007; Cho et al 2003), were initially incorporated into the lentiviral packaging plasmid epHIV7 and characterized in CHO cells. The Her2t construct including amino acids 563-652 outlined in FIG. 1B displayed the greatest transient surface expression based on flow analysis using biotinylated Herceptin and a streptavidin-conjugated fluorophore and was therefore chosen for further downstream characterization (data not shown).

Her2t is a Viable and Functionally Inert Genetic Tag.

Following initial transient expression analysis, the Her2t-containing epHIV7 was subjected to VSV-g pseudotyped self-inactivating lentivirus production. The resultant virus was then transduced into multiple cell types resulting in 8.2-65% $Her2t^+$ populations (data not shown), with transduced K562 erythroleukemia cells (13.8% $Her2t^+$) as a representative (FIG. 2A). To assess the utility of Her2t as a target for the selective enrichment of transgene-endowed cell populations, the transduced K562 population was subjected to a two-step immunomagnetic purification process using biotinylated Herceptin and anti-biotin microbeads. This process consistently resulted in cell populations that were >95% $Her2t^+$ (FIG. 2B). Later titration experiments revealed that 1.2 ng or lower of biotinylated Herceptin was sufficient to maximally label $10^6$ $Her2t^+$ cells. (FIG. 2A).

Figure 2C:
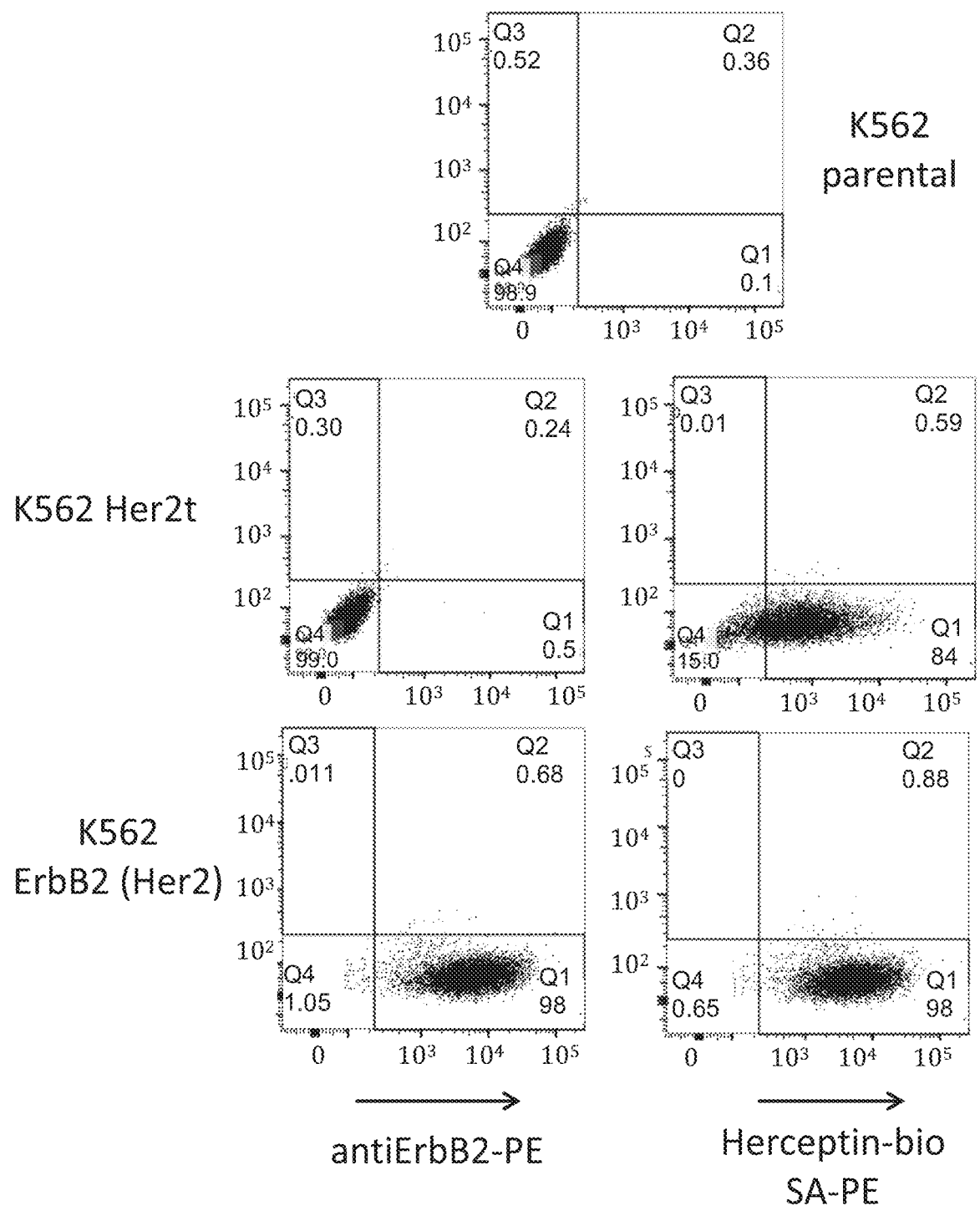

As displayed in our molecular model (FIG. 1A), Her2t is devoid of extracellular Domains I-III and contains a Domain IV binding epitope necessary for antibody recognition. It was therefore predicted that Her2t would be incapable of binding to commercial Her2 antibodies and would be uniquely recognized by Herceptin. Flow analyses confirmed that Herceptin could efficiently recognize and stain Her2t and full Her2-expressing K562 cells, while a commercial antibody was only able to recognize full Her2 (FIG. 2C).

Figure 2D:
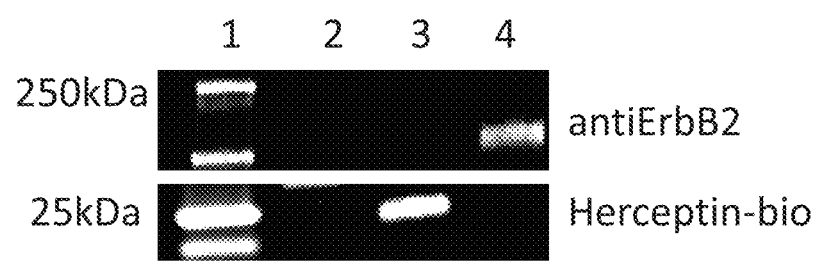

Western immunoblot analyses for Her2t and full Her2 were similarly carried out on Herceptin-selected $Her2t^+$ or full $Her2^+$ expressing cells, respectively. As expected, when a commercial Her2 antibody was used the full 185 kDa Her2 protein was only detected in lysates from full Her2-expressing cells. Likewise, Her2 phosphorylation was only detected in lysates from full Her2-expressing cells that were treated with neuregulin. A band for Her2t was only detected in $Her2t^+$ cell lysates when probed with biotinylated Herceptin (FIG. 2D).

Her2t is a Highly Stringent and Complementary Selection Epitope for T Cell Therapy.

A highly efficient selection epitope for chimeric antigen receptor (CAR) expressing T cell therapeutics coined EGFRt was previously identified (Wang et al 2011). It was examined whether the coordinate expression of Her2t in CAR-containing viral vectors might facilitate the clinical use of ex vivo engineered, broad-scope CAR therapeutics. Furthermore, Her2t diversifies the repertoire of available, non-immunogenic selection markers for CAR-redirected T cell therapeutics and can act as an alternative or supplement to EGFRt selection strategies (i.e. rendering a T cell bispecific against multiple candidate tumor antigens).

To evaluate the utility of Her2t in CAR therapy, a multidomain DNA construct composed of the previously described CD19CAR (Hudecek et al 2013) and a ribosomal skip T2A sequence to direct co-expression with Her2t was constructed (FIG. 1C). The resultant CD19CAR-T2A-Her2t construct was subsequently incorporated into epHIV7 and subjected to viral production as described earlier.

Figure 6:
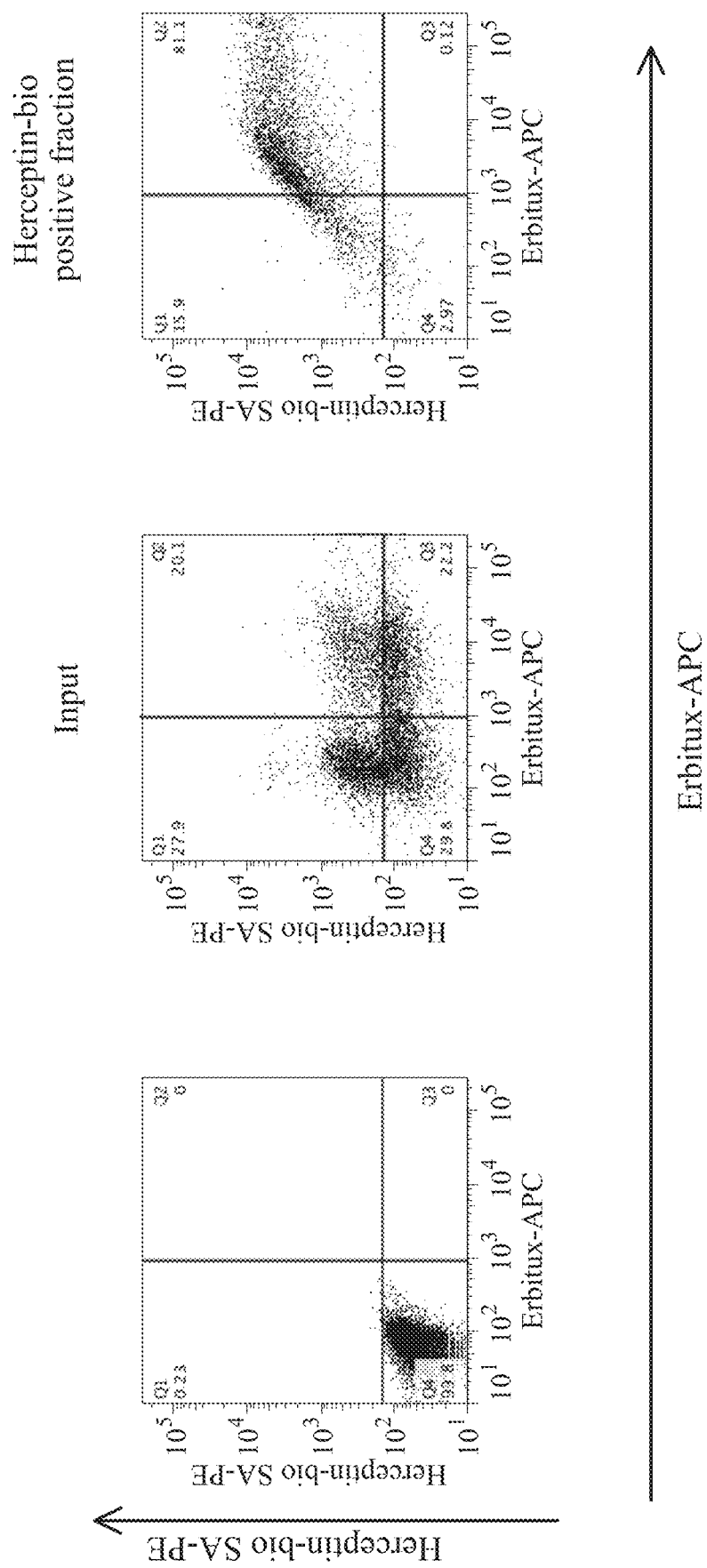
FIG. 6 relates to multisort purification of Her2t and EGFRt positive T cells. H9 cells ($5 \times 10^6$ parental, Her2t+, EGFRt+, or Her2t+/EGFRt+) were mixed together and then subjected to purification. The cells were initially purified based on biotinylated Herceptin and anti-biotin multisort beads. The multisort beads were then removed and the positive fraction subsequently subjected to purification based on Erbitux-APC and anti-APC microbeads. The final positive fraction was dual positive for Her2t and EGFRt.
Figure 6:
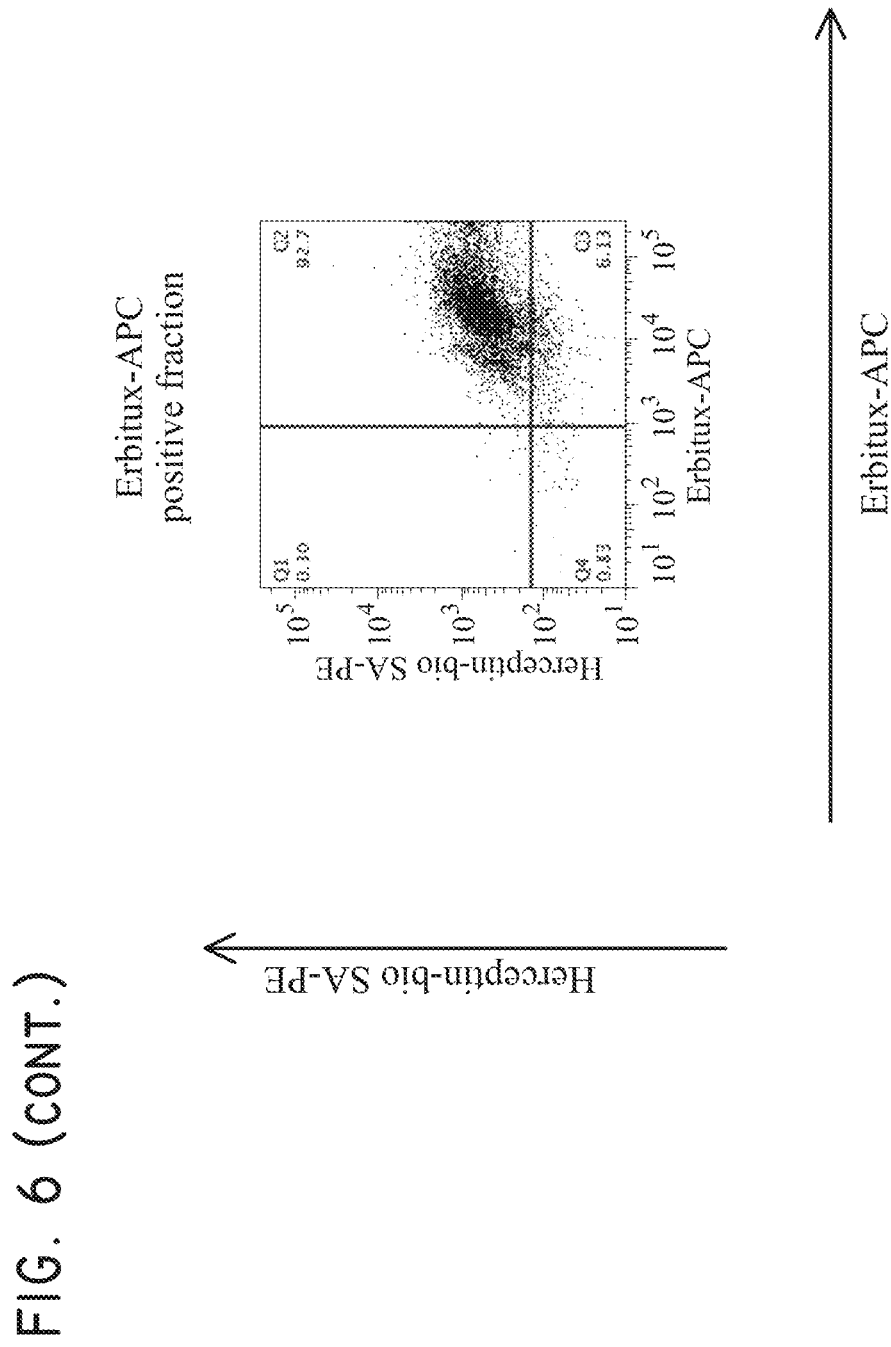

To assess the functionality of Her2t as a selection marker relative or in concert to EGFRt expression, CD4+ or CD8+ central memory (Tcm) cells (FIG. 3A) were transduced with a panel of CAR-T2A-Her2t and/or CAR-T2A-EGFRt containing viral vectors (FIG. 3B). The CD4+ or CD8+ Tcm transduced with a single CAR-containing vector were 22-72% Her2t+ or EGFRt+ pre-immunomagnetic selection using biotinylated Herceptin (Her2t) or Erbitux (EGFRt) and anti-biotin microbeads, but were consistently enriched to uniform purity (>90%) post-selection (FIG. 3B). Dual Her2t+ and EGFRt+ transduced cells were alternatively immunomagnetically sorted using a combination of multi-sort and anti-APC beads (Materials and Methods) resulting in >90% dual transgene-positive cells (FIG. 6).

Figure 3C:
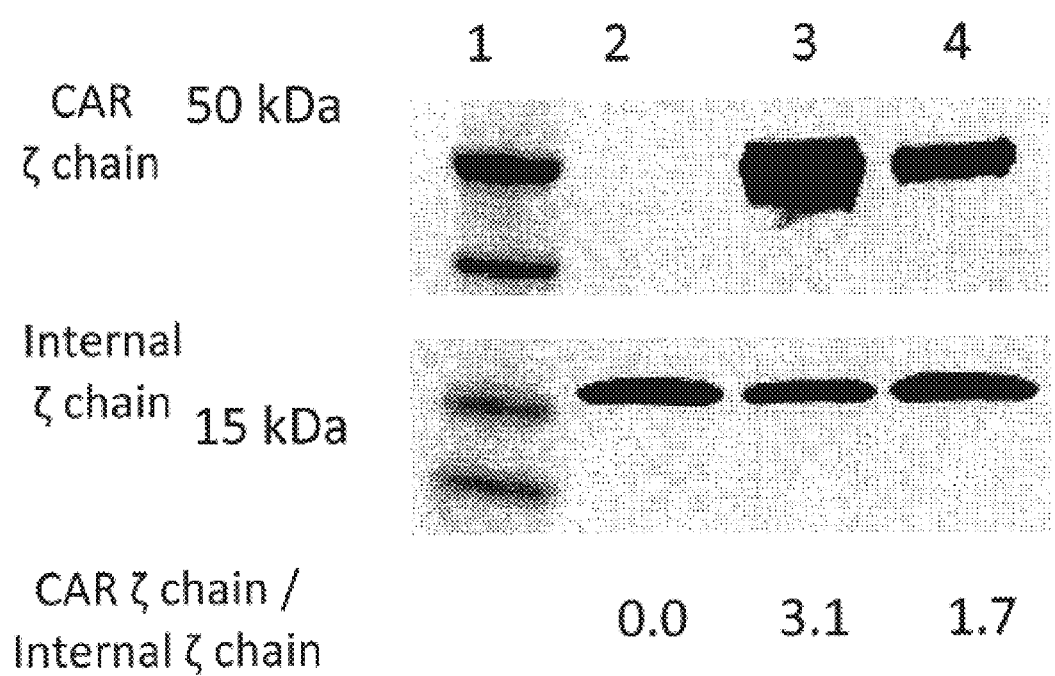

Alternatively, dual-transduced cell lines can be sorted using free biotin or streptavidin as an alternative to bead removal. Since flow mean fluorescence intensity (MFI) analyses indicated that Her2t-selected Tcm populations might express lower transgene levels relative to EGFRt-selected populations (FIG. 3B), we next asked whether Her2t levels directly correlated with lower CAR expression. To do this, CD19CAR-expressing Tcm that were selected by Her2t or EGFRt were lysed and cell lysates analyzed by CD3ζ targeted western blot analysis. Results demonstrate that Her2t-appended transgenes are selected at a higher expression level (e.g. about 2 fold) than EGFRt-appended transgenes (FIG. 3C). These results denote that Her2t allows for a more stringent selection process relative to EGFRt selection. The western blot analysis also demonstrated CD19CAR and CD20CAR co-expression in dual-selected Tcm (FIG. 3C).

Dual-Selected Tcm Maintain Effector Phenotype and Target Specificity In Vitro.

Figure 4A:
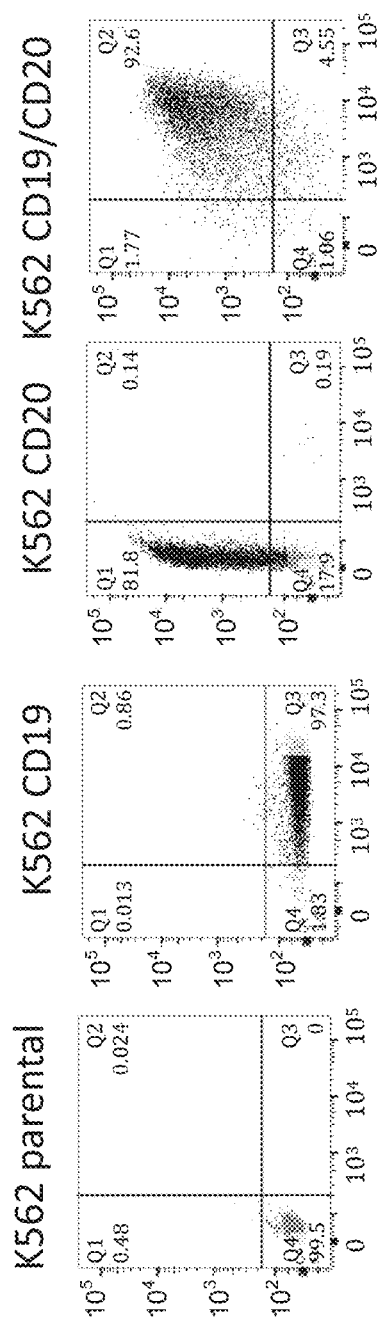
Figure 4B:
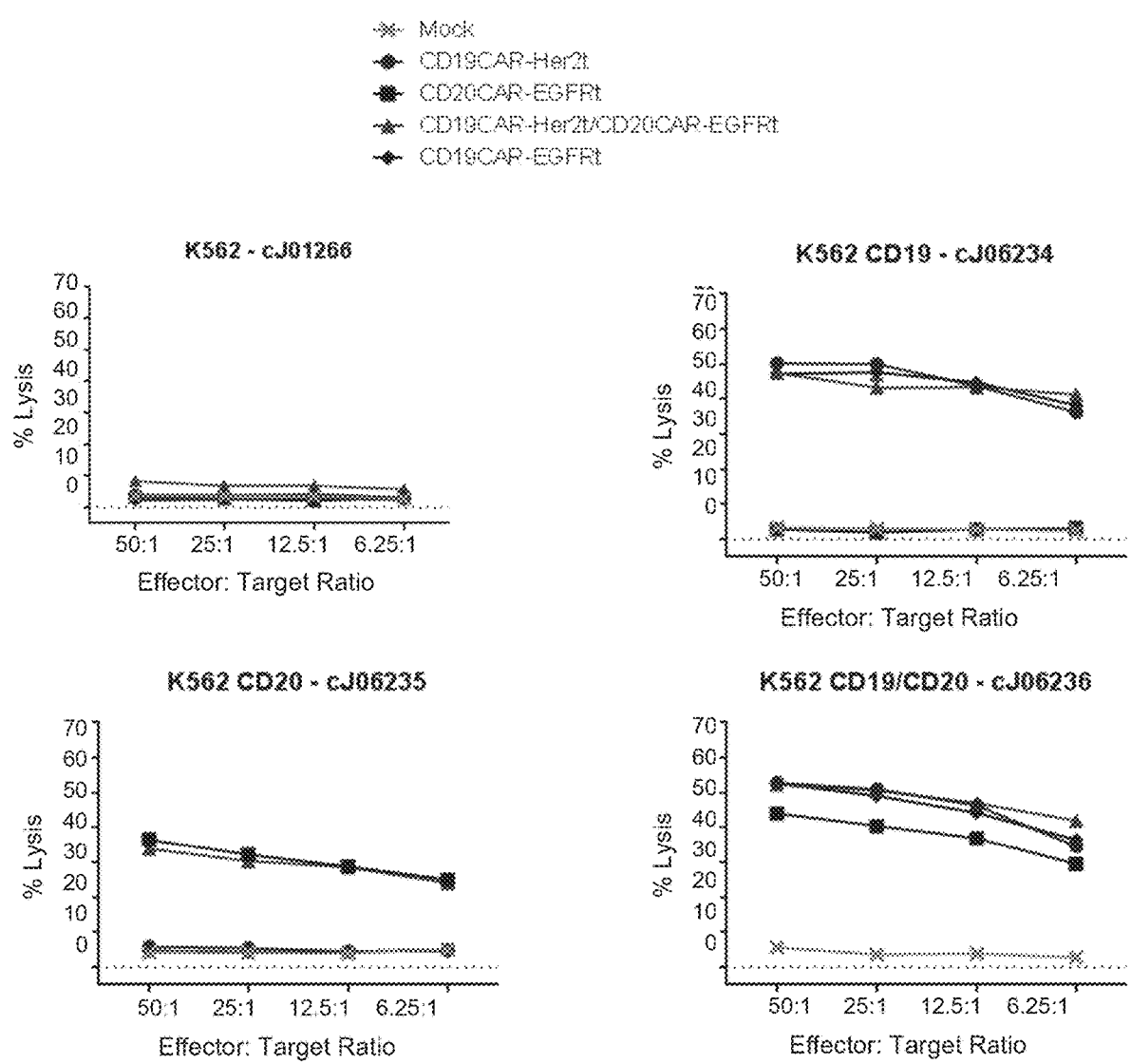

Multiple cancer types downregulate or mutate target antigens as a means to escape therapy. The simultaneous targeting of multiple tumor-associated antigens is therefore a promising therapeutic approach to overcome tumor escape and can broaden the therapeutic reach of T cell therapeutics. To assess whether the co-expression of two CARs (CD19- and CD20-CAR) mediated by surface marker (Her2t and EGFRt) selection could enhance the functional attributes of CAR redirected T cells, the in vitro function of dual CAR-expressing Tcm relative to their single CAR-expressing counterparts was analyzed. Cytotoxicity analyses showed that each CAR-redirected Tcm subset (CD19-, CD20- or CD19- and CD20-CAR expressing) conferred similar levels of specific lysis against K562 cells that express CD19, CD20, or both (FIG. 4A) but did not mediate recognition of the CD19−/CD20− parental K562 targets (FIG. 4B).

The paired functionality of the dual CAR-expressing Tcm against a K562 target panel was next tested (FIG. 4B) and demonstrate that only the dual CAR-expressing Tcm were able to confer specific lysis against all target expressing K562 cells. In contrast, the CD19- or CD20-specific CAR expressing Tcm cells were only able to trigger cytolytic activity against K562 cells expressing their cognate target antigens (FIG. 4B).

Figure 4C:
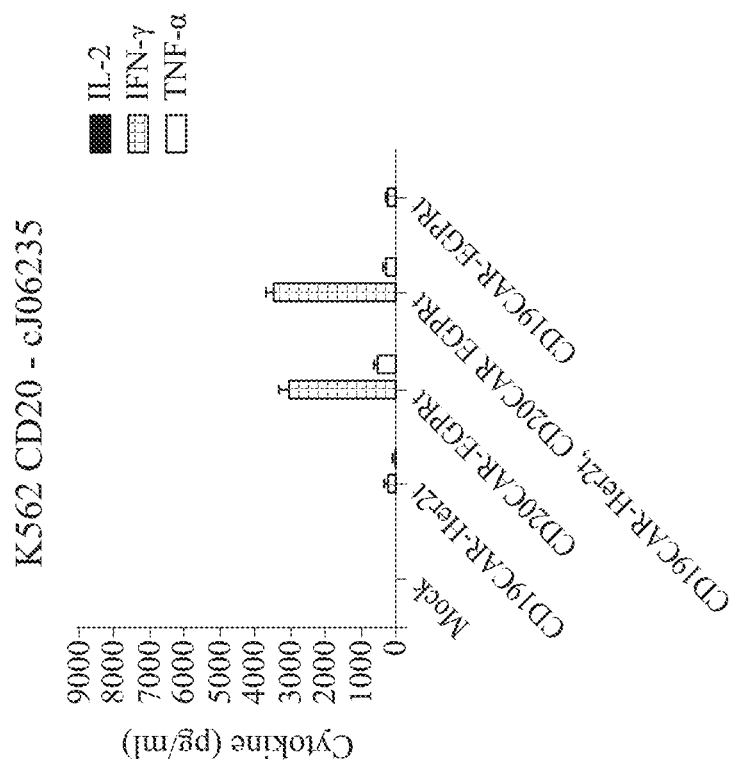
Figure 4C:
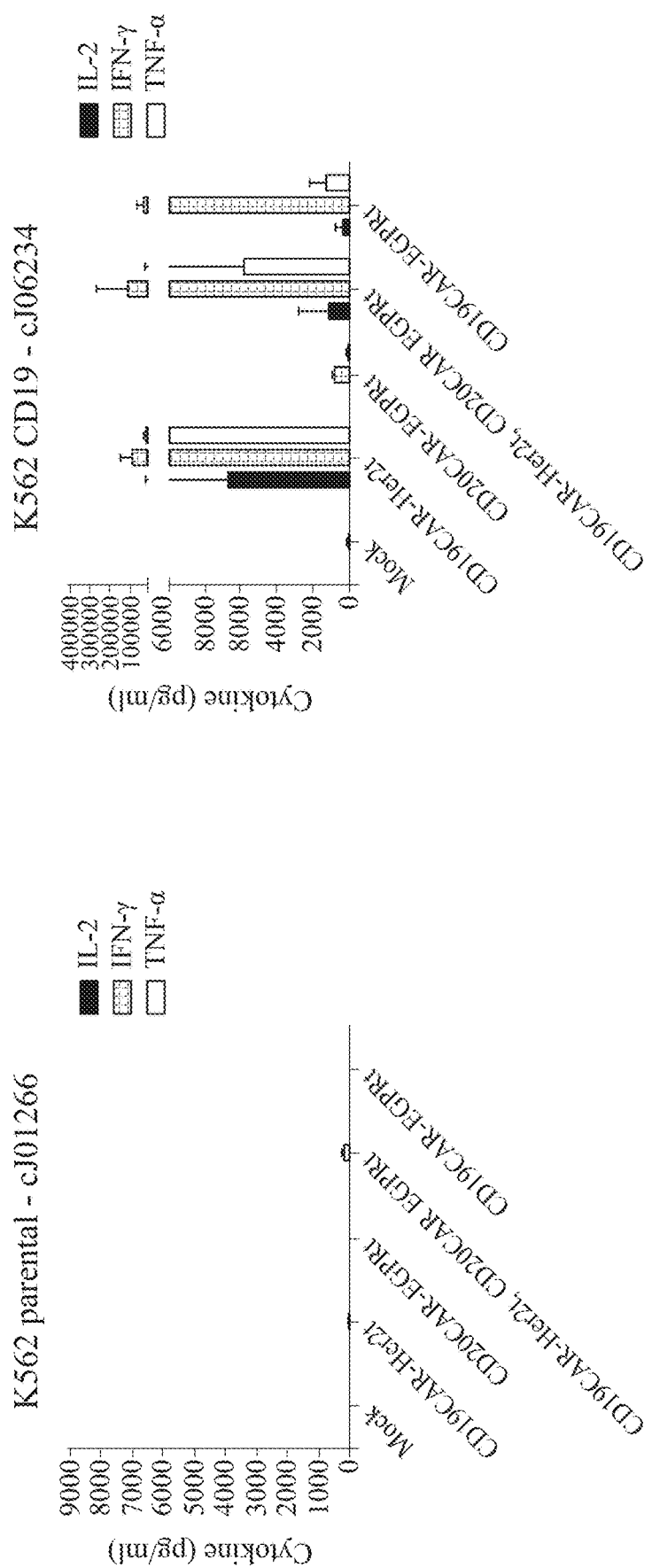

Quantitative analysis of cytokine production in response to stimulation with the K562 target panel demonstrate similar specificity. While no CAR-expressing Tcm was able to produce cytokines in response to co-culture with K562 parental cells, the dual CAR-expressing Tcm produced IL2, IFNγ and TNFα in response to co-culture with all target-expressing cells and cytokine production was restricted to K562/CD19-CD20 and K562/CD19 or K562/CD20 targets cells for single CAR-expressing Tcm. (FIG. 4C). These results indicate that only the dual CAR-expressing Tcm is bispecific for CD19 and CD20 and mediates activation and targeting of T cells upon encounter of either antigen alone. Interestingly, Her2t-selected CD19CAR-expressing Tcm produced a more diverse and enhanced cytokine profile (e.g. about 2-3 fold greater) relative to their EGFRt-selected counterpart. (FIG. 3D) This can be due to the stringent nature of Her2t selection and the resultant enhancement of total CAR expression in Her2t-selected Tcm.

Since CAR antitumor activity correlates with the proliferation and survival of transferred T cells, we chose to perform a CFSE dilution assay to analyze proliferation of CAR modified Tcm after engagement with their respective target(s). It was found that dual CAR expression promoted Tcm proliferation following stimulation at similar levels to CD19CAR-expressing Tcm.

Tracking of Adoptively Transferred Her2t+ T Cells by Flow Cytometry and Immunohistochemistry.

The majority of CAR therapy clinical trials to date have relied on PCR-based techniques to quantify gene-modified cell persistence post therapeutic dosing. The use of therapy specific genetic tags, such as Her2t, can further permit multiparameter phenotypic analysis and identify infused CAR T cell subsets that can correlate with therapeutic responses.

Figure 5A:
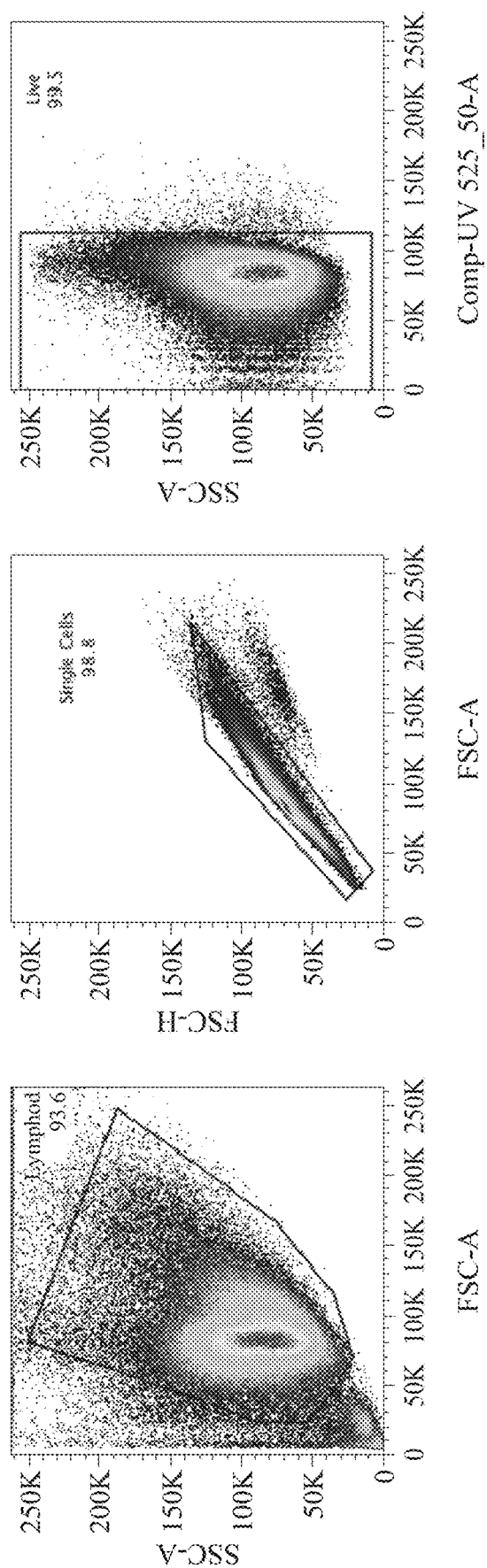
Figure 5B:
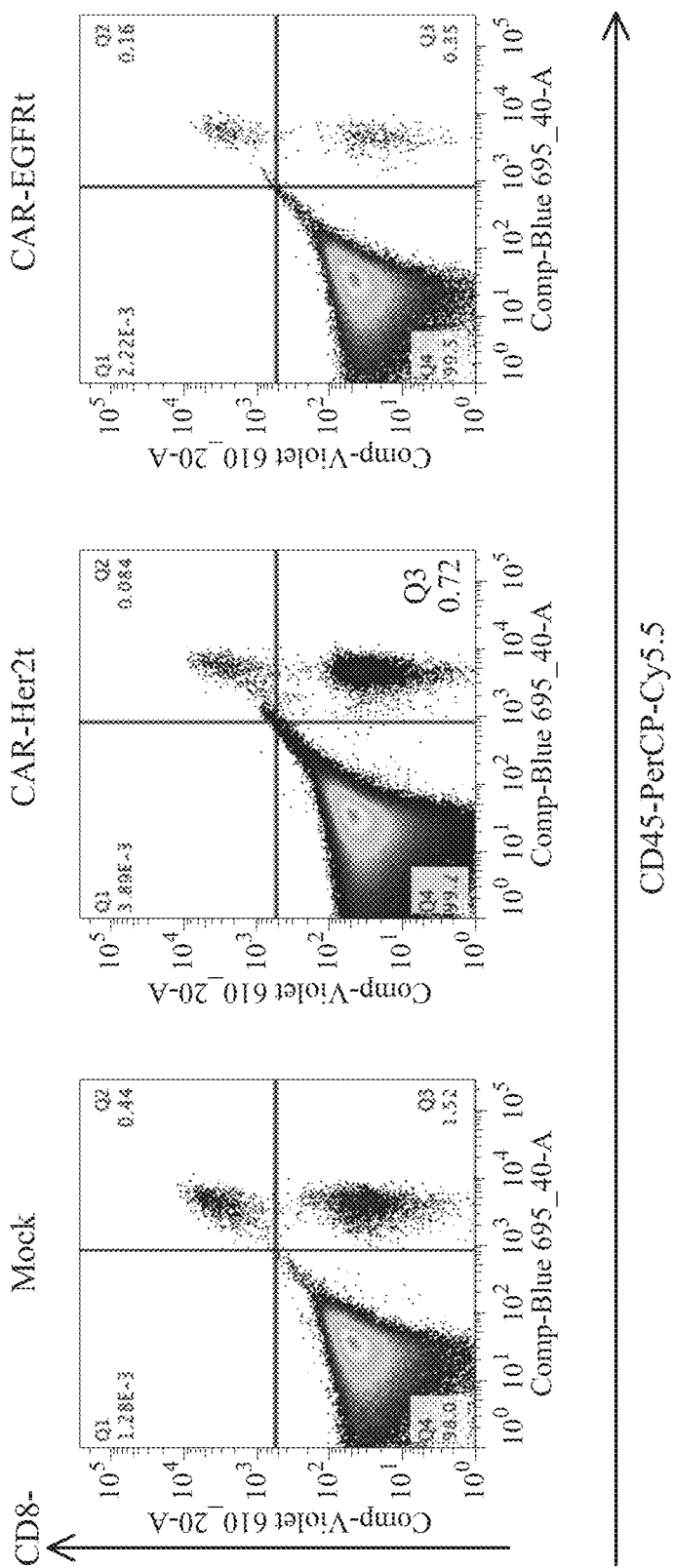
Figure 5C:
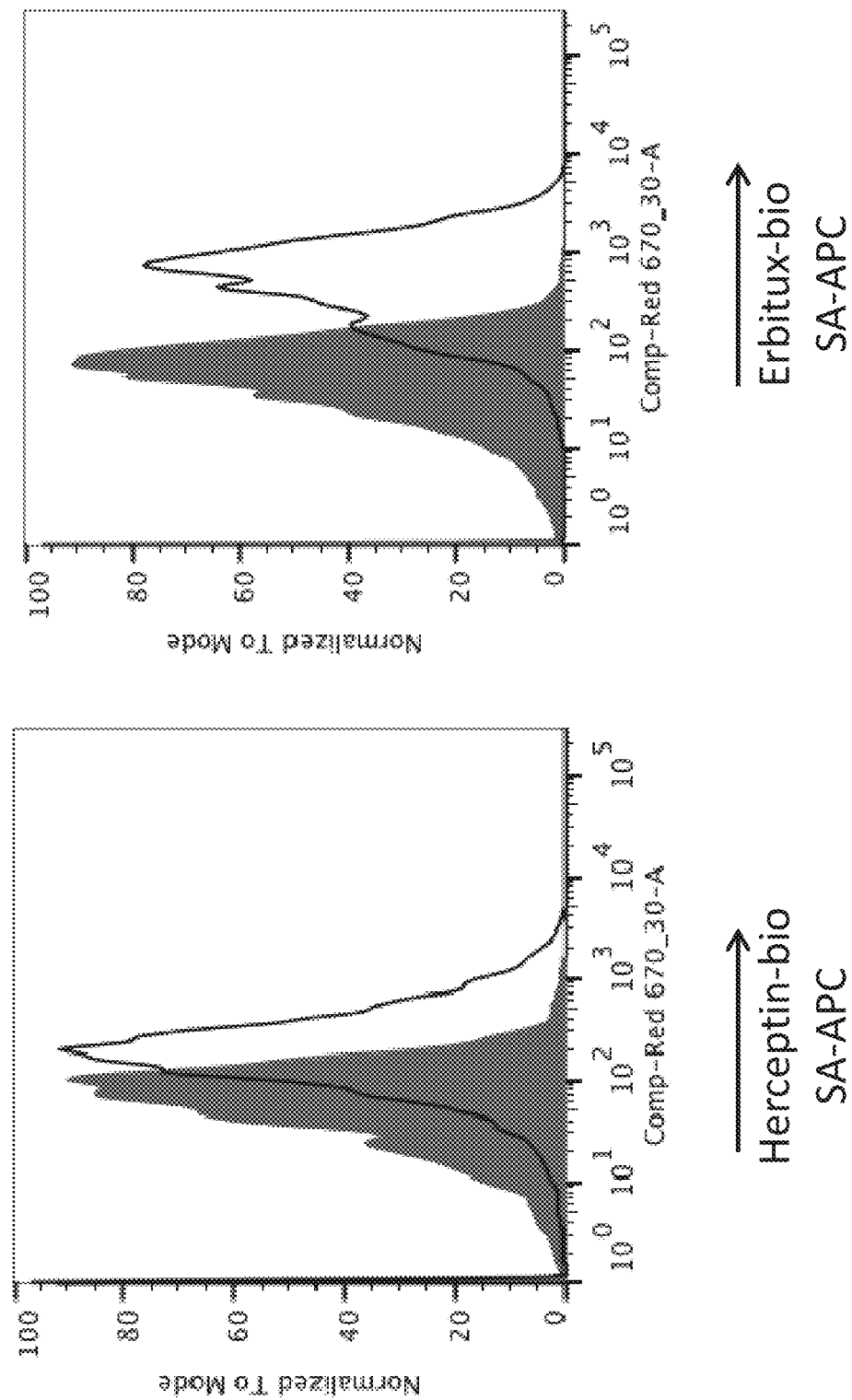

To test the utility of Her2t as a tracking agent in vivo, bone marrow specimens from NOD/Scid IL-2RγC$^{null}$ mice engrafted with CD19CAR+ Her2t+ CD4 and CD8 Tcm was harvested and subjected the processed samples to flow cytometric analysis. (FIG. 5A). Similar levels of CD45+ T cell engraftment were found in mice administered with marker-negative, Her2t+, and EGFRt+ cells (FIG. 5B). Of the CD45+ T cell subset, 11.7-45.7% were double stained for CD8 indicating a preferential expansion of CD4+ T cells. Furthermore, co-staining for Her2t using biotinylated Herceptin and APC-conjugated streptavidin allowed for the resolution of Her2t+ T cells from their Her2t-negative counterparts (FIG. 5C). These results demonstrate that Her2t is a viable tracking marker for adoptively transferred T cells.

It was next determined whether Her2t was a viable target for immunohistochemical (IHC) staining. As a preliminary study, Her2t+ cells were adhered to slides and stained with biotinylated Herceptin and a fluorochrome-conjugated streptavidin (FIG. 5D).

Herceptin Binding to Her2t Sensitizes Human T Cells to ADCC.

Incorporating a safety mechanism in administered T cells is a valuable feature should an adverse clinical event occur during therapy. An in vitro cytotoxicity analysis of Her2t+ or EGFRt+ T cells when co-cultured with GMCSF stimulated PBMCs and either Herceptin or Erbitux will be conducted.

H9 (T cells) cells (5×10$^6$ parental, Her2t+, EGFRt+, or Her2t+/EGFRt+) were mixed together and then subjected to purification. (FIG. 6). The cells were initially purified based on biotinylated Herceptin and anti-biotin multisort beads. The multisort beads were then removed and the positive fraction subsequently subjected to purification based on Erbitux-APC and anti-APC microbeads. The final positive fraction was dual positive for Her2t and EGFRt. (FIG. 6).

In this system, stimulated PBMCs will act as a source of effectors able to induce antibody dependent cellular cytotoxicity in the presence of antibody. The goal would be to selectively eliminate Her2t+ or EGFRt+ cells when Herceptin or Erbitux is added to the co-culture, respectively. These tests will be expanded in vivo using ffluc+ Tcm that co-express Her2t or EGFRt. In this setting, Tcm will be engrafted into NOD/Scid Il-2RγC$^{null}$ mice followed by the administration of Herceptin or Erbitux and freshly activated PBMCs. The in vivo engraftment and antibody-mediated elimination of transferred Tcm will be measured by in vivo biophotonic imaging. Herceptin or Erbitux-mediated elimination should be specific to Tcm expressing Her2t, EGFRt or both markers.

Combined Her2t and EGFRt Selection Confers Dual CAR Specificity In Vivo.

The goal for these experiments is to show selective antitumor activity in vivo. K562 ffluc$^+$ tumor cells that are CD19$^+$, CD20$^+$ or CD19/CD20$^+$ will be established by s.c. injection into the left or right flank of NOD/Scid IL-2RγC$^{null}$ mice. CD19CAR-Her2t, CD19CAR-EGFRt, CD20CAR-EGFRt or CD19CAR-Her2t and CD20CAR expressing Tcm will be injected intravenously following tumor establishment and T cell specificity will be determined by biophotonic imaging. Loss of tumor luciferase activity (total photon flux) will indicate tumor regression.

Tumor regression should occur for all tumor targets when mice are treated with the dual CAR-expressing Tcm, while only CD19 or CD20-expressing K562 tumors should regress when mice are treated with Tcm expressing their cognate CAR. Alternatively, CD19$^+$, CD20$^+$ or CD19/CD20$^+$K562 cells will be established as before and ffluc$^+$CAR$^+$ Tcm will be administered post tumor establishment. Tcm localization based on CAR-specificity will be determined by biophotonic imaging. The dual-selected Her2t$^+$EGFRt$^+$ T cells should localize to both flanks irrespective of target antigen on the K562 tumors, while CD19 or CD20CAR expressing cells should localized to their target antigen specific K562 tumor. Introduction of a Linker Domain (Her2tG) Between the Her2 Domain IV and the Transmembrane Domain Allows for Enhanced Binding to the Antibody Herceptin.

Figure 7:
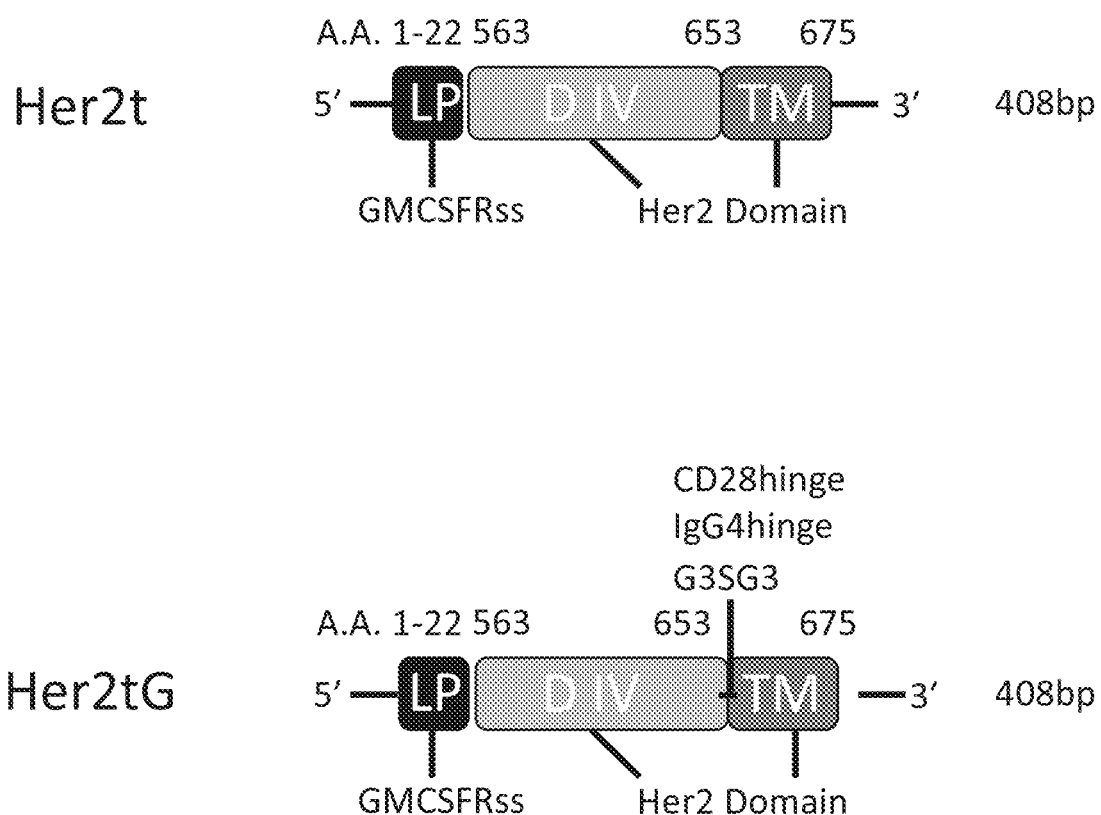
FIG. 7 depicts three variants of Her2t (CD28hinge, IgG4hinge or Her2tG) which were designed to enhance binding to the antibody Herceptin. Shown is a general schematic indicating where the new sequences were inserted into Her2t.
Figure 8:
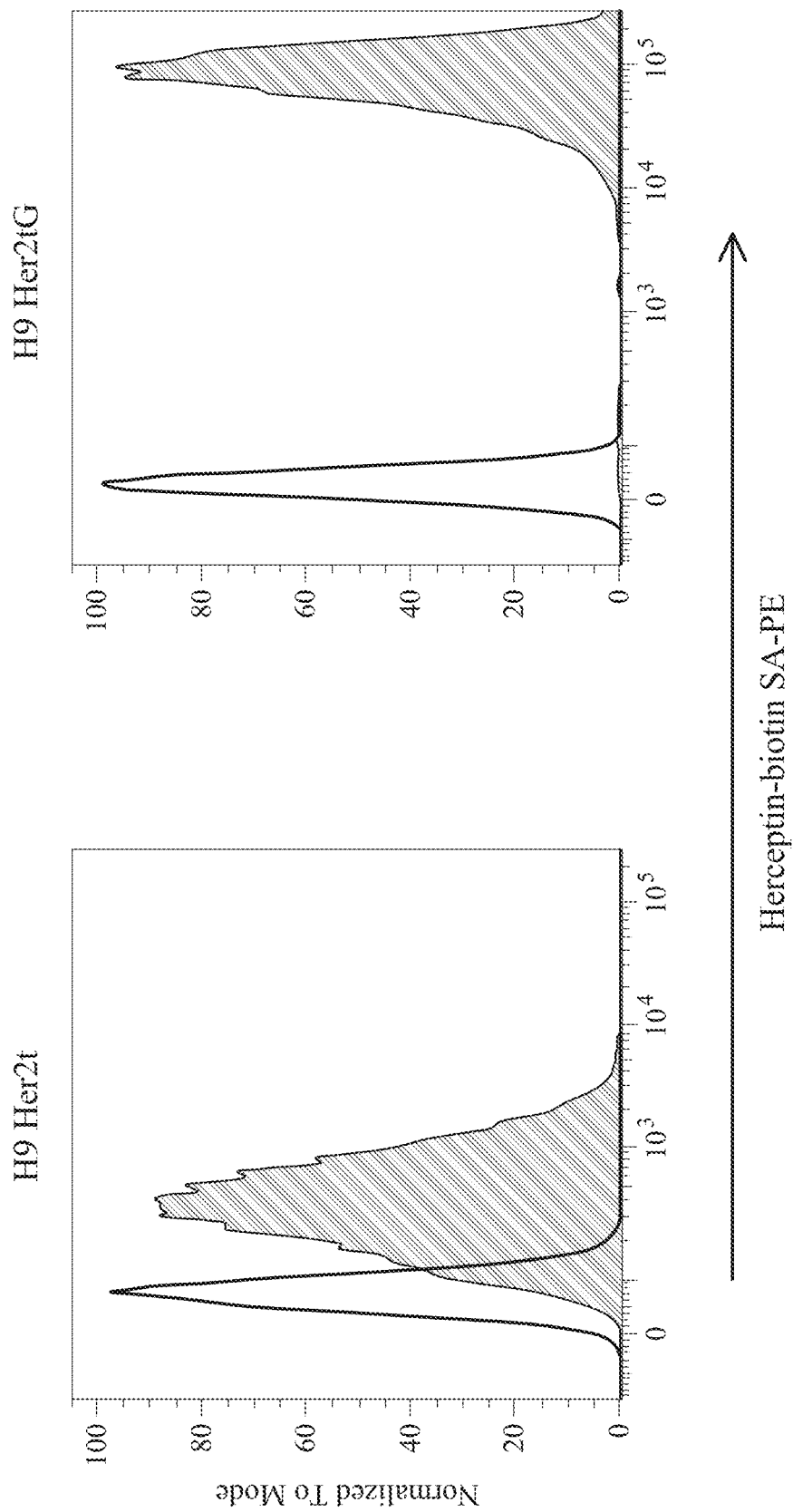
FIG. 8 depicts Her2tG displays enhanced binding to Herceptin. H9 cells were transduced with lentivirus at an MOI of 1 with Her2t or Her2tG. Transduced cells were then purified by biotinylated Herceptin and anti-biotin microbeads according provided wherein the host cell is antigen specific. In some alternatives, the cell is an effector memory T cell.
Figure 9:
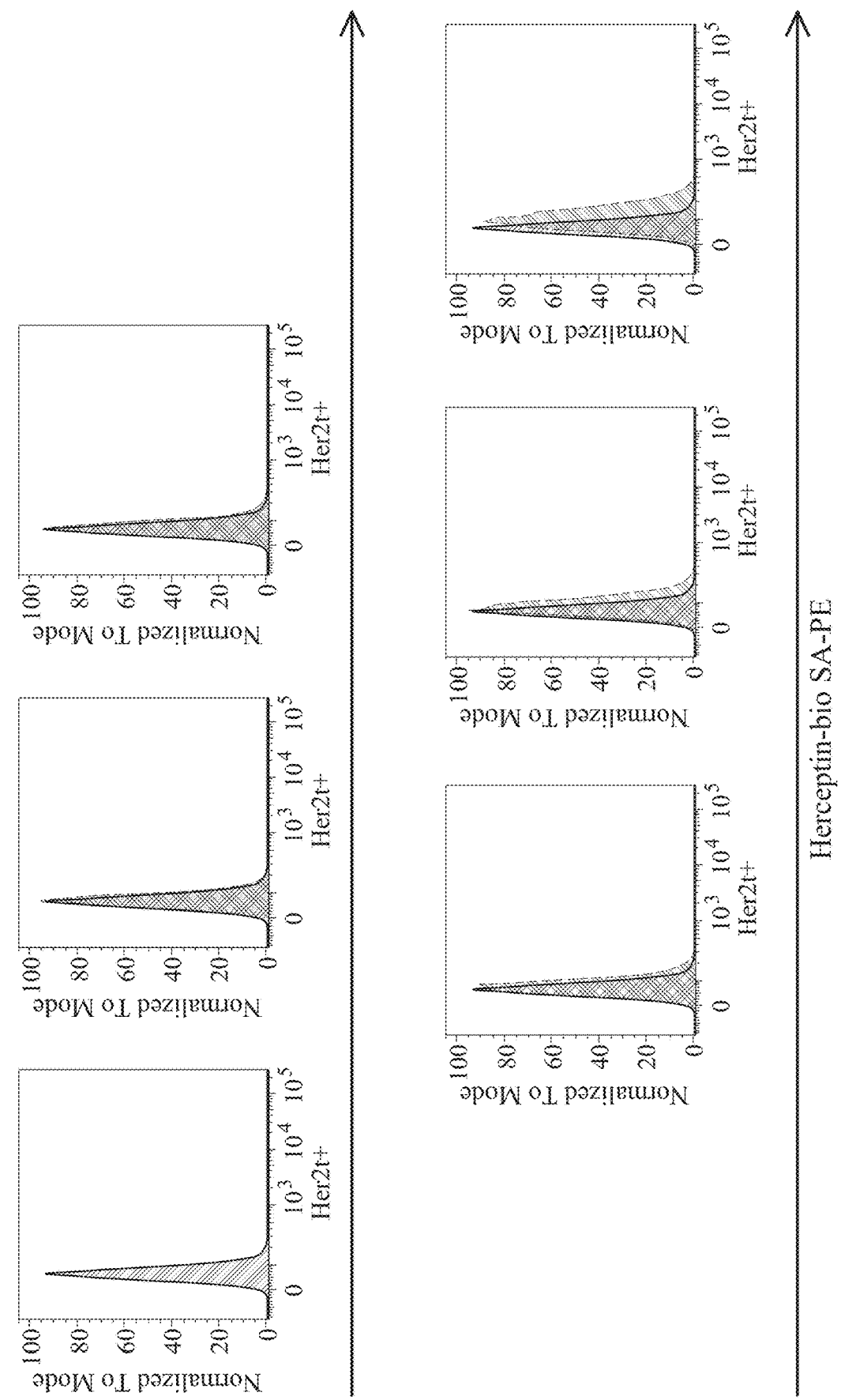
Figure 9:
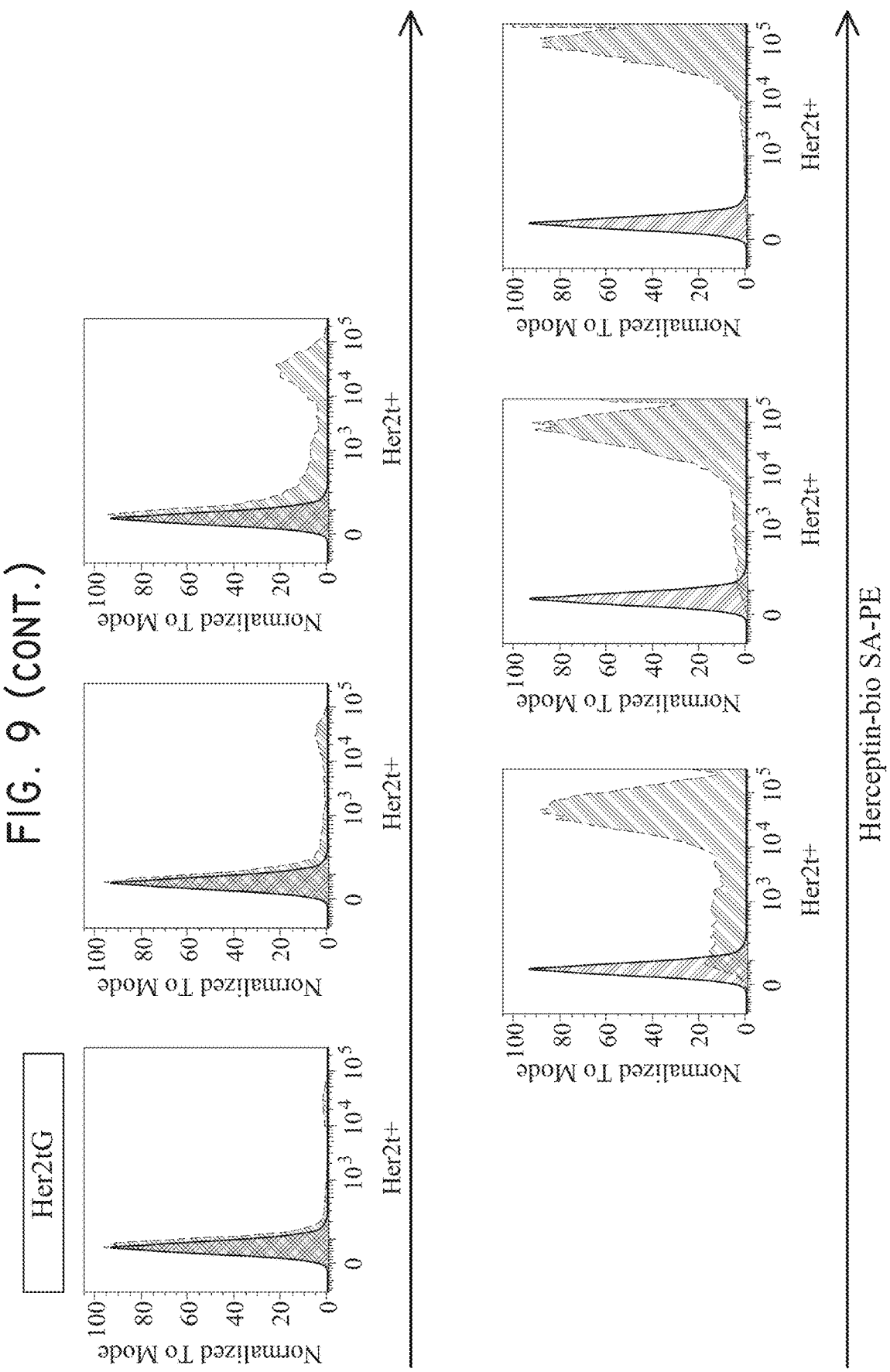

As shown in FIG. 7, are schematics of the primary sequence of Her2t and Her2tG. Her2tG differs from Her2t with the addition of a linker sequence between the Her2 domain IV and the transmembrane region and comprises the sequence GGGSGGGS (SEQ ID NO: 45) and the construct is designated as Her2tG. H9 cells were transduced with lentivirus at an MOI of 1 with Her2t or Her2tG. Transduced cells were then purified by biotinylated Herceptin and anti-biotin microbeads according to the manufacturers' protocol. The purified populations were later stained for Her2t or Her2tG using biotinylated Herceptin and streptavidin-PE. Histograms display greater binding to Her2tG (FIG. 8). As shown in FIG. 9, H9 cells were transduced with lentivirus at 0.05, 0.1, 0.25, 0.5, 1 and 3 ul (left to right) and then analyzed for Herceptin binding five days later. The Her2t variant Her2t(CD28hinge) was able to bind Herceptin at levels similar to the original Her2t (Her2t staining not shown but based on prior experience). Her2t(IgG4hinge) enhanced Herceptin binding relative to Her2t or Her2t(CD28hinge), while the Her2tG variant had the greatest capacity to bind Herceptin and stain transduced H9 cells.

As shown from the experiments, a linker (SEQ ID NO: 45) between Domain IV and the transmembrane domain of Her2t led to the construct Her2tG. The linker is used to induce flexibility between protein domains. In other examples, the scFv of many CARs contain four consecutive G3S subunits placed between the Vh and Vl domains of the CAR's scFv. This allows for flexibility in folding of the two scFv domains. The rational here is that two G3S linker subunits would suffice in being able to induce the same amount of flexibility for Her2tG.

Two G3S linker subunits (SEQ ID NO: 45) was also used to mimic the spacer length of the CD28hinge and IgG4hinge. Both the CD28hinge and IgG4hinge have been used as spacers between the scFv and transmembrane region in CARs that are functional. Both the CD28hinge and IgG4hinge contain a cysteine that help in dimerization. While helpful for CARs, this dimerization may inhibit the flexibility of Her2t and therefore not allow for as significant recognition to Herceptin. The advantage of using two G3S linkers (SEQ ID NO: 45) over three or four was to limit vector payload, eliminate potentially unnecessary sequences and at the same time achieve enhanced functionality.

A multi-purpose cell surface marker designated Her2t is described. This novel marker contains only 113 of the 1255 amino acids that compose full-length Her2 and is devoid of all extra or intracellular domains responsible for intact Her2 cell signaling. Hematopoietic cells lack Her2 expression making Her2t a prime candidate transgene selection marker that by design is rendered functionally inert yet able to refine donor T cells into homogenous, transgene-expressing therapeutic products. The design of Her2t comprises fusion of the N-terminal Her2t fragment to the leader peptide of the human GM-CSF receptor-α chain. This fusion helps facilitate Her2t surface expression and allows for the minimal binding epitope to be uniquely recognized by the pharmaceutical grade monoclonal antibody trastuzumab (Herceptin).

It was demonstrated that due to its minimal cDNA footprint Her2t can be expressed alone or coordinately incorporated into self-inactivating lentiviral vectors alongside biologically active transgenes, namely a chimeric antigen receptor (CAR). Coordinate transgene expression levels were attained by appending Her2t to the CAR via a T2A ribosomal skip linker and were verified by flow and western blot analysis of Her2t-purified CD8 central memory T cells. Furthermore, it was also demonstrated that Her2t is a highly stringent selection epitope that, in comparison to EGFRt selection strategies, allows for the ex vivo selection of T cells with greater CAR expression and effector cytokine production. This characteristic can be advantageous when higher transgene expression levels are desired, as can be the case when expanding CAR therapy to the treatment of multiple tumor types.

In addition to equipping T cells with elevated transgene expression levels, rendering an individual T cell bispecific against multiple tumor antigens can prove clinically beneficial. Indeed, the down regulation or mutation of target antigens is commonly observed in multiple cancer types necessitating the implementation of strategies beyond therapy driven by a single CAR. Along these lines, it was demonstrated that Her2t is a complementary selection epitope to EGFRt that, when each selection epitope is appended to a CAR, can facilitate the multisort purification of dual-CAR expressing T cells. Similar cytotoxic activity and effector cytokine production between single and dual-CAR expressing T cells demonstrate that the individual or concerted expression of Her2t and EGFRt does not result in any overt functional impairment.

Herceptin is amenable to biotinylation or chemical conjugation. As formulated for commercial use, Herceptin is reconstituted in clinical grade H$_2$O and retains Her2-specific high affinity binding post biotinylation. This, combined with the availability of cGMP grade anti-biotin microbeads (Miltenyi Biotec), enables the selection of therapeutically relevant Her2t$^+$ cells on a CliniMACS device. It was demonstrated that cells as low as 13.8% positive for Her2t can be immunomagnetically enriched to >90% purity. Furthermore, the results demonstrate that biotinylated Herceptin can be coupled with antibodies targeted against T cell markers to permit multiparameter phenotypic analysis and track the in vivo distribution of therapeutic, CAR expressing T cells.

The therapeutic reach of CAR immunotherapy is rapidly expanding beyond its initial success with the treatment of blood borne tumors. Alternative genetic tags that are inherently non-immunogenic, unique to T cell populations and highly efficient at selection are clearly needed. Her2t encompasses these aforementioned characteristics and diversifies the repertoire of selection epitopes to be used for CAR therapy. Furthermore, Her2t is a prime candidate for the concerted selection of CAR therapeutics equipped with multiplexed genetic systems.

An advantage of using Her2t is for its diminutive size. As such Her2t has the advantage of packing efficiency with even bigger constructs. In order to take advantage of the system it is preferred to have the construct less than 5 kb. In some alternatives, the size of the construct is 5, 6, 7, 8, 9, 10, 11, 12, 13, 14, 14.9 Kb, or any size in between any two of the construct size listed. The low size is necessary as constructs above 15 kb may run the risk of having low titers.

The foregoing is illustrative of the present invention, and is not to be construed as limiting thereof. The invention is defined by the following claims, with equivalents of the claims to be included therein. All references and documents referred to herein are hereby incorporated by reference.

TABLE 1

CD19CAR

```
        GMCSFRss
DNA: ATGCTGCTGCTGGTGACCAGCCTGCTGCTGTGCGAGCTGCCCCACCCCGCC
AA:   M   L   L   L   V   T   S   L   L   L   C   E   L   P   H   P   A

CD19scFv
DNA: TTTCTGCTGATCCCC:GACATCCAGATGACCCAGACCACCTCCAGCCTGAGC
AA:   F   L   L   I   P   D   I   Q   M   T   Q   T   T   S   S   L   S

DNA: GCCAGCCTGGGCGACCGGGTGACCATCAGCTGCCGGGCCAGCCAGGACATC
AA:   A   S   L   G   D   R   V   T   I   S   C   R   A   S   Q   D   I

DNA: AGCAAGTACCTGAACTGGTATCAGCAGAAGCCCGACGGCACCGTCAAGCTG
AA:   S   K   Y   L   N   W   Y   Q   Q   K   P   D   G   T   V   K   L

DNA: CTGATCTACCACACCAGCCGGCTGCACAGCGGCGTGCCCAGCCGGTTTAGC
AA:   L   I   Y   H   T   S   R   L   H   S   G   V   P   S   R   F   S

DNA: GGCAGCGGCTCCGGCACCGACTACAGCCTGACCATCTCCAACCTGGAACAG
AA:   G   S   G   S   G   T   D   Y   S   L   T   I   S   N   L   E   Q

DNA: GAAGATATCGCCACCTACTTTTGCCAGCAGGGCAACACACTGCCCTACACC
AA:   E   D   I   A   T   Y   F   C   Q   Q   G   N   T   L   P   Y   T

DNA: TTTGGCGGCGGAACAAAGCTGGAAATCACCGGCAGCACCTCCGGCAGCGGC
AA:   F   G   G   G   T   K   L   E   I   T   G   S   T   S   G   S   G

DNA: AAGCCTGGCAGCGGCGAGGGCAGCACCAAGGGCGAGGTGAAGCTGCAGGAA
AA:   K   P   G   S   G   E   G   S   T   K   G   E   V   K   L   Q   E

DNA: AGCGGCCCTGGCCTGGTGGCCCCCAGCCAGAGCCTGAGCGTGACCTGCACC
AA:   S   G   P   G   L   V   A   P   S   Q   S   L   S   V   T   C   T

DNA: GTGAGCGGCGTGAGCCTGCCCGACTACGGCGTGAGCTGGATCCGGCAGCCC
AA:   V   S   G   V   S   L   P   D   Y   G   V   S   W   I   R   Q   P

DNA: CCCAGGAAGGGCCTGGAATGGCTGGGCGTGATCTGGGGCAGCGAGACCACC
AA:   P   R   K   G   L   E   W   L   G   V   I   W   G   S   E   T   T

DNA: TACTACAACAGCGCCCTGAAGAGCCGGCTGACCATCATCAAGGACAACAGC
AA:   Y   Y   N   S   A   L   K   S   R   L   T   I   I   K   D   N   S

DNA: AAGAGCCAGGTGTTCCTGAAGATGAACAGCCTGCAGACCGACGACACCGCC
AA:   K   S   Q   V   F   L   K   M   N   S   L   Q   T   D   D   T   A

DNA: ATCTACTACTGCGCCAAGCACTACTACTACGGCGGCAGCTACGCCATGGAC
AA:   I   Y   Y   C   A   K   H   Y   Y   Y   G   G   S   Y   A   M   D

IgG4hinge
DNA: TACTGGGGCCAGGGCACCAGCGTGACCGTGAGCAGC:GAGAGCAAGTACGGA
AA:   Y   W   G   Q   G   T   S   V   T   V   S   S   E   S   K   Y   G CD28tm
DNA: CCGCCCTGCCCCCCTTGCCCT:ATGTTCTGGGTGCTGGTGGTGGTCGGAGGC
AA:   P   P   C   P   P   C   P   M   F   W   V   L   V   V   V   G   G DNA: GTGCTGGCCTGCTACAGCCTGCTGGTCACCGTGGCCTTCATCATCTTTTGG
AA:   V   L   A   C   Y   S   L   L   V   T   V   A   F   I   I   F   W 41BB
DNA: GTG:AAACGGGGCAGAAAGAAACTCCTGTATATATTCAAACAACCATTTATG
AA:   V   K   R   G   R   K   K   L   L   Y   I   F   K   Q   P   F   M
```

TABLE 1 -continued

CD19CAR

```
DNA: AGACCAGTACAAACTACTCAAGAGGAAGATGGCTGTAGCTGCCGATTTCCA
AA:   R  P  V  Q  T  T  Q  E  E  D  G  C  S  C  R  F  P
```

CD3Zeta
```
DNA: GAAGAAGAAGAAGGAGGATGTGAACTGCGGGTGAAG:TTCAGCAGAAGCGCC
AA:   E  E  E  E  G  G  C  E  L  R  V  K  F  S  R  S  A DNA: GACGCCCCTGCCTACCAGCAGGGCCAGAATCAGCTGTACAACGAGCTGAAC
AA:   D  A  P  A  Y  Q  Q  G  Q  N  Q  L  Y  N  E  L  N DNA: CTGGGCAGAAGGGAAGAGTACGACGTCCTGGATAAGCGGAGAGGCCGGGAC
AA:   L  G  R  R  E  E  Y  D  V  L  D  K  R  R  G  R  D DNA: CCTGAGATGGGCGGCAAGCCTCGGCGGAAGAACCCCCAGGAAGGCCTGTAT
AA:   P  E  M  G  G  K  P  R  R  K  N  P  Q  E  G  L  Y DNA: AACGAACTGCAGAAAGACAAGATGGCCGAGGCCTACAGCGAGATCGGCATG
AA:   N  E  L  Q  K  D  K  M  A  E  A  Y  S  E  I  G  M DNA: AAGGGCGAGCGGAGGCGGGGCAAGGGCCACGACGGCCTGTATCAGGGCCTG
AA:   K  G  E  R  R  R  G  K  G  H  D  G  L  Y  Q  G  L DNA: TCCACCGCCACCAAGGATACCTACGACGCCCTGCACATGCAGGCCCTGCCC
AA:   S  T  A  T  K  D  T  Y  D  A  L  H  M  Q  A  L  P
(SEQ ID NO: 46)
```

T2A
```
DNA: CCAAGG:CTCGAGGGCGGCGGAGAGGGCAGAGGAAGTCTTCTAACATGCGGT
(SEQ ID NO: 2)
AA:   P  R  L  E  G  G  G  E  G  R  G  S  L  L  T  C  G
(SEQ ID NO: 1)

DNA: GACGTGGAGGAGAATCCCGGCCCTAGG
```

TABLE 2

Uniprot P10747 CD28 (SEQ ID NO: 3)

```
         10         20         30         40
MLRLLLALNL FPSIQVTGNK ILVKQSPMLV AYDNAVNLSC 50         60         70         80
KYSYNLFSRE FRASLHKGLD SAVEVCVVYG NYSQQLQVYS 90        100        110        120
KTGFNCDGKL GNESVTFYLQ NLYVNQTDIY FCKIEVMYPP 130        140        150        160
PYLDNEKSNG TIIHVKGKHL CPSPLFPGPS KPFWVLVVVG 170        180        190        200
GVLACYSLLV TVAFIIFWVR SKRSRLLHSD YMNMTPRRPG 210        220
PTRKHYQPYA PPRDFAAYRS
```

1-18 signal peptide
19-152 extracellular domain
153-179 transmembrane domain
180-220 intracellular domain
Position 186-187 LL-GG

TABLE 3

Uniprot Q07011 4-1BB (SEQ ID NO: 4)

```
         10         20         30         40
MGNSCYNIVA TLLLVLNFER TRSLQDPCSN CPAGTFCDNN 50         60         70         80
RNQICSPCPP NSFSSAGGQR TCDICRQCKG VFRTRKECSS
```

TABLE 3 -continued

Uniprot Q07011 4-1BB (SEQ ID NO: 4)

```
         90        100        110        120
TSNAECDCTP GFHCLGAGCS MCEQDCKQGQ ELTKKGCKDC 130        140        150        160
CFGTFNDQKR GICRPWTNCS LDGKSVLVNG TKERDVVCGP 170        180        190        200
SPADLSPGAS SVTPPAPARE PGHSPQIISF FLALTSTALL 210        220        230        240
FLLFFLTLRF SVVKRGRKKL LYIFKQPFMR PVQTTQEEDG

250
CSCRFPEEEE GGCEL
```

1-23 signal peptide
24-186 extracellular domain
187-213 transmembrane domain
214-255 intracellular domain

TABLE 4

Uniprot P20963 human CD3ζ isoform 3 (SEQ ID NO: 5)

```
         10         20         30         40
MKWKALFTAA ILQAQLPITE AQSFGLLDPK LCYLLDGILF 50         60         70         80
IYGVILTALF LRVKFSRSAD APAYQQGQNQ LYNELNLGRR 90        100        110        120
EEYDVLDKRR GRDPEMGGKP QRRKNPQEGL YNELQKDKMA
```

TABLE 4-continued

Uniprot P20963 human CD3ζ
isoform 3 (SEQ ID NO: 5)

```
        130        140        150        160
EAYSEIGMKG ERRRGKGHDG LYQGLSTATK DTYDALHMQA

LPPR 1-21 signal peptide
22-30 extracellular
31-51 transmembrane
52-164 intracellular domain
61-89 ITAM1
100-128 ITAM2
131-159 ITAM3
```

TABLE 5

Exemplary Hinge region Sequences

Human IgG1 EPKSCDKTHTCPPCP (SEQ ID NO: 6)

Human IgG2 ERKCCVECPPCP (SEQ ID NO:7)

Human IgG3 ELKTPLGDTHTCPRCP (EPKSCDTPPPCPRCP)₃ (SEQ ID NO:8)

Human IgG4 ESKYGPPCPSCP (SEQ ID NO:9)

Modified Human IgG4 ESKYGPPCPPCP (SEQ ID NO:10)

Modified Human IgG4 YGPPCPPCP (SEQ ID NO: 11)

Modified Human IgG4 KYGPPCPPCP (SEQ ID NO: 12)

Modified Human IgG4 EVVKYGPPCPPCP (SEQ ID NO: 13)

TABLE 6

Her2t nucleic acid (SEQ ID NO: 14) and
amino acid sequence (SEQ ID NO: 15)

```
Her2t (CHP) Nucleotide and Amino Acid Sequence
 M   L   L   L   V   T   S   L   L   L   C   E   L   P   H
ATGCT TCTCCTGGTG ACAAGCCTTC TGCTCTGTGA GTTACCACAC
TACGA AGAGGACCAC TGTTCGGAAG ACGAGACACT CAATGGTGTG P   A   F   L   L   I   P   C   H   P   E   C   Q   P
CCAGCATTCC TCCTGATCCC ATGCCACCCT GAGTGTCAGC
GGTCGTAAGG AGGACTAGGG TACGGTGGGA CTCACAGTCG Q   N   G   S   V   T   C   F   G   P   E   A   D   Q   C   V   A   C   A   H
CCCAGAATGG CTCAGTGACC TGTTTTGGAC CGGAGGCTGA CCAGTGTGTG GCCTGTGCCC
GGGTCTTACC GAGTCACTGG ACAAAACCTG GCCTCCGACT GGTCACACAC CGGACACGGG

•  Y   K   D   P   P   F   C   V   A   R   C   P   S
ACTATAAGGA CCCTCCCTTC TGCGTGGCCC GCTGCCCCAG
TGATATTCCT GGGAGGGAAG ACGCACCGGG CGACGGGGTC

G   V   K   P   D   L   S   Y   M   P   I   W   K   F   P   D   E   E   G   A
CGGTGTGAAA CCTGACCTCT CCTACATGCC CATCTGGAAG TTTCCAGATG AGGAGGGCGC
GCCACACTTT GGACTGGAGA GGATGTACGG GTAGACCTTC AAAGGTCTAC TCCTCCCGCG

•  C   Q   P   C   P   I   N   C   T   H   S   C   V
ATGCCAGCCT TGCCCCATCA ACTGCACCCA CTCCTGTGTG
TACGGTCGGA ACGGGGTAGT TGACGTGGGT GAGGACACAC

D   L   D   D   K   G   C   P   A   E   Q   R   A   S   P   L   T   S   I   I
GACCTGGATG ACAAGGGCTG CCCCGCCGAG CAGAGAGCCA GCCCTCTGAC GTCCATCATC
CTGGACCTAC TGTTCCCGAC GGGGCGGCTC GTCTCTCGGT CGGGAGACTG CAGGTAGTAG

S   A   V   V   G   I   L   L   V   V   V   L   G   V   V   F   G   I   L   I   •
TCTGCGGTGG TTGGCATTCT GCTGGTCGTG GTCTTGGGGG TGGTGTTTGG GATCCTCATC TGA
AGACGGGACC AACCGTAAGA CGACCAGCAC CAGAACCCCC ACCAGAAACC CTAGGAGTAG ACT
```

(SEQ ID NO: 17)
1-MLLLVTSLLLCELPHPAFLLIP-22 (GMCSFRss)

(SEQ ID NO: 18)
563-C H P E C Q P Q N G S V T C F G P E A D Q C V A C A H Y K D
P P F C V A R C P S G V K P D L S Y M P I W K F P D E E G A C Q
P C P I N C T H S C V D L D D K G C P A E Q R A S P L T 652
(Her2 sequence-residues in bold identified as
binding to Herceptin)

(SEQ ID NO:19)
653-SIISAVVGILLVWLGVVFGILII-675

(SEQ ID NO: 20)
563-C H P E C Q P Q N G S V T C F G P E A D Q C V A C A H Y K D P
P F C V A R C P S G V K P D L S Y M P I W K F P D E E G A C Q P C
P I N C T H S C V D L D D K G C P A E Q R A S P L T S I I S A V V
G I L L V V V L G V V F G I L I-675

TABLE 7

EGFRt Nucleotide (SEQ ID NO: 21)
and Amino Acid (SEQ ID NO: 22)

```
DNA: ATGCTTCTCCTGGTGACAAGCCTT
AA:  M  L  L  L  V  T  S  L

DNA: CTGCTCTGTGAGTTACCACACCCAGCATTCCTCCTGATCCCACGCAAAGTG
AA:  L  L  C  E  L  P  H  P  A  F  L  L  I  P  R  K  V

DNA: TGTAACGGAATAGGTATTGGTGAATTTAAAGACTCACTCTCCATAAATGCT
AA:  C  N  G  I  G  I  G  E  F  K  D  S  L  S  I  N  A

DNA: ACGAATATTAAACACTTCAAAAACTGCACCTCCATCAGTGGCGATCTCCAC
AA:  T  N  I  K  H  F  K  N  C  T  S  I  S  G  D  L  H

DNA: ATCCTGCCGGTGGCATTTAGGGGTGACTCCTTCACACATACTCCTCCTCTG
AA:  I  L  P  V  A  F  R  G  D  S  F  T  H  T  P  P  L

DNA: GATCCACAGGAACTGGATATTCTGAAAACCGTAAAGGAAATCACAGGGTTT
AA:  D  P  Q  E  L  D  I  L  K  T  V  K  E  I  T  G  F

DNA: TTGCTGATTCAGGCTTGGCCTGAAAACAGGACGGACCTCCATGCCTTTGAG
AA:  L  L  I  Q  A  W  P  E  N  R  T  D  L  H  A  F  E

DNA: AACCTAGAAATCATACGCGGCAGGACCAAGCAACATGGTCAGTTTTCTCTT
AA:  N  L  E  I  I  R  G  R  T  K  Q  H  G  Q  F  S  L

DNA: GCAGTCGTCAGCCTGAACATAACATCCTTGGGATTACGCTCCCTCAAGGAG
AA:  A  V  V  S  L  N  I  T  S  L  G  L  R  S  L  K  E

DNA: ATAAGTGATGGAGATGTGATAATTTCAGGAAACAAAAATTTGTGCTATGCA
AA:  I  S  D  G  D  V  I  I  S  G  N  K  N  L  C  Y  A

DNA: AATACAATAAACTGGAAAAAACTGTTTGGGACCTCCGGTCAGAAAACCAAA
AA:  N  T  I  N  W  K  K  L  F  G  T  S  G  Q  K  T  K

DNA: ATTATAAGCAACAGAGGTGAAAACAGCTGCAAGGCCACAGGCCAGGTCTGC
AA:  I  I  S  N  R  G  E  N  S  C  K  A  T  G  Q  V  C

DNA: CATGCCTTGTGCTCCCCCGAGGGCTGCTGGGGCCCGGAGCCCAGGGACTGC
AA:  H  A  L  C  S  P  E  G  C  W  G  P  E  P  R  D  C

DNA: GTCTCTTGCCGGAATGTCAGCCGAGGCAGGGAATGCGTGGACAAGTGCAAC
AA:  V  S  C  R  N  V  S  R  G  R  E  C  V  D  K  C  N

DNA: CTTCTGGAGGGTGAGCCAAGGGAGTTTGTGGAGAACTCTGAGTGCATACAG
AA:  L  L  E  G  E  P  R  E  F  V  E  N  S  E  C  I  Q

DNA: TGCCACCCAGAGTGCCTGCCTCAGGCCATGAACATCACCTGCACAGGACGG
AA:  C  H  P  E  C  L  P  Q  A  M  N  I  T  C  T  G  R

DNA: GGACCAGACAACTGTATCCAGTGTGCCCACTACATTGACGGCCCCCACTGC
AA:  G  P  D  N  C  I  Q  C  A  H  Y  I  D  G  P  H  C

DNA: GTCAAGACCTGCCCGGCAGGAGTCATGGGAGAAAACAACACCCTGGTCTGG
AA:  V  K  T  C  P  A  G  V  M  G  E  N  N  T  L  V  W

DNA: AAGTACGCAGACGCCGGCCATGTGTGCCACCTGTGCCATCCAAACTGCACC
AA:  K  Y  A  D  A  G  H  V  C  H  L  C  H  P  N  C  T

DNA: TACGGATGCACTGGGCCAGGTCTTGAAGGCTGTCCAACGAATGGGCCTAAG
AA:  Y  G  C  T  G  P  G  L  E  G  C  P  T  N  G  P  K

DNA: ATCCCGTCCATCGCCACTGGGATGGTGGGGGCCCTCCTCTTGCTGCTGGTG
AA:  I  P  S  I  A  T  G  M  V  G  A  L  L  L  L  L  V

DNA: GTGGCCCTGGGGATCGGCCTCTTCATG*TGA* (SEQ ID NO: 21)
AA:  V  A  L  G  I  G  L  F  M  * (SEQ ID NO: 22)
```

TABLE 8

Full length Her2 isoform 1 (Uniprot P04626-1) (SEQ ID NO: 23)

MELAALCRWG LLLALLPPGA ASTQVCTGTD MKLRLPASPE THLDMLRHLY    50

QGCQVVQGNL ELTYLPTNAS LSFLQDIQEV QGYVLIAHNQ VRQVPLQRLR   100

TABLE 8-continued

Full length Her2 isoform 1 (Uniprot P04626-1) (SEQ ID NO: 23)

```
IVRGTQLFED NYALAVLDNG DPLNNTTPVT GASPGGLREL QLRSLTEILK  150
GGVLIQRNPQ LCYQDTILWK DIFHKNNQLA LTLIDTNRSR ACHPCSPMCK  200
GSRCWGESSE DCQSLTRTVC AGGCARCKGP LPTDCCHEQC AAGCTGPKHS  250
DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL  350
REVRAVTSAN IQEFAGCKKI FGSLAFLPES FDGDPASNTA PLQPEQLQVF  400
ETLEEITGYL YISAWPDSLP DLSVFQNLQV IRGRILHNGA YSLTLQGLGI  450
SWLGLRSLRE LGSGLALIHH NTHLCFVHTV PWDQLFRNPH QALLHTANRP  500
EDECVGEGLA CHQLCARGHC WGPGPTQCVN CSQFLRGQEC VEECRVLQGL  550
PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP  650
LTSIISAVVG ILLVVVLGVV FGILIKRRQQ KIRKYTMRRL LQETELVEPL  700
TPSGAMPNQA QMRILKETEL RKVKVLGSGA FGTVYKGIWI PDGENVKIPV  750
AIKVLRENTS PKANKEILDE AYVMAGVGSP YVSRLLGICL TSTVQLVTQL  800
MPYGCLLDHV RENRGRLGSQ DLLNWCMQIA KGMSYLEDVR LVHRDLAARN  850
VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID  950
VYMIMVKCWM IDSECRPRFR ELVSEFSRMA RDPQRFVVIQ NEDLGPASPL 1000
DSTFYRSLLE DDDMGDLVDA EEYLVPQQGF FCPDPAPGAG GMVHHRHRSS 1050
STRSGGGDLT LGLEPSEEEA PRSPLAPSEG AGSDVFDGDL GMGAAKGLQS 1100
LPTHDPSPLQ RYSEDPTVPL PSETDGYVAP LTCSPQPEYV NQPDVRPQPP 1150
SPREGPLPAA RPAGATLERP KTLSPGKNGV VKDVFAFGGA VENPEYLTPQ 1200
GGAAPQPHPP PAFSPAFDNL YYWDQDPPER GAPPSTFKGT PTAENPEYLG 1250
LDVPV                                                 1255
```

1-22-signal peptide
23-652-extracellular domain
653-675 transmembrane domain
676-1255 cytoplasmic

TABLE 9

CD20CAR Nucleic acid (SEQ ID NO:24)
and polypeptide (SEQ ID No:25)

CD20 scFV NA
Atggagacagacacactcctgctatgggtgctgctgctctggttccag gttccacaggtgacattgtgctgacccaatctccagctatcctgtctgc atctccaggggagaaggtcacaatgacttgcagggccagctcaagtgta aattacatggactggtaccagaagaagccaggatcctcccccaaaccct ggatttatgccacatccaacctggcttctggagtccctgctcgcttcag tggcagtgggtctgggacctcttactctctcacaatcagcagagtggag gctgaagatgctgccacttattactgccagcagtggagttttaatccac ccacgttcggaggggggaccaagctggaaataaaaggcagtactagcgg gtggtggctccggggcggttccggtggggcggcacagcgaggtgcag ctgcagcagtctggggctgagctggtgaagcctggggcctcagtgaaga tgtcctgcaaggcttctggctacacatttaccagttacaatatgcactg ggtaaagcagacacctggacagggcctggaatggattggagctatttat ccaggaaatggtgatacttccttacaatcagaagttcaaggcaaggcc acattgactgcagacaaatcctccagcacagcctacagcagctcagcag cctgacatctgaggactctgcggactattactgtgcaagatctaattat tacggtagtagctactggttcttcgatgtctggggcgcagggaccacgg tcaccgtctcctca TABLE 9-continued CD20CAR Nucleic acid (SEQ ID NO:24) and polypeptide (SEQ ID No:25)

IgG4-Hinge
(SEQ ID NO: 47)
Gagagcaagtacggaccgccctgccccccttgccct

CH3
(SEQ ID NO: 48)
Ggccagcctcgcgagccccaggtgtacaccctgcctcctcccaggaag agatgaccaagaaccaggtgtccctgacctgcctggtgaagggcttcta ccccagcgacatcgccgtggagtgggagagcaacggccagcctgagaac aactacaagaccaccccctcccgtgctggacagcgacggcagcttcttcc tgtacagccggctgaccgtggacaagagccggtggcaggaaggcaacgt ctttagctgcagcgtgatgcacgaggccctgcacaaccactacacccag aagagcctgagcctgtccctgggcaag CD20 scFV Protein
(SEQ ID NO: 25)
M E T D T L L L W V L L L W V P G S T G D I V L T

Q S P A I L S A S P G E K V T M T C R *R A S S*

*V N Y M D* W Y Q K K P G S S P K P W I Y G V P A

*A T S N L A S* R F S G S G S G T S Y S L

T I S R V E A E D A A T Y Y C *Q Q W S F N P P T*

F G G G T K L E I K G S T S G G G S G G G S G G G

G S S E V Q L Q Q S G A E L V K P G A S V K M S C

K A S G Y T F T *S Y N M H* W V K O T P G Q G L E W

I G *A I Y P G N G D T S Y N Q K F K G* K A T L T

A D K S S S T A Y M Q L S S L T S E D S A D Y Y C

A R *S N Y Y G S S Y W F F D V* W G A G T T V T V S

S

IgG4-Hinge
(SEQ ID NO: 49)
E S K Y G P P C P P C P

CH3
(SEQ ID NO: 50)
G Q P R E P Q V Y T L P P S Q E E M T K N Q V S L

T C L V K G F Y P S D I A V E W E S N G Q P E N N

Y K T T P P V L D S D G S F F L Y S R L T V D K S

R W Q E G N V F S C S V M H E A L H N H Y T Q K S

L S L S L G K

The rest of the CD20CAR construct (CD28tm-41BB-zeta-T2A-EGFRt) is the same as the CD19CAR-T2A-EGFRt construct.

---

What is claimed is:

1. A nucleic acid comprising a first polynucleotide encoding a fusion protein, wherein the fusion protein comprises:
   an extracellular domain comprising an amino acid sequence having at least 95% sequence identity to SEQ ID NO:18;
   a spacer, wherein the spacer is selected from the group consisting of a CD28 hinge domain, an IgG4 hinge domain, and a polypeptide comprising the amino acid sequence of SEQ ID NO:45; and
   a transmembrane domain, wherein the transmembrane domain is linked to the extracellular domain via the spacer.

2. The nucleic acid of claim 1, wherein the spacer comprises the amino acid sequence of SEQ ID NO:45.

3. The nucleic acid of claim 1, wherein the spacer comprises the IgG4 hinge domain.

4. The nucleic acid of claim 3, wherein the IgG4 hinge domain comprises the amino acid sequence of any one of SEQ ID NOs: 09-13.

5. The nucleic acid of claim 1, wherein the spacer comprises the CD28 hinge domain.

6. The nucleic acid of claim 1, wherein the extracellular domain comprises the amino acid sequence of SEQ ID NO: 18.

7. The nucleic acid of claim 1, wherein the transmembrane domain comprises the amino acid sequence of SEQ ID NO: 19.

8. The nucleic acid of claim 1, wherein the fusion protein comprises a leader polypeptide.

9. The nucleic acid of claim 8, wherein the leader polypeptide comprises the amino acid sequence of SEQ ID NO: 17.

10. The nucleic acid of claim 1, wherein the first polynucleotide is operably linked to a promoter.

11. The nucleic acid of claim 1, further comprising a second polynucleotide encoding a protein.

12. The nucleic acid of claim 11, wherein the first polynucleotide and second polynucleotide are linked via a T2A ribosome skip sequence.

13. The nucleic acid of claim 11, wherein the protein comprises a chimeric antigen receptor (CAR).

14. The nucleic acid of claim 13, wherein the CAR specifically binds to CD19.

15. A vector comprising the nucleic acid of claim 1.

16. The vector of claim 15, wherein the vector is a viral vector.

17. The vector of claim 16, wherein the vector is a lentiviral vector.

18. A isolated cell comprising the nucleic acid of claim 1.

19. The isolated cell of claim 18, wherein the cell is selected from the group consisting of a CD4+ cell, a CD8+ cell, a precursor T cell, and a hematopoietic stem cell.

20. The isolated cell of claim 18, wherein the cell is human.

\* \* \* \* \*

SEQUENCE LISTING

<160> NUMBER OF SEQ ID NOS: 50

<210> SEQ ID NO 1
<211> LENGTH: 27
<212> TYPE: DNA
<213> ORGANISM: Artificial Sequence
<220> FEATURE:
<223> OTHER INFORMATION: CD19CAR DNA encoding a portion of modified IgG4
      hinge region

<400> SEQUENCE: 1
gacgtggagg agaatcccgg ccctagg                                       27

<210> SEQ ID NO 2
<211> LENGTH: 476
<212> TYPE: PRT
<213> ORGANISM: Artificial Sequence
<220> FEATURE:
<223> OTHER INFORMATION: CD19 CAR

<400> SEQUENCE: 2

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val

```
                65                  70                  75                  80
        Pro Ser Arg Phe Ser Gly Ser Gly Ser Gly Thr Asp Tyr Ser Leu Thr
                            85                  90                  95

Ile Ser Asn Leu Glu Gln Glu Asp Ile Ala Thr Tyr Phe Cys Gln Gln
                        100                 105                 110

Gly Asn Thr Leu Pro Tyr Thr Phe Gly Gly Gly Thr Lys Leu Glu Ile
                    115                 120                 125

Thr Gly Ser Thr Ser Gly Ser Gly Lys Pro Gly Ser Gly Glu Gly Ser
                130                 135                 140

Thr Lys Gly Glu Val Lys Leu Gln Glu Ser Gly Pro Gly Leu Val Ala
        145                 150                 155                 160

Pro Ser Gln Ser Leu Ser Val Thr Cys Thr Val Ser Gly Val Ser Leu
                            165                 170                 175

Pro Asp Tyr Gly Val Ser Trp Ile Arg Gln Pro Pro Arg Lys Gly Leu
                        180                 185                 190

Glu Trp Leu Gly Val Ile Trp Gly Ser Glu Thr Thr Tyr Tyr Asn Ser
                    195                 200                 205

Ala Leu Lys Ser Arg Leu Thr Ile Ile Lys Asp Asn Ser Lys Ser Gln
                210                 215                 220

Val Phe Leu Lys Met Asn Ser Leu Gln Thr Asp Asp Thr Ala Ile Tyr
        225                 230                 235                 240

Tyr Cys Ala Lys His Tyr Tyr Gly Gly Ser Tyr Ala Met Asp Tyr
                            245                 250                 255

Trp Gly Gln Gly Thr Ser Val Thr Val Ser Ser Glu Ser Lys Tyr Gly
                        260                 265                 270

Pro Pro Cys Pro Pro Cys Pro Met Phe Trp Val Leu Val Val Val Gly
                    275                 280                 285

Gly Val Leu Ala Cys Tyr Ser Leu Leu Val Thr Val Ala Phe Ile Ile
                290                 295                 300

Phe Trp Val Lys Arg Gly Arg Lys Lys Leu Leu Tyr Ile Phe Lys Gln
        305                 310                 315                 320

Pro Phe Met Arg Pro Val Gln Thr Thr Gln Glu Glu Asp Gly Cys Ser
                            325                 330                 335

Cys Arg Phe Pro Glu Glu Glu Glu Gly Gly Cys Glu Leu Arg Val Lys
                        340                 345                 350

Phe Ser Arg Ser Ala Asp Ala Pro Ala Tyr Gln Gln Gly Gln Asn Gln
                    355                 360                 365

Leu Tyr Asn Glu Leu Asn Leu Gly Arg Arg Glu Glu Tyr Asp Val Leu
                370                 375                 380

Asp Lys Arg Arg Gly Arg Asp Pro Glu Met Gly Gly Lys Pro Arg Arg
        385                 390                 395                 400

Lys Asn Pro Gln Glu Gly Leu Tyr Asn Glu Leu Gln Lys Asp Lys Met
                            405                 410                 415

Ala Glu Ala Tyr Ser Glu Ile Gly Met Lys Gly Glu Arg Arg Arg Gly
                        420                 425                 430

Lys Gly His Asp Gly Leu Tyr Gln Gly Leu Ser Thr Ala Thr Lys Asp
                    435                 440                 445

Thr Tyr Asp Ala Leu His Met Gln Ala Leu Pro Pro Arg Leu Glu Gly
                450                 455                 460

Gly Gly Glu Gly Arg Gly Ser Leu Leu Thr Cys Gly
        465                 470                 475

<210> SEQ ID NO 3
```

```
<211> LENGTH: 180
<212> TYPE: PRT
<213> ORGANISM: Artificial Sequence
<220> FEATURE:
<223> OTHER INFORMATION: CD28 domain

<400> SEQUENCE: 3
```

| | | | | | | | | | | | | | | |
|---|---|---|---|---|---|---|---|---|---|---|---|---|---|---|
| Met | Leu | Arg | Leu | Leu | Ala | Leu | Asn | Leu | Phe | Pro | Ser | Ile | Gln | Val |
| 1 | | | | 5 | | | | | 10 | | | | | 15 |
| Thr | Gly | Asn | Lys | Ile | Leu | Val | Lys | Gln | Ser | Pro | Met | Leu | Val | Ala | Tyr |
| | | | 20 | | | | | 25 | | | | | 30 | | |
| Asp | Asn | Ala | Val | Asn | Leu | Ser | Cys | Lys | Tyr | Ser | Tyr | Asn | Leu | Phe | Ser |
| | | 35 | | | | | 40 | | | | | 45 | | | |
| Arg | Glu | Phe | Arg | Ala | Ser | Leu | His | Lys | Gly | Leu | Asp | Ser | Ala | Val | Glu |
| 50 | | | | | 55 | | | | | 60 | | | | | |
| Val | Cys | Val | Val | Tyr | Gly | Asn | Tyr | Ser | Gln | Gln | Leu | Gln | Val | Tyr | Ser |
| 65 | | | | | 70 | | | | | 75 | | | | | 80 |
| Lys | Thr | Gly | Phe | Asn | Cys | Asp | Gly | Lys | Leu | Gly | Asn | Glu | Ser | Val | Thr |
| | | | | 85 | | | | | 90 | | | | | 95 | |
| Phe | Tyr | Leu | Gln | Asn | Leu | Tyr | Val | Asn | Gln | Thr | Asp | Ile | Tyr | Phe | Cys |
| | | | 100 | | | | | 105 | | | | | 110 | | |
| Lys | Ile | Glu | Val | Met | Tyr | Pro | Pro | Pro | Tyr | Leu | Asp | Asn | Glu | Lys | Ser |
| | | | 115 | | | | | 120 | | | | | 125 | | |
| Asn | Gly | Thr | Ile | Ile | His | Val | Lys | Gly | Lys | His | Leu | Cys | Pro | Ser | Pro |
| | | 130 | | | | | 135 | | | | | 140 | | | |
| Leu | Phe | Pro | Gly | Pro | Ser | Lys | Pro | Phe | Trp | Val | Leu | Val | Val | Val | Gly |
| 145 | | | | | 150 | | | | | 155 | | | | | 160 |
| Gly | Val | Leu | Ala | Cys | Tyr | Ser | Leu | Leu | Val | Thr | Val | Ala | Phe | Ile | Ile |
| | | | | 165 | | | | | 170 | | | | | 175 | |
| Phe | Trp | Val | Arg | | | | | | | | | | | | |
| | | | 180 | | | | | | | | | | | | |

```
<210> SEQ ID NO 4
<211> LENGTH: 240
<212> TYPE: PRT
<213> ORGANISM: Artificial Sequence
<220> FEATURE:
<223> OTHER INFORMATION: 4-1BB domain

<400> SEQUENCE: 4
```

| | | | | | | | | | | | | | | | |
|---|---|---|---|---|---|---|---|---|---|---|---|---|---|---|---|
| Met | Gly | Asn | Ser | Cys | Tyr | Asn | Ile | Val | Ala | Thr | Leu | Leu | Leu | Val | Leu |
| 1 | | | | 5 | | | | | 10 | | | | | 15 | |
| Asn | Phe | Glu | Arg | Thr | Arg | Ser | Leu | Gln | Asp | Pro | Cys | Ser | Asn | Cys | Pro |
| | | | 20 | | | | | 25 | | | | | 30 | | |
| Ala | Gly | Thr | Phe | Cys | Asp | Asn | Asn | Arg | Asn | Gln | Ile | Cys | Ser | Pro | Cys |
| | | 35 | | | | | 40 | | | | | 45 | | | |
| Pro | Pro | Asn | Ser | Phe | Ser | Ser | Ala | Gly | Gly | Gln | Arg | Thr | Cys | Asp | Ile |
| 50 | | | | | 55 | | | | | 60 | | | | | |
| Cys | Arg | Gln | Cys | Lys | Gly | Val | Phe | Arg | Thr | Arg | Lys | Glu | Cys | Ser | Ser |
| 65 | | | | | 70 | | | | | 75 | | | | | 80 |
| Thr | Ser | Asn | Ala | Glu | Cys | Asp | Cys | Thr | Pro | Gly | Phe | His | Cys | Leu | Gly |
| | | | | 85 | | | | | 90 | | | | | 95 | |
| Ala | Gly | Cys | Ser | Met | Cys | Glu | Gln | Asp | Cys | Lys | Gln | Gly | Gln | Glu | Leu |
| | | | 100 | | | | | 105 | | | | | 110 | | |
| Thr | Lys | Lys | Gly | Cys | Lys | Asp | Cys | Cys | Phe | Gly | Thr | Phe | Asn | Asp | Gln |
| | | 115 | | | | | 120 | | | | | 125 | | | |
| Lys | Arg | Gly | Ile | Cys | Arg | Pro | Trp | Thr | Asn | Cys | Ser | Leu | Asp | Gly | Lys |

```
Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
            165                 170                 175

Pro Ala Arg Glu Pro Gly His Ser Pro Gln Ile Ile Ser Phe Phe Leu
        180                 185                 190

Ala Leu Thr Ser Thr Ala Leu Leu Phe Leu Leu Phe Phe Leu Thr Leu
    195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240
```

<210> SEQ ID NO 5
<211> LENGTH: 164
<212> TYPE: PRT
<213> ORGANISM: Artificial Sequence
<220> FEATURE:
<223> OTHER INFORMATION: Human CD3 Zeta isoform 3

<400> SEQUENCE: 5

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 6
<211> LENGTH: 15
<212> TYPE: PRT
<213> ORGANISM: Artificial Sequence
<220> FEATURE:
<223> OTHER INFORMATION: Human IgG1 hinge region

<400> SEQUENCE: 6

```
Glu Pro Lys Ser Cys Asp Lys Thr His Thr Cys Pro Pro Cys Pro
1               5                   10                  15
```

<210> SEQ ID NO 7
<211> LENGTH: 12
<212> TYPE: PRT

```
<213> ORGANISM: Artificial Sequence
<220> FEATURE:
<223> OTHER INFORMATION: Human IgG2 hinge region

<400> SEQUENCE: 7

Glu Arg Lys Cys Cys Val Glu Cys Pro Pro Cys Pro
1               5                   10

<210> SEQ ID NO 8
<211> LENGTH: 61
<212> TYPE: PRT
<213> ORGANISM: Artificial Sequence
<220> FEATURE:
<223> OTHER INFORMATION: Human IgG3 hinge region

<400> SEQUENCE: 8

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 9
<211> LENGTH: 12
<212> TYPE: PRT
<213> ORGANISM: Artificial Sequence
<220> FEATURE:
<223> OTHER INFORMATION: Human IgG4 hinge region

<400> SEQUENCE: 9

Glu Ser Lys Tyr Gly Pro Pro Cys Pro Ser Cys Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Modified Human IgG4 hinge region

<400> SEQUENCE: 10

Glu Ser Lys Tyr Gly Pro Pro Cys Pro Pro Cys Pro
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Modified Human IgG4 hinge region

<400> SEQUENCE: 11

Tyr Gly Pro Pro Cys Pro Pro Cys Pro
1               5

<210> SEQ ID NO 12
<211> LENGTH: 10
<212> TYPE: PRT
<213> ORGANISM: Artificial Sequence
<220> FEATURE:
<223> OTHER INFORMATION: Modified Human IgG4 hinge region

<400> SEQUENCE: 12
```

```
Lys Tyr Gly Pro Pro Cys Pro Pro Cys Pro
1               5                  10
```

<210> SEQ ID NO 13
<211> LENGTH: 13
<212> TYPE: PRT
<213> ORGANISM: Artificial Sequence
<220> FEATURE:
<223> OTHER INFORMATION: Modified Human IgG4 hinge region

<400> SEQUENCE: 13

```
Glu Val Val Lys Tyr Gly Pro Pro Cys Pro Pro Cys Pro
1               5                  10
```

<210> SEQ ID NO 14
<211> LENGTH: 408
<212> TYPE: DNA
<213> ORGANISM: Artificial Sequence
<220> FEATURE:
<223> OTHER INFORMATION: Her2t (truncated Her2 protein)

<400> SEQUENCE: 14

```
atgcttctcc tggtgacaag ccttctgctc tgtgagttac cacacccagc attcctcctg      60
atcccatgcc accctgagtg tcagccccag aatggctcag tgacctgttt tggaccggag     120
gctgaccagt gtgtggcctg tgcccactat aaggaccctc ccttctgcgt ggcccgctgc     180
cccagcggtg tgaaacctga cctctcctac atgcccatct ggaagtttcc agatgaggag     240
ggcgcatgcc agccttgccc catcaactgc acccactcct gtgtggacct ggatgacaag     300
ggctgccccg ccgagcagag agccagccct ctgacgtcca tcatctctgc ggtggttggc     360
attctgctgg tcgtggtctt gggggtggtc tttgggatcc tcatctga                  408
```

<210> SEQ ID NO 15
<211> LENGTH: 135
<212> TYPE: PRT
<213> ORGANISM: Artificial Sequence
<220> FEATURE:
<223> OTHER INFORMATION: Her2t (truncated Her2 protein)

<400> SEQUENCE: 15

```
Met Leu Leu Leu Val Thr Ser Leu Leu Cys Glu Leu Pro His Pro
1               5                  10                  15

Ala Phe Leu Leu Ile Pro Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala Arg Cys Pro Ser Gly Val
    50                  55                  60

Lys Pro Asp Leu Ser Tyr Met Pro Ile Trp Lys Phe Pro Asp Glu Glu
65                  70                  75                  80

Gly Ala Cys Gln Pro Cys Pro Ile Asn Cys Thr His Ser Cys Val Asp
                85                  90                  95

Leu Asp Asp Lys Gly Cys Pro Ala Glu Gln Arg Ala Ser Pro Leu Thr
            100                 105                 110

Ser Ile Ile Ser Ala Val Val Gly Ile Leu Leu Val Val Leu Gly
        115                 120                 125

Val Val Phe Gly Ile Leu Ile
            130                 135
```

```
<210> SEQ ID NO 16
<211> LENGTH: 35
<212> TYPE: PRT
<213> ORGANISM: Artificial Sequence
<220> FEATURE:
<223> OTHER INFORMATION: Synthetic genetic tag

<400> SEQUENCE: 16

Met Leu Leu Leu Val Thr Ser Leu Leu Leu Cys Glu Leu Pro His Pro
1               5                   10                  15

Ala Phe Leu Leu Ile Pro Cys His Pro Glu Cys Gln Pro Gln Asn Gly
            20                  25                  30

Ser Val Thr
        35

<210> SEQ ID NO 17
<211> LENGTH: 22
<212> TYPE: PRT
<213> ORGANISM: Artificial Sequence
<220> FEATURE:
<223> OTHER INFORMATION: Leader sequence for protein localization

<400> SEQUENCE: 17

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 18
<211> LENGTH: 90
<212> TYPE: PRT
<213> ORGANISM: Artificial Sequence
<220> FEATURE:
<223> OTHER INFORMATION: Fragment of Her2 protein recognized by an
      antiHer2 antibody

<400> SEQUENCE: 18

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
            20                  25                  30

Phe Cys Val Ala Arg Cys Pro Ser Gly Val Lys Pro Asp Leu Ser Tyr
        35                  40                  45

Met Pro Ile Trp Lys Phe Pro Asp Glu Gly Ala Cys Gln Pro Cys
    50                  55                  60

Pro Ile Asn Cys Thr His Ser Cys Val Asp Leu Asp Asp Lys Gly Cys
65                  70                  75                  80

Pro Ala Glu Gln Arg Ala Ser Pro Leu Thr
                85                  90

<210> SEQ ID NO 19
<211> LENGTH: 24
<212> TYPE: PRT
<213> ORGANISM: Artificial Sequence
<220> FEATURE:
<223> OTHER INFORMATION: Fragment of Her2 transmembrane domain, the
      transmembrane domain of Her2

<400> SEQUENCE: 19

Ser Ile Ile Ser Ala Val Val Gly Ile Leu Leu Val Val Val Leu Gly
1               5                   10                  15

Val Val Phe Gly Ile Leu Ile Ile
            20
```

<210> SEQ ID NO 20
<211> LENGTH: 113
<212> TYPE: PRT
<213> ORGANISM: Artificial Sequence
<220> FEATURE:
<223> OTHER INFORMATION: Her2 transmembrane domain as amino acids
      653-675

<400> SEQUENCE: 20

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
            20                  25                  30

Phe Cys Val Ala Arg Cys Pro Ser Gly Val Lys Pro Asp Leu Ser Tyr
        35                  40                  45

Met Pro Ile Trp Lys Phe Pro Asp Glu Glu Gly Ala Cys Gln Pro Cys
    50                  55                  60

Pro Ile Asn Cys Thr His Ser Cys Val Asp Leu Asp Asp Lys Gly Cys
65                  70                  75                  80

Pro Ala Glu Gln Arg Ala Ser Pro Leu Thr Ser Ile Ile Ser Ala Val
                85                  90                  95

Val Gly Ile Leu Leu Val Val Val Leu Gly Val Val Phe Gly Ile Leu
            100                 105                 110

Ile

<210> SEQ ID NO 21
<211> LENGTH: 1074
<212> TYPE: DNA
<213> ORGANISM: Artificial Sequence
<220> FEATURE:
<223> OTHER INFORMATION: Encoding a truncated epidermal growth factor
      receptor

<400> SEQUENCE: 21
atgcttctcc tggtgacaag ccttctgctc tgtgagttac cacacccagc attcctcctg      60
atcccacgca aagtgtgtaa cggaataggt attggtgaat ttaaagactc actctccata     120
aatgctacga atattaaaca cttcaaaaac tgcacctcca tcagtggcga tctccacatc     180
ctgccggtgg catttagggg tgactccttc acacatactc ctcctctgga tccacaggaa     240
ctggatattc tgaaaaccgt aaaggaaatc acagggtttt tgctgattca ggcttggcct     300
gaaaacagga cggacctcca tgcctttgag aacctagaaa tcatacgcgg caggaccaag     360
caacatggtc agttttctct tgcagtcgtc agcctgaaca taacatcctt gggattacgc     420
tccctcaagg ataagtga tggagatgtg ataatttcag gaaacaaaaa tttgtgctat     480
gcaaatacaa taaactggaa aaaactgttt gggacctccg gtcagaaaac caaaattata     540
agcaacagag gtgaaaacag ctgcaaggcc acaggccagg tctgccatgc cttgtgctcc     600
cccgagggct gctggggccc ggagcccagg gactgcgtct cttgccggaa tgtcagccga     660
ggcagggaat gcgtggacaa gtgcaacctt ctggagggtg agccaaggga gtttgtggag     720
aactctgagt gcatacagtg ccacccagag tgcctgcctc aggccatgaa catcacctgc     780
acaggacggg gaccagacaa ctgtatccag tgtgcccact acattgacgg cccccactgc     840
gtcaagacct gcccggcagg agtcatggga gaaacaacaa ccctggtctg aagtacgca     900 gacgccggcc atgtgtgcca cctgtgccat ccaaactgca cctacggatg cactgggcca     960
ggtcttgaag gctgtccaac gaatgggcct aagatcccgt ccatcgccac tgggatggtg    1020
ggggccctcc tcttgctgct ggtggtggcc ctggggatcg gcctcttcat gtga       1074

<210> SEQ ID NO 22
<211> LENGTH: 357
<212> TYPE: PRT
<213> ORGANISM: Artificial Sequence
<220> FEATURE:
<223> OTHER INFORMATION: Truncated epidermal growth factor receptor

<400> SEQUENCE: 22

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Ala Leu Gly
            340                 345                 350
```

```
Ile Gly Leu Phe Met
        355
```

<210> SEQ ID NO 23
<211> LENGTH: 1255
<212> TYPE: PRT
<213> ORGANISM: Artificial Sequence
<220> FEATURE:
<223> OTHER INFORMATION: Full length Her2 isoform 1 human

<400> SEQUENCE: 23

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350
```

```
Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
```

```
                770             775             780
Leu Leu Gly Ile Cys Leu Thr Ser Thr Val Gln Leu Thr Gln Leu
785                 790             795                 800

Met Pro Tyr Gly Cys Leu Leu Asp His Val Arg Glu Asn Arg Gly Arg
                805             810              815

Leu Gly Ser Gln Asp Leu Leu Asn Trp Cys Met Gln Ile Ala Lys Gly
                820             825             830

Met Ser Tyr Leu Glu Asp Val Arg Leu Val His Arg Asp Leu Ala Ala
                835             840             845

Arg Asn Val Leu Val Lys Ser Pro Asn His Val Lys Ile Thr Asp Phe
850                 855             860

Gly Leu Ala Arg Leu Leu Asp Ile Asp Glu Thr Glu Tyr His Ala Asp
865                 870             875                 880

Gly Gly Lys Val Pro Ile Lys Trp Met Ala Leu Glu Ser Ile Leu Arg
                885             890             895

Arg Arg Phe Thr His Gln Ser Asp Val Trp Ser Tyr Gly Val Thr Val
                900             905             910

Trp Glu Leu Met Thr Phe Gly Ala Lys Pro Tyr Asp Gly Ile Pro Ala
                915             920             925

Arg Glu Ile Pro Asp Leu Leu Glu Lys Gly Glu Arg Leu Pro Gln Pro
                930             935             940

Pro Ile Cys Thr Ile Asp Val Tyr Met Ile Met Val Lys Cys Trp Met
945                 950             955                 960

Ile Asp Ser Glu Cys Arg Pro Arg Phe Arg Glu Leu Val Ser Glu Phe
                965             970             975

Ser Arg Met Ala Arg Asp Pro Gln Arg Phe Val Val Ile Gln Asn Glu
                980             985             990

Asp Leu Gly Pro Ala Ser Pro Leu Asp Ser Thr Phe Tyr Arg Ser Leu
                995             1000            1005

Leu Glu Asp Asp Asp Met Gly Asp Leu Val Asp Ala Glu Glu Tyr Leu
                1010            1015            1020

Val Pro Gln Gln Gly Phe Phe Cys Pro Asp Pro Ala Pro Gly Ala Gly
1025                1030            1035            1040

Gly Met Val His His Arg His Arg Ser Ser Ser Thr Arg Ser Gly Gly
                1045            1050            1055

Gly Asp Leu Thr Leu Gly Leu Glu Pro Ser Glu Glu Ala Pro Arg
                1060            1065            1070

Ser Pro Leu Ala Pro Ser Glu Gly Ala Gly Ser Asp Val Phe Asp Gly
                1075            1080            1085

Asp Leu Gly Met Gly Ala Ala Lys Gly Leu Gln Ser Leu Pro Thr His
                1090            1095            1100

Asp Pro Ser Pro Leu Gln Arg Tyr Ser Glu Asp Pro Thr Val Pro Leu
1105                1110            1115            1120

Pro Ser Glu Thr Asp Gly Tyr Val Ala Pro Leu Thr Cys Ser Pro Gln
                1125            1130            1135

Pro Glu Tyr Val Asn Gln Pro Asp Val Arg Pro Gln Pro Pro Ser Pro
                1140            1145            1150

Arg Glu Gly Pro Leu Pro Ala Ala Arg Pro Ala Gly Ala Thr Leu Glu
                1155            1160            1165

Arg Pro Lys Thr Leu Ser Pro Gly Lys Asn Gly Val Val Lys Asp Val
                1170            1175            1180

Phe Ala Phe Gly Gly Ala Val Glu Asn Pro Glu Tyr Leu Thr Pro Gln
1185                1190            1195            1200
```

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
        1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250            1255

<210> SEQ ID NO 24
<211> LENGTH: 798
<212> TYPE: DNA
<213> ORGANISM: Artificial Sequence
<220> FEATURE:
<223> OTHER INFORMATION: CD20CAR DNA chimeric antigen receptor

<400> SEQUENCE: 24
atggagacag acacactcct gctatgggtg ctgctgctct ggttccagg ttccacaggt        60 gacattgtgc tgacccaatc tccagctatc ctgtctgcat ctccagggga aaggtcaca       120 atgacttgca gggccagctc aagtgtaaat tacatggact ggtaccagaa gaagccagga      180
tcctccccca aaccctggat ttatgccaca tccaacctgg cttctggagt ccctgctcgc      240
ttcagtggca gtgggtctgg gacctcttac tctctcacaa tcagcagagt ggaggctgaa      300
gatgctgcca cttattactg ccagcagtgg agttttaatc acccacgtt cggagggggg       360 accaagctgg aaataaaagg cagtactagc ggtggtggct ccgggggcgg ttccggtggg      420
ggcggcagca gcgaggtgca gctgcagcag tctggggctg agctggtgaa gcctggggcc      480
tcagtgaaga tgtcctgcaa ggcttctggc tacacattta ccagttacaa tatgcactgg      540
gtaaagcaga cacctggaca gggcctggaa tggattggag ctatttatcc aggaaatggt      600
gatacttcct acaatcagaa gttcaaaggc aaggccacat tgactgcaga caaatcctcc      660
agcacagcct acatgcagct cagcagcctg acatctgagg actctgcgga ctattactgt      720
gcaagatcta attattacgg tagtagctac tggttcttcg atgtctgggg cgcagggacc      780
acggtcaccg tctcctca                                                    798

<210> SEQ ID NO 25
<211> LENGTH: 266
<212> TYPE: PRT
<213> ORGANISM: Artificial Sequence
<220> FEATURE:
<223> OTHER INFORMATION: CD20CAR sythetic construct

<400> SEQUENCE: 25

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Asn Tyr Met Asp Trp Tyr Gln Lys Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

```
Val Glu Ala Glu Asp Ala Ala Thr Tyr Tyr Cys Gln Gln Trp Ser Phe
            100                 105                 110

Asn Pro Pro Thr Phe Gly Gly Gly Thr Lys Leu Glu Ile Lys Gly Ser
            115                 120                 125

Thr Ser Gly Gly Gly Ser Gly Gly Gly Ser Gly Gly Gly Gly Ser Ser
            130                 135                 140

Glu Val Gln Leu Gln Gln Ser Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
            195                 200                 205

Lys Gly Lys Ala Thr Leu Thr Ala Asp Lys Ser Ser Ser Thr Ala Tyr
            210                 215                 220

Met Gln Leu Ser Ser Leu Thr Ser Glu Asp Ser Ala Asp Tyr Tyr Cys
225                 230                 235                 240

Ala Arg Ser Asn Tyr Tyr Gly Ser Ser Tyr Trp Phe Phe Asp Val Trp
                245                 250                 255

Gly Ala Gly Thr Thr Val Thr Val Ser Ser
            260                 265

<210> SEQ ID NO 26
<211> LENGTH: 15
<212> TYPE: PRT
<213> ORGANISM: Artificial Sequence
<220> FEATURE:
<223> OTHER INFORMATION: Self-cleaving linker T2A

<400> SEQUENCE: 26

Leu Glu Gly Gly Gly Glu Gly Arg Gly Ser Leu Leu Thr Cys Gly
1               5                   10                  15

<210> SEQ ID NO 27
<211> LENGTH: 11
<212> TYPE: PRT
<213> ORGANISM: Artificial Sequence
<220> FEATURE:
<223> OTHER INFORMATION: Variable light chain comprising a CDRL1

<400> SEQUENCE: 27

Arg Ala Ser Gln Asp Ile Ser Lys Tyr Leu Asn
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Variable light chain comprising CDRL2

<400> SEQUENCE: 28

Ser Arg Leu His Ser Gly Val
1               5

<210> SEQ ID NO 29
<211> LENGTH: 9
<212> TYPE: PRT
<213> ORGANISM: Artificial Sequence
<220> FEATURE:
<223> OTHER INFORMATION: Variable light chain comprising CDRL3
```

```
<400> SEQUENCE: 29

Gly Asn Thr Leu Pro Tyr Thr Phe Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Variable heavy chain comprising CDRH1

<400> SEQUENCE: 30

Asp Tyr Gly Val Ser
1               5

<210> SEQ ID NO 31
<211> LENGTH: 16
<212> TYPE: PRT
<213> ORGANISM: Artificial Sequence
<220> FEATURE:
<223> OTHER INFORMATION: Variable heavy chain comprising CDRH2

<400> SEQUENCE: 31

Val Ile Trp Gly Ser Glu Thr Thr Tyr Tyr Asn Ser Ala Leu Lys Ser
1               5                   10                  15

<210> SEQ ID NO 32
<211> LENGTH: 5
<212> TYPE: PRT
<213> ORGANISM: Artificial Sequence
<220> FEATURE:
<223> OTHER INFORMATION: Variable heavy chain comprising CDRH3

<400> SEQUENCE: 32

Tyr Ala Met Asp Tyr
1               5

<210> SEQ ID NO 33
<211> LENGTH: 10
<212> TYPE: PRT
<213> ORGANISM: Artificial Sequence
<220> FEATURE:
<223> OTHER INFORMATION: Variable light chain comprising CDRL1

<400> SEQUENCE: 33

Arg Ala Ser Ser Ser Val Asn Tyr Met Asp
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Variable light chain comprising CDRL2

<400> SEQUENCE: 34

Ala Thr Ser Asn Leu Ala Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Variable light chain comprising CDRL3
```

<400> SEQUENCE: 35

Gln Gln Trp Ser Phe Asn Pro Pro Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Variable heavy chain comprising CDRH1 sequence,
      a synthetic humanized or human sequence

<400> SEQUENCE: 36

Ser Tyr Asn Met His
1               5

<210> SEQ ID NO 37
<211> LENGTH: 17
<212> TYPE: PRT
<213> ORGANISM: Artificial Sequence
<220> FEATURE:
<223> OTHER INFORMATION: CDRH2, variable heavy chain comprising a
      synthetic humanized or human sequence

<400> SEQUENCE: 37

Ala Ile Tyr Pro Gly Asn Gly Asp Thr Ser Tyr Asn Gln Lys Phe Lys
1               5                   10                  15

Gly

<210> SEQ ID NO 38
<211> LENGTH: 13
<212> TYPE: PRT
<213> ORGANISM: Artificial Sequence
<220> FEATURE:
<223> OTHER INFORMATION: Variable heavy chain comprising CDRH3, a
      synthetic humanized or human sequence

<400> SEQUENCE: 38

Ser Asn Tyr Tyr Gly Ser Ser Tyr Trp Phe Phe Asp Val
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Flexible linker amino acids

<400> SEQUENCE: 39

Gly Ser Thr Ser Gly Ser Gly Lys Pro Gly Ser Gly Glu Gly Ser Thr
1               5                   10                  15

Lys Gly

<210> SEQ ID NO 40
<211> LENGTH: 429
<212> TYPE: DNA
<213> ORGANISM: Artificial Sequence
<220> FEATURE:
<223> OTHER INFORMATION: Her2Domain IV and 7 amino acid linker

<400> SEQUENCE: 40
atgcttctcc tggtgacaag ccttctgctc tgtgagttac cacacccagc attcctcctg      60
atcccatgcc accctgagtg tcagccccag aatggctcag tgacctgttt tggaccggag     120
gctgaccagt gtgtggcctg tgcccactat aaggaccctc ccttctgcgt ggcccgctgc     180

```
cccagcggtg tgaaacctga cctctcctac atgcccatct ggaagtttcc agatgaggag    240
ggcgcatgcc agccttgccc catcaactgc acccactcct gtgtggacct ggatgacaag    300
ggctgccccg ccgagcagag agccagcccg ttaacgggtg gaggcagcgg aggtggctcc    360
atcatctctg cggtggttgg cattctgctg gtcgtggtct tgggggtggt ctttgggatc    420
ctcatctga                                                            429
```

```
<210> SEQ ID NO 41
<211> LENGTH: 142
<212> TYPE: PRT
<213> ORGANISM: Artificial Sequence
<220> FEATURE:
<223> OTHER INFORMATION: Her2Domain IV and 7 amino acid linker

<400> SEQUENCE: 41
```

```
Met Leu Leu Leu Val Thr Ser Leu Leu Leu Cys Glu Leu Pro His Pro
1               5                   10                  15

Ala Phe Leu Leu Ile Pro Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala Arg Cys Pro Ser Gly Val
    50                  55                  60

Lys Pro Asp Leu Ser Tyr Met Pro Ile Trp Lys Phe Pro Asp Glu Glu
65                  70                  75                  80

Gly Ala Cys Gln Pro Cys Pro Ile Asn Cys Thr His Ser Cys Val Asp
                85                  90                  95

Leu Asp Asp Lys Gly Cys Pro Ala Glu Gln Arg Ala Ser Pro Leu Thr
            100                 105                 110

Gly Gly Gly Ser Gly Gly Gly Ser Ile Ile Ser Ala Val Val Gly Ile
        115                 120                 125

Leu Leu Val Val Val Leu Gly Val Val Phe Gly Ile Leu Ile
    130                 135                 140
```

```
<210> SEQ ID NO 42
<211> LENGTH: 5
<212> TYPE: PRT
<213> ORGANISM: Artificial Sequence
<220> FEATURE:
<223> OTHER INFORMATION: Loop 1 of Her2 protein, protein region, human
      protein

<400> SEQUENCE: 42

Glu Ala Asp Gln Cys
1               5
```

```
<210> SEQ ID NO 43
<211> LENGTH: 4
<212> TYPE: PRT
<213> ORGANISM: Artificial Sequence
<220> FEATURE:
<223> OTHER INFORMATION: Loop 2 of Her2 protein, protein region, human
      protein

<400> SEQUENCE: 43

Asp Pro Pro Phe
1
```

```
<210> SEQ ID NO 44
<211> LENGTH: 10
```

```
<212> TYPE: PRT
<213> ORGANISM: Artificial Sequence
<220> FEATURE:
<223> OTHER INFORMATION: Loop 3 of Her2 protein, protein region, human
      protein

<400> SEQUENCE: 44

Phe Pro Asp Glu Glu Gly Ala Cys Gln Pro
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Synthetic linker

<400> SEQUENCE: 45

Gly Gly Gly Ser Gly Gly Gly Ser
1               5

<210> SEQ ID NO 46
<211> LENGTH: 1428
<212> TYPE: DNA
<213> ORGANISM: Artificial Sequence
<220> FEATURE:
<223> OTHER INFORMATION: CD19 CAR

<400> SEQUENCE: 46
atgctgctgc tggtgaccag cctgctgctg tgcgagctgc ccacccccgc ctttctgctg      60
atccccgaca tccagatgac ccagaccacc tccagcctga gcgccagcct gggcgaccgg     120
gtgaccatca gctgccgggc cagccaggac atcagcaagt acctgaactg gtatcagcag     180
aagcccgacg gcaccgtcaa gctgctgatc taccacacca gccggctgca cagcggcgtg     240
cccagccggt ttagcggcag cggctccggc accgactaca gcctgaccat ctccaacctg     300
gaacaggaag atatcgccac ctactttttgc cagcagggca cacactgcc ctacaccttt     360 ggcggcggaa caaagctgga aatcaccggc agcacctccg gcagcggcaa gcctggcagc     420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc ccccaggaag ggcctggaat ggctgggcgt gatctggggc     600
agcgagacca cctactacaa cagcgccctg aagagccggc tgaccatcat caaggacaac     660
agcaagagcc aggtgttcct gaagatgaac agcctgcaga ccgacgacac cgccatctac     720
tactgcgcca gcactacta ctacggcggc agctacgcca tggactactg gggccagggc     780
accagcgtga ccgtgagcag cgagagcaag tacggaccgc cctgcccccc ttgccctatg     840
ttctgggtgc tggtggtggt cggaggcgtg ctggcctgct acagcctgct ggtcaccgtg     900
gccttcatca tcttttgggt gaacgggggc agaaagaaac tcctgtatat attcaaacaa     960
ccatttatga tgaccagtaca aactactcaa gaggaagatg gctgtagctg ccgatttcca    1020
gaagaagaag aaggaggatg tgaactgcgg gtgaagttca gcagaagcgc cgacgcccct    1080
gcctaccagc agggccagaa tcagctgtac aacgagctga acctgggcag aagggaagag    1140
tacgacgtcc tggataagcg gagaggccgg gaccctgaga tgggcggcaa gcctcggcgg    1200
aagaaccccc aggaaggcct gtataacgaa ctgcagaaag acaagatggc cgaggcctac    1260
agcgagatcg gcatgaaggg cgagcggagg cggggcaagg gccacgacgg cctgtatcag    1320
ggcctgtcca ccgccaccaa ggataccttac gacgccctgc acatgcaggc cctgcccca    1380
```
aggctcgagg gcggcggaga gggcagagga agtcttctaa catgcggt            1428

<210> SEQ ID NO 47
<211> LENGTH: 36
<212> TYPE: DNA
<213> ORGANISM: Artificial Sequence
<220> FEATURE:
<223> OTHER INFORMATION: IgG4-Hinge

<400> SEQUENCE: 47
gagagcaagt acggaccgcc ctgccccct tgccct                          36

<210> SEQ ID NO 48
<211> LENGTH: 321
<212> TYPE: DNA
<213> ORGANISM: Artificial Sequence
<220> FEATURE:
<223> OTHER INFORMATION: CH3 hinge region

<400> SEQUENCE: 48
ggccagcctc gcgagcccca ggtgtacacc ctgcctccct cccaggaaga gatgaccaag   60
aaccaggtgt ccctgacctg cctggtgaag ggcttctacc ccagcgacat cgccgtggag  120
tgggagagca acggccagcc tgagaacaac tacaagacca cccctcccgt gctggacagc  180
gacggcagct tcttcctgta cagccggctg accgtggaca gagccggtg gcaggaaggc  240 aacgtcttta gctgcagcgt gatgcacgag gccctgcaca accactacac ccagaagagc  300
ctgagcctgt ccctgggcaa g                                            321

<210> SEQ ID NO 49
<211> LENGTH: 12
<212> TYPE: PRT
<213> ORGANISM: Artificial Sequence
<220> FEATURE:
<223> OTHER INFORMATION: IgG4-Hinge

<400> SEQUENCE: 49

Glu Ser Lys Tyr Gly Pro Pro Cys Pro Pro Cys Pro
1               5                   10

<210> SEQ ID NO 50
<211> LENGTH: 107
<212> TYPE: PRT
<213> ORGANISM: Artificial Sequence
<220> FEATURE:
<223> OTHER INFORMATION: CH3 hinge region

<400> SEQUENCE: 50

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

```
Asn Val Phe Ser Cys Ser Val Met His Glu Ala Leu His Asn His Tyr
                85                  90                  95
Thr Gln Lys Ser Leu Ser Leu Ser Leu Gly Lys
            100                 105
```